(12) United States Patent
Hasumi et al.

(10) Patent No.: US 7,939,536 B2
(45) Date of Patent: May 10, 2011

(54) PYRIMIDINYLISOXAZOLE DERIVATIVES

(75) Inventors: Koichi Hasumi, Tokyo (JP); Shuji Ohta, Kawasaki (JP); Takahisa Saito, Kawasaki (JP); Shuichiro Sato, Tokyo (JP); Jun-ya Kato, Kawasaki (JP); Jun Sato, Kawasaki (JP); Hiroyuki Suzuki, Kawasaki (JP); Hajime Asano, Kawasaki (JP); Mami Okada, Kawasaki (JP); Yasuhiro Matsumoto, Kawasaki (JP); Kazuhiko Shirota, Kawasaki (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 900 days.

(21) Appl. No.: 11/794,180

(22) PCT Filed: Dec. 27, 2005

(86) PCT No.: PCT/JP2005/024244
§ 371 (c)(1),
(2), (4) Date: Jun. 26, 2007

(87) PCT Pub. No.: WO2006/070927
PCT Pub. Date: Jul. 6, 2006

(65) Prior Publication Data
US 2008/0114003 A1    May 15, 2008

(30) Foreign Application Priority Data
Dec. 28, 2004  (JP) .................. 2004-381733

(51) Int. Cl.
*C07D 413/04*   (2006.01)
*A61K 31/506*   (2006.01)
(52) U.S. Cl. ...................... 514/256; 544/333
(58) Field of Classification Search .................. 544/333; 514/256
See application file for complete search history.

(56) References Cited

U.S. PATENT DOCUMENTS
6,511,997 B1  1/2003  Minami et al.
2006/0128759 A1  6/2006  Laufer et al.

FOREIGN PATENT DOCUMENTS
| JP | 2000-086657 | 3/2000 |
| JP | 2002-179656 | 6/2002 |
| WO | 93/14081 | 7/1993 |
| WO | 98/52940 | 11/1998 |
| WO | 02/083668 | 10/2002 |
| WO | 03/004492 | 1/2003 |
| WO | 2004/022555 | 3/2004 |

OTHER PUBLICATIONS

Damassio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Simone, Oncology: Introduction, Cecil Textbook of Medicine, 20$^{th}$ Edition, vol. 1, pp. 1004-1010, 1996.*
Douglas, Jr. Introduction to Viral Diseases, Cecil Textbook of Medicine, 20$^{th}$ Edition, vol. 2, pp. 1739-1747, 1996.*
Timothy F. Gallagher et al., "Regulation of Stress-Induced Cytokine Production by Pyridinylimidazoles; Inhibition of CSBP Kinase", Bioorganic & Medicinal Chemistry, vol. 5, No. 1, pp. 49-64 (1997).
Katerina Leftheris et al., "The Discovery of Orally Active Triaminotriazine Aniline Amides as Inhibitors of p38 MAP Kinase", Journal of Medicinal Chemistry, vol. 47, pp. 6283-6291 (2004).
Supplementary European Search Report issued Aug. 10, 2010 in corresponding European Application No. 05 82 4638, in the English language, Aug. 2010.

* cited by examiner

*Primary Examiner* — Deepak Rao
(74) *Attorney, Agent, or Firm* — Wenderoth, Lind & Ponack, L.L.P.

(57) ABSTRACT

The invention discloses isoxazole derivatives represented by a formula,

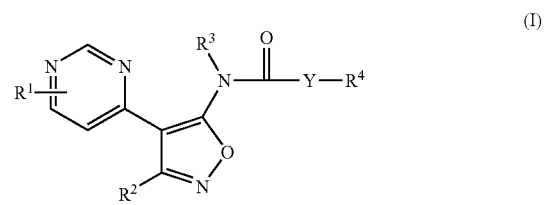

(I)

in which
$R^1$ stands for hydrogen, lower alkyl, amino, halogen, lower alkoxy and the like,
$R^2$ stands for substituted or unsubstituted aryl and the like,
$R^3$ stands for hydrogen or lower alkyl,
$R^4$ stands for substituted or unsubstituted phenyl and the like, and
Y stands for —$CH_2$—, —CO—, —$CH(CH_3)$—, —O—, —NH— and the like, or pharmaceutically acceptable salts thereof, which have excellent p38MAPkinase inhibitory action.

10 Claims, No Drawings

PYRIMIDINYLISOXAZOLE DERIVATIVES

This application is a 371 of PCT/JP05/24244 filed Dec. 27, 2005.

TECHNICAL FIELD

This invention relates to novel pyrimidinylisoxazole derivatives or salts thereof, methods of their preparation and their use. Compounds of this invention exhibit p38MAPkinase inhibiting action and in consequence inhibitory action to the production of tumor necrosis factor-α (TNF-α), interleukin-1 (IL-1), interleukin-6 (IL-6), interleukin-8 (IL-8), cyclooxygenase-II (COX-II) and the like. They are, therefore, useful as the treating agent of TNF-α-related diseases, IL-1-related diseases, IL-6-related diseases, IL-8-related diseases and COX-II-related diseases.

BACKGROUND ART

TNF-α, IL-1, IL-6, IL-8 and COX-II are mainly the proteins (cytokines) produced by immunocompetent cells such as macropharge and neutrophil, which are known as one of the important factors participating in, besides immunomodulatory function and inflammatory symptoms, the hematopoietic system, endocrine system, nervous system and the like.

On the other hand, p38MAPkinase has the action of activating transcription factors such as NF-κB, AP-1 and CREB. These transcription factors bind to the DNA sequence common among TNF-α, IL-1, IL-6, IL-8, COX-II and the like to promote transcription of mRNA which synthesizes the respective cytokines. p38MAPkinase, therefore, has the action to promote the production of cytokines such as TNF-α. While the transcribed mRNA is inactivated upon binding to specific protein and then quickly degraded, p38MAPkinase has an action to dissociate the bonds between mRNA and the specific proteins. In this respect also p38MAPkinase is deemed to contribute to the production of cytokines such as TNF-α.

Accordingly, inhibition of p38MAPkinase leads to inhibition of the production of cytokines such as TNF-α and, therefore, is expected to be useful for the treatment or prophylaxis of the diseases related to the cytokines such as TNF-α, for example, acute inflammation, chronic inflammation, rheumatoid arthritis, osteoarthritis, gout, inflammatory bowel disease, Crohn's disease, ulcerative colitis, gastritis, colonic polyposis, large bowel cancer, colon cancer, asthma, bronchitis, bronchial asthma, allergic rhinitis, ARDS (acute respiratory distress syndrome), chronic obstructive pulmonary disease, pulmonary fibrosis, congestive heart disease, ischemic heart disease, myocardial infarction, arteriosclerosis, hypertension, angina, Alzheimer's disease, reperfusion injury, angiitis, cerebrovascular disease, meningitis, multiple sclerosis, osteoporosis, bony sclerosis, Behcet's Syndrome, bone metastasis, multiple myeloma, acute infectious disease, septic shock, sepsis, toxic-shock syndrome, tuberculosis, DIC (disseminated intravascular coagulation), psoriasis, atopic dermatitis, cirrhosis, renal fibrosis, cachexia, AIDS (acquired immunodeficiency syndrome), cancer, autoimmune disease, diabetes, Castleman's disease, mesangial nephritis, endometriosis and preterm delivery.

In the past, as the compounds having p38MAPkinase-inhibiting action, for example imidazole derivatives (cf. Bioorganic & Medicinal Chemistry, Vol. 5, No. 1, 49-64 (1997) and JP Tokuhyo Hei 7 (1995)-503017), pyrazole derivatives (cf. PCT International Publications WO98/52940 Pamphlet and WO0/39116 Pamphlet) and isoxazole derivatives (cf. JP Tokuhyo Hei 11 (1999)-503722, JP2002-179656A, PCT International Publication WO2004/17968 Pamphlet, JP 2000-86657A and PCT International Publication WO2004/22555 Pamphlet) have been proposed. However, these compounds are subject to such problems that most of them exhibit side effects and have not matured as marketable medicines.

Only recently Katerina Leftheris, et al. announced that certain kind of triazine derivatives possessed potent p38MAPkinase-inhibiting action and high speed metabolism, and hence were expected to show reduced side effects and to be prospective antirheumatic medicine (cf. J. Med. Chem., Vol. 47, 6283-6291 (2004)).

DISCLOSURE OF THE INVENTION

An object of the present invention is to provide pyrimidinylisoxazole derivatives-which exhibit excellent p38MAPkinase-inhibiting activity and reduced side effects.

We have now discovered that a certain kind of novel 4-(4-pyrimidinyl)isoxazole derivatives possess excellent p38MAPkinase-inhibiting activity and high expiration rate of metabolically active substance in blood, and hence have the potential to reduce the side effects which have been the drawback in past p38MAPkinase-inhibitors, and completed the present invention.

Thus, according to the present invention, pyrimidinylisoxazole derivatives which are represented by the formula (I)

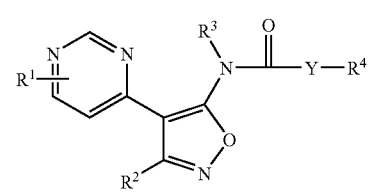

(I)

wherein
$R^1$ stands for hydrogen, lower alkyl, amino, lower alkylamino, di-lower alkylamino, phenyl lower alkylamino, acylamino, halogen, lower alkoxy, lower alkylthio or lower alkylsulfinyl,
$R^2$ stands for unsubstituted aryl or heteroaryl, or aryl or heteroaryl which is substituted with 1-3 substituents selected from halogen, lower alkyl, lower alkoxy, lower haloalkyl, lower alkylenedioxy and benzyloxy,
$R^3$ stands for hydrogen or lower alkyl,
$R^4$ stands for substituted or unsubstituted phenyl, or substituted or unsubstituted heterocyclic group, and
Y stands for —(CH$_2$)$_n$—, —CO—, —CH(CH$_3$)—, —O—, —NH—,

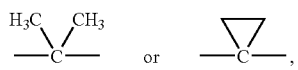

n being an integer of 0-3, or pharmaceutically acceptable salts thereof are provided.

According to the present invention, p38MAPkinase-inhibitors are also provided, which are characterized by comprising the pyrimidinylisoxazole derivatives of the formula (I) or their pharmaceutically acceptable salts thereof.

In the present specification, the term, "lower" signifies that the groups affixed with this prefix each has a carbon number not more than 6, preferably not more than 4.

"Lower alkyl" may be linear or branched, examples of which include methyl, ethyl, n-propyl, isopropyl, n-butyl, isobutyl, sec-butyl, tert-butyl, n-pentyl and n-hexyl. Of these, methyl, ethyl, n-propyl, isopropyl and n-butyl are preferred. "Lower alkoxy" are the oxy (O) groups substituted with the lower alkyl groups, their examples including methoxy, ethoxy, n-propoxy, isopropoxy, n-butoxy, isobutyloxy, sec-butyloxy, n-pentyloxy and n-hexyloxy. Of these, methoxy, ethoxy, n-propoxy, isopropoxy and n-butoxy are preferred.

Furthermore, "halogen" includes fluorine, chlorine, bromine and iodine, among which fluorine, chlorine and bromine atoms are particularly preferred.

"Lower alkylamino" named in the definition of $R^1$ signifies the amino groups which are substituted with one of above-named lower alkyl groups, and "di-lower alkylamino" signifies the amino groups which are substituted with two of above-named lower alkyl groups, where the two alkyl groups in a di-lower alkylamino may be same or different. Again, "phenyl lower alkylamino" signifies the above lower alkylamino groups wherein the lower alkyl moiety therein is further substituted with one phenyl group.

"Lower alkylthio" and "lower alkylsulfinyl" in the definition of $R^1$ respectively signify thio (S) and sulfinyl (SO) which are substituted with aforesaid lower alkyl.

"Acylamino" in the definition of $R^1$ signifies acylated amino, examples of the acyl including lower alkanonyl such as formyl, acetyl, propionyl and butyryl, and aroyl such as benzoyl. Of these, acetyl and benzoyl are preferred.

As "aryl" in the definition of $R^2$, for example, phenyl and naphthyl can be named, among which phenyl is preferred. "Heteroaryl" in the definition of $R^2$ includes 5- to 6-membered heteroaryl groups having 1 to 2 hetero atoms selected from N, O and S, which may be condensed with benzene ring, example thereof including pyridyl, quinolyl, pyrrolyl, furyl, thienyl, imidazolyl, pyrazolyl, oxazolyl, isoxazolyl and thiazolyl. Of these, pyridyl is particularly preferred.

"Lower haloalkyl" in the definition of $R^2$ signifies the alkyl groups as named in the above, which are substituted with one or more same or different halogen atoms, examples thereof including fluoromethyl, trifluoromethyl, 1,2-dichloroethyl, 1-chloro-2-bromoethyl, pentafluoroethyl, 1-chloro-n-propyl, 2-bromo-2-methylethyl, 3-chloro-n-pentyl and 2-bromo-3-chloro-n-hexyl. Of these, particularly $C_1$-$C_2$ lower alkyl groups which are substituted with 1-5 same or different halogen atoms are preferred.

As "lower alkylenedioxy" in the definition of $R^2$, for example, methylenedioxy, ethylenedioxy and trimethylenedioxy can be named, methylenedioxy being particularly preferred.

"Heterocyclic group" in the definition of $R^4$ includes saturated or unsaturated 5- to 7-membered heterocyclic groups which may be forming a condensed ring, having 1-3 hetero atoms selected from N, O and S. As their examples pyridyl, pyrimidinyl, azepinyl, quinolyl, indolyl, quinazolinyl, pyrrolyl, furyl, thienyl, imidazolyl, pyrazolyl, isoxazolyl, thiazolyl, pyrrolidinyl and isochromanyl can be named, among which thienyl and isoxazolyl are preferred.

As the substituent on the phenyl group in "substituted or unsubstituted phenyl" in the definition of $R^4$, for example, halogen, lower alkyl, lower alkoxy, nitro, lower haloalkyl, lower haloalkylthio, hydroxyl and amino can be named. Of these, halogen, lower alkyl, lower alkoxy, nitro, lower haloalkyl and lower haloalkylthio are preferred, halogen and lower alkyl being particularly preferred. Also as the substituent on the heterocyclic group in "substituted or unsubstituted heterocyclic group" in the definition of $R^4$, for example, halogen, lower alkyl, lower alkoxy, nitro, lower haloalkyl and amino can be named, halogen and lower alkyl being particularly preferred.

A preferred group of the compounds of the present invention are those of the formula (I) wherein $R^1$ stands for hydrogen, amino, lower alkylamino or di-lower alkylamino. In particular, those compounds of the formula (I) wherein $R^1$ stands for hydrogen are more preferred. The preferred substitution site of $R^1$ is the 2-position on the pyrimidine ring.

Another preferred group of the compounds of the present invention are those of the formula (I) wherein $R^2$ stands for phenyl which is substituted with 1-3 substituents selected from halogen, lower alkyl, lower alkoxy and lower alkylenedioxy. In particular, such compounds of the formula (I) wherein $R^2$ stands for phenyl which is substituted with 1 or 2 substituents selected from halogen, lower alkyl and lower alkylenedioxy are more preferred. In the most preferred compounds of this group, $R^2$ is 4-fluorophenyl, 2,4-difluorophenyl, 4-chlorophenyl, 3-methylphenyl, 2-fluoro-5-methylphenyl, 4-fluoro-3-methylphenyl, 2-fluoro-4-methoxyphenyl or 2,3-methylenedioxyphenyl.

Still another preferred group of the compounds of the present invention are those of the formula (I) wherein $R^3$ stands for hydrogen.

An other preferred group of the compounds of the invention are those of the formula (I) wherein $R^4$ stands for substituted or unsubstituted phenyl; in particular, unsubstituted phenyl or phenyl substituted with 1 or 2 substituents selected from halogen, lower alkyl and lower alkoxy. More preferably, in the compounds of the formula (I), $R^4$ is unsubstituted phenyl, 2-halophenyl, 2,6-dihalophenyl, 2-lower alkylphenyl, 3-lower alkylphenyl, 3-lower alkoxyphenyl or 2,5-di-lower alkylphenyl.

Also another preferred group of the compounds of the present invention are those of the formula (I) wherein Y stands for —$CH_2$—.

Typical examples of the compounds of the formula (I) which are provided by the present invention include, besides those formed in the later given Examples, the following:
3-(4-fluorophenyl)-4-[4-(2-methylaminopyrimidinyl)]-5-(phenylacetylamino)isoxazole,
5-[(2-chlorophenyl)acetylamino]-3-(4-fluorophenyl)-4-[4-(2-methylaminopyrimidinyl)]isoxazole,
4-[4-(2-dimethylaminopyrimidinyl)]-3-(4-fluorophenyl)-5-(phenylacetylamino)isoxazole,
5-[(2-chlorophenyl)acetylamino)-4-[4-(2-dimethylaminopyrimidinyl)]-3-(4-fluorophenyl)isoxazole,
4-[4-(2-benzylaminopyrimidinyl)]-3-(4-fluorophenyl)-5-(phenylacetylamino)isoxazole,
4-[4-(2-benzylaminopyrimidinyl)]-5-[(2-chlorophenyl)acetylamino]-3-(4-fluorophenyl)isoxazole,
4-[4-(2-acetylaminopyrimidinyl)]-3-(4-fluorophenyl)-5-(phenylacetylamino)isoxazole,
4-[4-(2-acetylaminopyrimidinyl)]-5-[(2-chlorophenyl)acetylamino]-3-(4-fluorophenyl)isoxazole,
4-[4-(2-benzoylaminopyrimidinyl)]-3-(4-fluorophenyl)-5-(phenylacetylamino)isoxazole,
4-[4-(2-benzoylaminopyrimidinyl)]-5-[(2-chlorophenyl)acetylamino]-3-(4-fluorophenyl)isoxazole,
3-(4-fluorophenyl)-5-(N-methyl-phenylacetylamino)-4-(4-pyrimidinyl)isoxazole,
3-(4-fluorophenyl)-5-[(2-chlorophenyl)acetyl-N-methylamino]-4-(4-pyrimidinyl)isoxazole,
5-(N-ethyl-phenylacetylamino)-3-(4-fluorophenyl)-4-(4-pyrimidinyl)isoxazole,
5-[(2-chlorophenyl)acetyl-N-ethylamino]-3-(4-fluorophenyl)-4-(4-pyrimidinyl)isoxazole, 3-[4-(2-methylpyridyl)]-5-(phenylacetylamino)-4-(4-pyrimidinyl)isoxazole, 5-[(2-chlorophenyl)acetylamino]-3-[4-(2-methylpyridyl)]-4-(4-pyrimidinyl)isoxazole, 3-[2-(6-methylpyridyl)]-5-(phenylacetylamino)-4-(4-pyrimidinyl)isoxazole, 5-[(2-chlorophenyl)acetylamino]-3-[2-(6-methylpyridyl)]-4-(4-pyrimidinyl)isoxazole 3-[2-(4-methylpyridyl)]-5-(phenylacetylamino)-4-(4-pyrimidinyl)isoxazole, and 5-[(2-chlorophenyl)acetylamino]-3-[2-(4-methylpyridyl)]-4-(4-pyrimidinyl)isoxazole.

Compounds of the formula (I) can optionally be present in the form of salts. As the salts, those with inorganic acid such as hydrochloric acid, hydrobromic acid, sulfuric acid, nitric acid, phosphoric acid and the like; and those with organic acid such as acetic acid, oxalic acid, citric acid, lactic acid, tartaric acid, p-toluenesulfonic acid and the like can be named. Of these, pharmaceutically acceptable salts are preferred.

Compounds of the formula (I) according to the present invention can be prepared, for example, by the methods (a) or (b) as described in the following.

Method (a): The compounds of the formula (I) wherein $R^3$ stands for hydrogen, i.e., the compounds of the following formula,

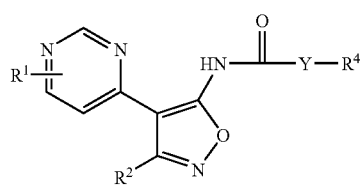

(I-1)

in which $R^1$, $R^2$, $R^4$ and Y have the earlier defined significations, can be prepared by reacting the compounds of the following formula,

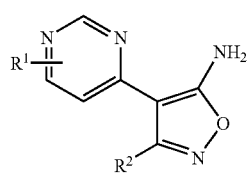

(II)

in which $R^1$ and $R^2$ have the earlier defined significations, with carboxylic acid compounds of the following formula,

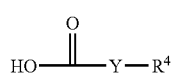

(III)

in which $R^4$ and Y have the earlier defined significations, or their reactive derivatives (e.g., acid halide, acid anhydride, mixed acid anhydride, active amide, active ester and the like).

Method (b): The compounds of the formula (I) wherein $R^3$ stands for lower alkyl, i.e., the compounds of the following formula,

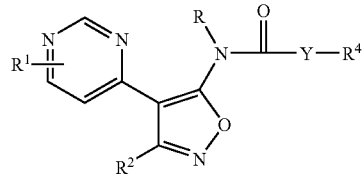

(I-2)

in which $R^1$, $R^2$, $R^4$ and Y have the earlier defined significations, and R stands for lower alkyl, can be prepared by N-lower alkylating the compounds of the formula (I-1).

In the method (a), it is desirable that the carboxylic acid compound of the formula (III) is advancedly treated with, for example, 1,1-carbonyldiimidazole (CDI), 1,1-thionyldiimidazole or the like, to be converted to a reactive derivative thereof such as active amide. It is also possible when acid halide, for example, acid chloride, is used as the reactive derivative of the carboxylic acid compound of the formula (III), to treat the acid halide in advance with, for example, imidazole and DBU or the like to convert it to other reactive derivative such as imidazolide.

Furthermore, when $R^1$ in the compounds of the formula (II) represents amino or lower alkylamino, it is advantageous to protect the amino or lower alkylamino in advance with a suitable protective group, for example, with the use of di-tert-butyl dicarbonate (BOC), acetonyl acetone, benzyloxycarbonyl chloride (Z-chloride) or the like where necessary, removing the protective group after termination of the reaction.

The reaction of a compound of the formula (II) with a carboxylic acid compound of the formula (III) or a reactive derivative thereof can generally be conducted in inert organic solvent, for example, ethers such as dioxane, tetrahydrofuran and dimethoxyethane; aromatic hydrocarbons such as benzene, toluene and xylene; halogenated hydrocarbons such as dichloromethane and chloroform; amides such as dimethylformamide and dimethyl-acetamide; dimethylsulfoxide; and, where necessary, in the presence of a base, for example, 1,8-diazabicyclo[5.4.0]undec-7-ene (DBU), triethylamine, diisopropylethylamine, pyridine or the like. The suitable reaction temperature is normally within a range of 0° C. to the reflux temperature of the reaction mixture under use, preferably from the temperature under cooling with ice up to 50° C.

The carboxylic acid compound of the formula (III) or reactive derivative thereof can be generally used in an amount of at least 1 mol, preferably 1.5-10 mols, inter alia, 2-5 mols, per mol of the compound of the formula (II). Also the use rate of the base is generally at least 1 mol, preferably 1-2 mols, per mol of the carboxylic acid compound of the formula (III) or reactive derivative thereof.

Compounds of the formula (II) which are used as the starting material can be readily synthesized by those synthesis methods known per se, for example, following the route indicated by the following reaction scheme 1. Concerning the particulars of the reaction conditions and the like of the reaction scheme 1, refer to Example 1, a)-c) given later.

Reaction scheme 1:

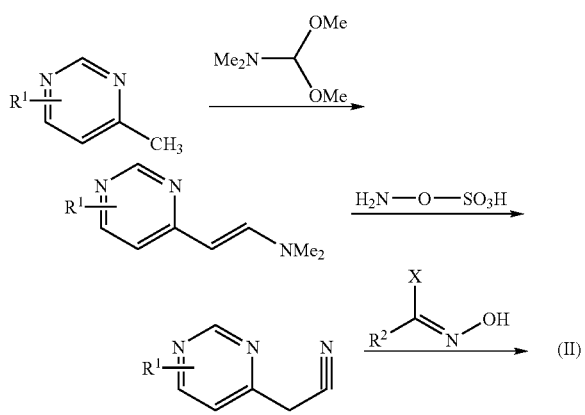

in which $R^1$ and $R^2$ have the earlier defined significations, and X stands for halogen.

The N-lower alkylation of the compounds of the formula (I-1) according to the method (b) can generally be carried out by reacting the compounds with lower alkyl halide, for example, iodomethane, ethyl bromide, propyl bromide and the like, in inert organic solvent, for example, alcohols such as methanol, ethanol and isopropanol; ethers such as dioxane, tetrahydrofuran and dimethoxyethane, aromatic hydrocarbons such as benzene, toluene and xylene; amides such as dimethylformamide and dimethylacetamide; and dimethylsulfoxide; and in the presence of a suitable base such as sodium hydride, potassium carbonate, pyridine and the like. The suitable reaction temperature is normally within a range of 0° C. to the reflux temperature of the reaction mixture under use, preferably from room temperature to 50° C.

The lower alkyl halide can be used generally in an amount of at least 1 mol, preferably 1.1-5 mols, inter alia, 1.2-4 mols, per mol of a compound of the formula (I-1). The use rate of the base is generally at least 1 mol, preferably within a range of 1-5 mols, per mol of a compound of the formula (I-1).

Those compounds of the formula (I) of the present invention which are prepared following the above-described methods can be isolated and purified by the means known per se, for example, recrystallization, column chromatography, preparative chromatography and the like.

The pyrimidinylisoxazole derivatives represented by the formula (I) of the present invention or their pharmaceutically acceptable salts possess excellent p38MAPkinase-inhibiting action with reduced side effects, and are useful for the treatment or prophylaxis of human and other mammals' TNF-α-related disease, IL-1-related disease, IL-6-related disease, IL-8 related disease, COX-II related disease, for example, acute inflammation, chronic inflammation, rheumatoid arthritis, osteoarthritis, gout, inflammatory bowel disease, Crohn's disease, ulcerative colitis, gastritis, colonic polyposis, large bowel cancer, colon cancer, asthma, bronchitis, bronchial asthma, allergic rhinitis, ARDS (acute respiratory distress syndrome), chronic obstructive pulmonary disease, pulmonary fibrosis, congestive heart disease, ischemic heart disease, myocardial infarction, arteriosclerosis, hypertension, angina, Alzheimer's disease, reperfusion injury, angiitis, cerebrovascular disease, meningitis, multiple sclerosis, osteoporosis, bony sclerosis, Behcet's Syndrome, bone metastasis, multiple myeloma, acute infectious disease, septic shock, sepsis, toxic-shock syndrome, tuberculosis, DIC (disseminated intravascular coagulation), psoriasis, atopic dermatitis, cirrhosis, renal fibrosis, cachexia, AIDS (acquired immunodeficiency syndrome), cancer, autoimmune disease, diabetes, Castleman's disease, mesangial nephritis, endometriosis and preterm delivery.

The TNF-α production inhibitory action of possessed by the compounds of the formula (I) of the present invention, metabolic elimination rate of the compounds in blood, and pP38MAPkinase-inhibiting action of the compounds of the formula (I) is demonstrated in the following experiments.

(1) Measurement of TNF-α Production-inhibiting Action

THP-1, human-derived culture cells (purchased from Dainippon Pharmaceutical), was suspended ($1 \times 10^5$ cells/mL) in RPMI 1640 medium (10% fetal bovine serum, containing 100 units/mL of penicillin). The THP-1 cell suspension 1.6 mL was inoculated in a 24-well plate culture, to which further 0.2 mL of a test substance as dissolved in RPMI 1640 medium and 0.2 mL of LPS (*E. coli* 055: B5-derived, dissolved in RPMI 1640 medium, Difco) of 10 µg/mL in concentration were added, followed by 2 hours' culture under the conditions of 37° C. and 5% $CO_2$. The supernatant which was obtained upon centrifuge (500×g, 5 minutes) was measured with ELISA (Amersham Biosciences, TNF-α Human, ELISA Biotrak System) to quantize TNF-α. The 50% inhibitory concentration ($IC_{50}$) of each test substance was calculated as follows. First, TNF-α production inhibition rates (%) at various concentration levels were calculated according to the following formula, $$\left[1 - \frac{\text{quantity of } TNF\text{-}\alpha \text{ when each test substance was used}}{\text{quantity of } TNF\text{-}\alpha \text{ in control experiment}}\right] \times 100$$

The TNF-α production inhibition rate (%) as obtained from the above formula and the concentration of the test compound in each test were calculated on Prism 4 for Windows Ver 4.02 (Graph Pad Software, Inc.) to determine $IC_{50}$ value. The results are shown in the later-appearing Table A, concurrently with the metaboric rate of each of the compound, which was measured as in the following (2).

(2) Measurement of the Compounds' Metabolic Rate:

Each test compound was added to potassium phosphate buffer (50 mmol/L, pH7.4) containing NADPH generating system (comprising 3.3 mmol/L $MgCl_2$, 3.3 mmol/L glucose 6-phosphate, 1.3 mmol/L β-$NADP^+$ and 0.4 unit/mL glucose 6-phosphate dehydrogenase) (in which occasion the final concentration was rendered 1 µmol/L) and incubated at 37° C. for 2 minutes. After the incubation, a suspension of human liver S9(the supernatant fraction obtained by centrifuging comminuted human liver cell fluid at 9000×g) in potassium phosphate buffer was added to the system, to the final concentration of 0.5 mg protein/mL. This reaction mixture was incubated at 37° C. for 5 minutes, and to which 4 volume times the reaction mixture of acetonitrile was added, mixed, cooled with ice and centrifuged (2000×g, 10 minutes). A part of the supernatant was taken and analyzed by LC/MS/MS, to determine the remaining rate of unchanged substance in the reaction mixture. The results are shown in the following Table A, concurrently with the measured results of TNF-α production inhibition action in (1) above.

TABLE A

| Compound | Structural formula | TNF-α generation-inhibiting action (IC$_{50}$: nM) | Metabolic rate (remaining rate of unchanged substance: %) |
|---|---|---|---|
| Example 5 | | 36.1 | 5.8 |
| Example 13 | | 67.9 | 16.1 |
| Example 61 | | 48.7 | 53.1 |
| Example 105 | | 32.1 | 20.4 |
| Example 121 | | 139 | 46.6 |

TABLE A-continued
| Compound | Structural formula | TNF-α generation-inhibiting action (IC$_{50}$: nM) | Metabolic rate (remaining rate of unchanged substance: %) |
|---|---|---|---|
| Example 174 | 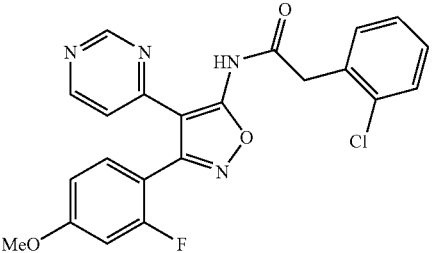 | 28.5 | 24.1 |
| Example 201 | 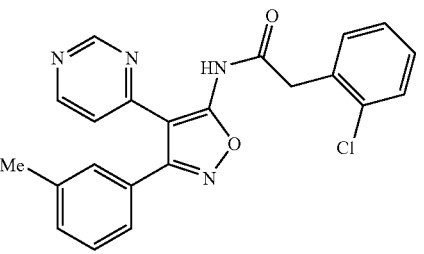 | 36.7 | 21.2 |
| Example 202 | 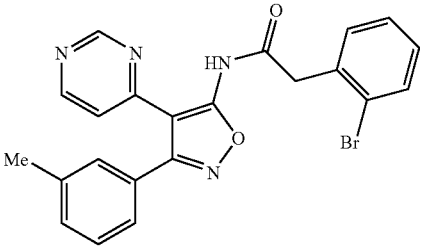 | 49.2 | 43.6 |
| Example 214 | 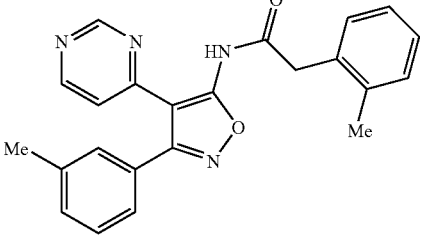 | 13.4 | 59.9 |
| Example 215 | 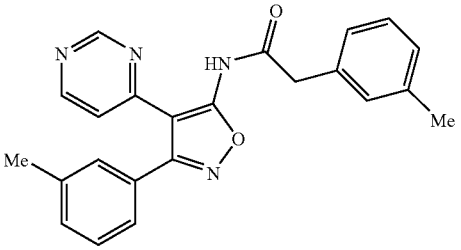 | 152 | 38.5 |

TABLE A-continued

| Compound | Structural formula | TNF-α generation-inhibiting action (IC$_{50}$: nM) | Metabolic rate (remaining rate of unchanged substance: %) |
|---|---|---|---|
| Example 224 | | 90.5 | 39.8 |
| Example 253 | | 52.6 | 33.1 |
| Example 257 | | 13.7 | 52.6 |

(3) Measurement of p38MAPkinase Inhibitory Activity:

Recombinant protein in which human p38MAPkinase was expressed on *E. coli* was used as the enzyme source, and as the substrate 10 μg/mL Myelin Basic Protein (MBP) was used. The incubation buffer used comprised 50 mmol/L HEPES, 20 mmol/L MgCl$_2$, 0.2 mmol/L Na$_3$ VO$_4$ and 1 mmol/L dithiothreitol (DTT) at pH 7.4. The measurement was conducted by phosphorization of MBP with p38MAPkinase by ELISA method. The incubation temperature and time were: at 25° C. for 15 minutes for preincubation, and at 25° C. for 60 minutes for the incubation. The concentration of each of the compounds was 1 nmol/L-10 μmol/L. As the vehicle, 1% DMSO was used. The results of the measurement were as shown in the following Table B.

TABLE B

| Compound | IC$_{50}$ (nM) to p38MAPkinase α |
|---|---|
| Example 13 | 19.0 |
| Example 201 | 9.32 |

Thus the pyrimidinylisoxazole derivatives represented by the formula (I) of the present invention or their pharmaceutically acceptable salts can be orally or parenterally (e.g., intramuscular injection, intravenous injection, intrarectal or percutaneous administration and the like) administered to patients as medicines for therapy, treatment or prophilaxis of human or other mammals' diseases, as p38MAPkinase inhibitor having excellent activity and high metaboric rate.

Where the compounds of the present invention are used as medicine, they can be formulated into preparation forms according to their utility, with non-toxic adjuvants, such as solids (e.g., tablet, hard capsule, soft capsule, granule, powder, grain, pill, troche and the like); semi-solids (e.g., suppository, ointment and the like) or liquid (e.g., injection, emulsion, suspension, lotion, spray and the like). As the non-toxic adjuvants useful for such preparations, for example, starch, gelatine, glucose, lactose, fructose, maltose, magnesium carbonate, talc, magnesium stearate, methyl cellulose, carboxymethyl cellulose or salts thereof, gum arabic, polyethylene glycol, alkyl p-hydroxybenzoate, syrup, ethanol, propylene glycol, petrolatum, carbowax, glycerine, sodium chloride, sodium sulfite, sodium phosphate, citric acid and the like can be named. The preparations can also contain other therapeutically useful medicines.

While the content of a compound of the present invention in such preparations differs according to the preparation form, in general terms it is desirable to be within a range of 0.1-50% by weight for solid and semi-solid forms, and within a range of 0.05-10% by weight for liquid forms.

The administration dosage of a compound of the present invention is variable over a wide range according to the species, age, body weight, administration route, seriousness of symptoms and doctor's diagnosis, of the patient including human and other warm-blooded animals. Whereas, in general terms, it can range 0.02-20 mg/kg, preferably 0.2-8 mg/kg, per day. Obviously, dosages less than the lower limit or more than the upper limit of the above-specified range may be administered depending on seriousness of the patient's symptoms, doctor's diagnosis and the like. The dosage can be administered as a single dose or plural divided doses per day.

EXAMPLES

The following Examples and Preparation Example more specifically explain the present invention.

Example 1

3-(4-Fluorophenyl)-5-(phenylacetylamino)-4-(4-pyrimidinyl)-isoxazole a: Synthesis of dimethyl-[(E)-2-(4-pyrimidinyl)vinyl]amine A mixture of 10 g of 4-methylpyrimidine, 38 g of N,N-dimethylformamide dimethylacetal (DMFDMA) and 46.6 g of DMF was stirred in a sealed tube at 140° C. for 24 hours. The reaction solution was cooled and the solvent was distilled off under reduced pressure to provide 15.08 g (yield: 95%) of the title compound as brown crystal.

$^1$H-NMR(CDCl$_3$)δ: 8.73(bs, 1H), 8.22(d, J=5.5 Hz, 1H), 7.77(d, J=12.9 Hz, 1H), 6.72(dd, J=5.5 Hz, 12.9 Hz, 1H), 5.00(d, J=12.9 Hz, 1H), 2.96(s, 6H).

b: Synthesis of 4-pyrimidinylacetonitrile

To 70 mL of an aqueous solution containing 5 g of dimethyl-[(E)-2-(4-pyrimidinyl)vinyl]amine, 9.48 g of hydroxylamine-O-sulfonic acid was added and stirred at 50° C. for 30 minutes. The reaction solution was made basic by addition of saturated aqueous hydrogen-carbonate solution under cooling with ice, and extracted with ethyl acetate. The ethyl acetate extract was dried over anhydrous magnesium sulfate and removed of the solvent by distillation under reduced pressure. Thus obtained residue was purified on 30 g silica gel column chromatography (eluent, chloroform:methanol=30:1) to provide 1.56 g (yield: 39%) of the title compound as pale yellow crystal.

$^1$H-NMR(CDCl$_3$)δ: 9.21(d, J=1.2 Hz, 1H), 8.80(d, J=5.2 Hz, 1H), 7.51(dd, J=1.2 Hz, 5.2 Hz, 1H), 3.93(s, 2H).

c: Synthesis of 5-amino-3-(4-fluorophenyl)-4-(4-pyrimidinyl)-isoxazole

Sodium methoxide 2.50 g was dissolved in 50 mL of methanol, into which 50 mL of a THF solution containing 5 g of 4-pyrimidinylacetonitrile was dropped, followed by 30 minutes' stirring at room temperature. Then 50 mL of a methanol solution containing 7.29 g of 4-fluorobenzhydroxymoyl chloride was dropped into the solution and stirred at room temperature for 7 hours. After removing the solvent from the reaction solution by distillation under reduced pressure, water was added to the system and the precipitated residue was recovered by filtration, washed with water and dried under reduced pressure. Thus obtained residue was purified on 80 g silica gel column chromatography (eluent, chloroform:methanol=50:1-30:1) and washed with ether to provide 7.86 g of the title compound (yield: 73%) as light gray crystal.

$^1$H-NMR(CDCl$_3$)δ: 9.03(d, J=1.4 Hz, 1H), 8.32(d, J=5.6 Hz, 1H), 7.54-7.49(m, 2H), 7.24-7.18(m, 2H), 6.88(bs, 2H), 6.70(dd, J=1.4 Hz, 5.6 Hz, 1H)

Mass, m/e: 256(M$^+$), 111(base)..

d: Synthesis of 3-(4-fluorophenyl)-5-(phenylacetylamino)-4-(4-pyrimidinyl)isoxazole Imidazole 0.43 g and DBU 1.9 g were dissolved in 40 mL of THF. Under cooling with ice, 0.97 g of phenylacetyl chloride was dropped into the solution, followed by 20 minutes' stirring at room temperature. Then 40 mL of a THF solution containing 0.8 g of 5-amino-3-(4-fluorophenyl)-4-(4-pyrimidinyl)isoxazole was dropped into the system and stirred at room temperature for 6 hours. From the reaction solution the solvent was distilled off under reduced pressure and water was added to the residue, which was then extracted with ethyl acetate. The organic layer was dried over anhydrous magnesium sulfate and from which the solvent was distilled off under reduced pressure. Thus obtained residue was purified on 40 g silica gel column chromatography (eluent, chloroform:methanol=100:1) and washed with ether to provide 0.77 g of the title compound (yield: 66%) in the form of colorless crystal.

$^1$H-NMR(CDCl$_3$)δ: 11.39(s, 1H), 8.49(s, 1H), 8.36(d, J=5.6 Hz, 1H), 7.50-7.38(m, 7H), 7.20(t, J=8.5 Hz, 2H), 6.73(dd, J=1.3 Hz, 5.6 Hz, 1H), 3.94(s, 2H).

Mass, m/e: 374(M$^+$), 240(base).

Example 2

3-(4-Fluorophenyl)-5-[(2-fluorophenyl)acetylamino]-4-(4-pyrimidinyl)isoxazole

To 5 mL of a THF solution containing 0.12 g of 2'-fluorophenylacetic acid, 0.126 g of CDI was added and stirred for an hour at room temperature. Then 0.237 g of DBU and 0.1 g of 5-amino-3-(4-fluorophenyl)-4-(4-pyrimidinyl)isoxazole as dissolved in 5 mL of THF were added, followed by 11 hours' stirring at room temperature. After distilling the solvent off from the reaction solution under reduced pressure, water was added to the residue, followed by extraction with ethyl acetate. The organic layer was dried over anhydrous magnesium sulfate and from which the solvent was distilled off under reduced pressure. The resulting residue was purified on 15 g silica gel column chromatography (eluent, chloroform:methanol=100:1) and washed with ether-hexane to provide 0.090 g (yield: 59%) of the title compound as colorless crystal.

$^1$H-NMR(CDCl$_3$)δ: 11.57(s, 1H), 8.62(s, 1H), 8.39(d, J=5.7 Hz, 1H), 7.50-7.40(m, 4H), 7.30-7.17(m, 4H), 6.76(dd, J=1.6 Hz, 5.7 Hz, 1H), 3.97(s, 2H).

Mass, m/e: 392(M$^+$), 109(base).

The compounds of Examples 3-43 were synthesized in the manner similar to Example 2.

Example 3

3-(4-Fluorophenyl)-5-[(3-fluorophenyl)acetylamino]-4-(4-pyrimidinyl)isoxazole $^1$H-NMR(CDCl$_3$)δ: 11.42(bs, 1H), 8.66(s, 1H), 8.39(d, J=5.4 Hz, 1H), 7.48-7.43(m, 3H), 7.22-7.18(m, 3H), 7.15-7.12(m, 2H), 6.76(dd, J=1.2 Hz, 5.4 Hz, 1H), 3.94(s, 2H).

Mass, m/e: 392(M$^+$), 109(base.)

Example 4

3-(4-Fluorophenyl)-5-[(4-fluorophenyl)acetylamino]-4-(4-pyrimidinyl)isoxazole $^1$H-NMR(CDCl$_3$)δ: 11.40(bs, 1H), 8.65(s, 1H), 8.40(d, J=5.8 Hz, 1H), 7.48-7.44(m, 2H), 7.39-7.36(m, 2H), 7.22-7.13(m, 4H), 6.76(dd, J=1.5 Hz, 5.8 Hz, 1H), 3.91(s, 2H).
Mass, m/e: 392(M$^+$), 109(base).

Example 5

5-[(2-chlorophenyl)acetylamino]-3-(4-fluorophenyl)-4-(4-pyrimidinyl)isoxazole $^1$H-NMR(CDCl$_3$)δ: 11.45(bs, 1H), 8.54(s, 1H), 8.38(d, J=5.7 Hz, 1H), 7.55-7.38(m, 6H), 7.20(t, J=8.7 Hz, 2H), 6.75(dd, J=1.3 Hz, 5.7 Hz, 1H), 4.06(s, 2H).
Mass, m/e: 408(M$^+$), 240(base).

Example 6

5-[(3-Chlorophenyl)acetylamino]-3-(4-fluorophenyl)-4-(4-pyrimidinyl)isoxazole $^1$H-NMR(CDCl$_3$)δ: 11.42(s, 1H), 8.69(s, 1H), 8.40(d, J=5.4 Hz, 1H), 7.50-7.38(m, 5H), 7.29(dt, J=1.9 Hz, 6.6 Hz, 1H), 7.21(t, J=8.7 Hz, 2H), 6.77(dd, J=1.3 Hz, 5.4 Hz, 1H), 3.92(s, 2H).
Mass, m/e: 408(M$^+$), 240(base).

Example 7

5-[(4-Chlorophenyl)acetylamino]-3-(4-fluorophenyl)-4-(4-pyrimidinyl)isoxazole)

$^1$H-NMR(CDCl$_3$)δ: 11.39(s, 1H), 8.65(s, 1H), 8.42(d, J=5.5 Hz, 1H), 7.50-7.42(m, 4H), 7.35(d, J=8.6 Hz, 2H), 7.21(t, J=8.6 Hz, 2H), 6.77(dd, J=1.4 Hz, 5.5 Hz, 1H), 3.92(s, 2H).
Mass, m/e: 408(M$^+$), 240(base).

Example 8

5-[(2-Bromophenyl)acetylamino]-3-(4-fluorophenyl)-4-(4-pyrimidinyl)isoxazole $^1$H-NMR(CDCl$_3$)δ: 11.42(s, 1H), 8.53(s, 1H), 8.38(d, J=5.5 Hz, 1H), 7.72(dd, J=1.2 Hz, 7.7 Hz, 1H), 7.50-7.43(m, 4H), 7.37-7.31(m, 1H), 7.20(t, J=8.7 Hz, 2H), 6.75(dd, J=1.3 Hz, 5.5 Hz, 1H), 4.09(s, 2H).
Mass, m/e: 454(M$^+$), 240(base).

Example 9

5-[(2-Iodophenyl)acetylamino]-3-(4-fluorophenyl)-4-(4-pyrimidinyl)isoxazole $^1$H-NMR(CDCl$_3$)δ: 11.38(s, 1H), 8.51(s, 1H), 8.38(d, J=5.5 Hz, 1H), 8.00(d, J=7.7 Hz, 1H), 7.52-7.43(m, 4H), 7.24-7.13(m, 3H), 6.75(dd, J=1.3 Hz, 5.5 Hz, 1H), 4.10(s, 2H)
Mass, m/e: 500(M$^+$), 240(base). .

Example 10

3-(4-Fluorophenyl)-5-[(2,5-difluorophenyl)acetylamino]-4-(4-pyrimidinyl)isoxazole $^1$H-NMR(CDCl$_3$)δ: 11.62(bs, 1H), 8.80(s, 1H), 8.43(d, J=5.6 Hz, 1H), 7.50-7.46(m, 2H), 7.23-7.06(m, 5H), 6.79(dd, J=1.5 Hz, 5.6 Hz, 1H), 3.94(s, 2H).
Mass, m/e: 410(M$^+$), 240(base).

Example 11

5-[(2,6-Difluorophenyl)acetylamino]-3-(4-fluorophenyl)-4-(4-pyrimidinyl)isoxazole $^1$H-NMR(CDCl$_3$)δ: 11.65(s, 1H), 8.70(s, 1H), 8.41(d, J=5.4 Hz, 1H), 7.48(dd, J=5.2 Hz, 8.6 Hz, 2H), 7.45-7.36(m, 1H), 7.21(t, J=8.6 Hz, 2H), 7.04(t, J=7.7 Hz, 2H), 6.79(dd, J=1.3 Hz, 5.4 Hz, 1H), 4.02(s, 2H).
Mass, m/e: 410(M$^+$), 240(base).

Example 12

5-[(2-Chloro-4-fluorophenyl)acetylamino]-3-(4-fluorophenyl)-4-(4-pyrimidinyl)isoxazole $^1$H-NMR(CDCl$_3$)δ: 11.48(s, 1H), 8.72(s, 1H), 8.42(d, J=5.4 Hz, 1H), 7.51-7.43(m, 4H), 7.30-7.18(m, 2H), 7.12(dt, J=2.7 Hz, 8.1 Hz, 1H), 6.79(dd, J=1.5 Hz, 5.4 Hz, 1H), 4.04(s, 2H).
Mass, m/e: 426(M$^+$), 240(base).

Example 13

5-[(2-Chloro-6-fluorophenyl)acetylamino]-3-(4-fluorophenyl)-4-(4-pyrimidinyl)isoxazole $^1$H-NMR(CDCl$_3$)δ: 11.55(s, 1H), 8.64(s, 1H), 8.40(d, J=5.7 Hz, 1H), 7.51-7.45(m, 2H), 7.43-7.34(m, 2H), 7.26-7.13(m, 3H), 6.78(dd, J=1.3 Hz, 5.7 Hz, 1H), 4.14(s, 2H).
Mass, m/e: 426(M$^+$), 240(base).

Example 14

5-[(2,4-Dichlorophenyl)acetylamino]-3-(4-fluorophenyl)-4-(4-pyrimidinyl)isoxazole $^1$H-NMR(CDCl$_3$)δ: 11.47(s, 1H), 8.71(s, 1H), 8.42(d, J=5.6 Hz, 1H), 7.54(d, J=1.9 Hz, 1H), 7.48(dd, J=5.4 Hz, 8.9 Hz, 2H), 7.43-7.35(m, 2H), 7.21(t, J=8.9 Hz, 2H), 6.79(dd, J=5.6 Hz, 1H), 4.04(s, 2H).
Mass, m/e: 442(M$^+$), 240(base).

Example 15

5-[(3,4-dichlorophenyl)acetylamino]-3-(4-fluorophenyl)-4-(4-pyrimidinyl)isoxazole $^1$H-NMR(CDCl$_3$)δ: 11.44(s, 1H), 8.78(s, 1H), 8.43(d, J=5.7 Hz, 1H), 7.54-7.51(m, 2H), 7.48(dd, J=5.2 Hz, 8.7 Hz, 2H), 7.27-7.19(m, 3H), 6.79(dd, J=1.4 Hz, 5.7 Hz, 1H), 3.91(s, 2H).
Mass, m/e: 442(M$^+$), 240(base).

Example 16

5-[(2,6-Dichlorophenyl)acetylamino]-3-(4-fluorophenyl)-4-(4-pyrimidinyl)isoxazole $^1$H-NMR(CDCl$_3$)δ: 11.49(s, 1H), 8.62(s, 1H), 8.41(d, J=5.6 Hz, 1H), 7.49(t, J=7.5 Hz, 4H), 7.37(dd, J=7.3 Hz, 8.5 Hz, 1H), 7.23(t, J=8.5 Hz, 2H), 6.79(dd, J=1.5 Hz, 5.6 Hz, 1H), 4.33(s, 2H).
Mass, m/e: 442(M$^+$), 240(base).

Example 17

3-(4-Fluorophenyl)-5-[(2-methoxyphenyl)acetylamino]-4-(4-pyrimidinyl)isoxazole $^1$H-NMR(CDCl$_3$)δ: 11.34(s, 1H), 8.46(s, 1H), 8.35(d, J=5.5 Hz, 1H), 7.49-7.42(m, 3H), 7.34(dd, J=1.7 Hz, 7.5 Hz, 1H), 7.19(t, J=8.6 Hz, 2H), 7.09(dt, J=1.0 Hz, 7.5 Hz, 1H), 6.99(d, J=8.6 Hz, 1H), 6.72(dd, J=1.3 Hz, 5.5 Hz, 1H), 3.88(s, 2H), 3.81(s, 3H).
Mass, m/e: 404(M$^+$), 148(base).

Example 18

5-[(3-Methoxyphenyl)acetylamino]-3-(4-fluorophenyl)-4-(4-pyrimidinyl)isoxazole $^1$H-NMR(CDCl$_3$)δ: 11.41(s, 1H), 8.60(d, J=1.3 Hz, 1H), 8.37(d, J=5.5 Hz, 1H), 7.49-7.43(m, 2H), 7.40(t, J=7.9 Hz, 1H), 7.20(t, J=8.7 Hz, 2H), 7.00-6.93(m, 3H), 6.73(dd, J=1.3 Hz, 5.5 Hz, 1H), 3.90(s, 2H), 3.84(s, 3H).
Mass, m/e: 404(M$^+$), 240(base).

Example 19

5-[(4-Methoxyphenyl)acetylamino]-3-(4-fluorophenyl)-4-(4-pyrimidinyl)isoxazole $^1$H-NMR(CDCl$_3$)δ: 11.38(s, 1H), 8.57(d, J=1.3 Hz, 1H), 8.37(d, J=5.5 Hz, 1H), 7.49-7.43(m, 2H), 7.31(d, J=8.8 Hz, 2H), 7.20(t, J=8.8 Hz, 2H), 7.00(d, J=8.8 Hz, 2H), 6.74(dd, J=1.3 Hz, 5.5 Hz, 1H), 3.87(s, 2H), 3.86(s, 3H).
Mass, m/e: 404(M$^+$), 148(base).

Example 20

5-[(2-Ethoxyphenyl)acetylamino]-3-(4-fluorophenyl)-4-(4-pyrimidinyl)isoxazole $^1$H-NMR(CDCl$_3$)δ: 11.33(bs, 1H), 8.43(d, J=1.5 Hz, 1H), 8.34(d, J=5.8 Hz, 1H), 7.48-7.40(m, 3H), 7.34(dd, J=1.5 Hz, 7.3 Hz, 1H), 7.22-7.16(m, 2H), 7.07(dt, J=1.2 Hz, 7.7 Hz, 1H), 6.97(d, J=7.7 Hz, 1H), 6.71(dd, J=1.5 Hz, 5.8 Hz, 1H), 4.03(q, J=6.9 Hz, 2H), 3.88(s, 2H), 1.32(t, J=6.9 Hz, 3H).
Mass, m/e: 418(M$^+$), 240(base).

Example 21

5-[(3-Ethoxyphenyl)acetylamino]-3-(4-fluorophenyl)-4-(4-pyrimidinyl)isoxazole $^1$H-NMR(CDCl$_3$)δ: 11.41(bs, 1H), 8.61(d, J=1.3 Hz, 1H), 8.37(d, J=5.6 Hz, 1H), 7.48-7.43(m, 2H), 7.27(t, J=8.1 Hz, 1H), 7.22-7.16(m, 2H), 6.97-6.92(m, 3H), 6.73(dd, J=1.3 Hz, 5.6 Hz, 1H), 4.05(q, J=7.3 Hz, 2H), 3.88(s, 2H), 1.41(t, J=7.3 Hz, 3H)
Mass, m/e: 418(M$^+$), 162(base).

Example 22

3-(4-Fluorophenyl)-5-[(2-propoxyphenyl)acetylamino]-4-(4-pyrimidinyl)isoxazole $^1$H-NMR(CDCl$_3$)δ: 11.33(bs, 1H), 8.42(d, J=1.3 Hz, 1H), 8.34(d, J=5.8 Hz, 1H), 7.47-7.41(m, 3H), 7.34(dd, J=1.5 Hz, 7.3 Hz, 1H), 7.21-7.16(m, 2H), 7.07(dt, J=0.8 Hz, 7.3 Hz, 1H), 6.97(d, J=8.1 Hz, 1H), 6.71(dd, J=1.3 Hz, 5.8 Hz, 1H), 3.92-3.88(m, 4H), 3.88(s, 2H), 1.72(dt, J=7.3 Hz, 13.8 Hz, 2H), 0.92(t, J=7.3 Hz, 3H).
Mass, m/e: 432(M$^+$), 107(base).

Example 23

3-(4-Fluorophenyl)-5-[(3-propoxyphenyl)acetylamino]-4-(4-pyrimidinyl)isoxazole $^1$H-NMR(CDCl$_3$)δ: 11.42(bs, 1H), 8.61(d, J=1.2 Hz, 1H), 8.37(d, J=5.6 Hz, 1H), 7.47-7.44(m, 2H), 7.37(t, J=8.1 Hz, 1H), 7.21-7.17(m, 2H), 6.98-6.94(m, 3H), 6.73(dd, J=1.2 Hz, 5.6 Hz, 1H), 3.94(t, J=6.6 Hz, 2H), 3.88(s, 2H), 1.85-1.76(m, 2H), 1.02(t, J=7.3 Hz, 3H).
Mass, m/e: 432(M$^+$), 240(base).

Example 24

3-(4-Fluorophenyl)-5-[(2-isopropoxyphenyl)acetylamino]-4-(4-pyrimidinyl)isoxazole $^1$H-NMR(CDCl$_3$)δ: 11.31(bs, 1H), 8.39(d, J=1.0 Hz, 1H), 8.34(d, J=5.6 Hz, 1H), 7.48-7.40(m, 3H), 7.33(dd, J=1.5 Hz, 7.7 Hz, 1H), 7.20-7.16(m, 2H), 7.02(t, J=7.3 Hz, 1H), 6.97(d, J=8.5 Hz, 1H), 6.70(dd, J=1.0 Hz, 5.6 Hz, 1H), 4.55(m, J=6.2 Hz, 1H), 3.85(s, 2H), 1.24(d, J=6.2 Hz, 6H).
Mass, m/e: 432(M$^+$), 134(base).

Example 25

3-(4-Fluorophenyl)-5-[(3-isopropoxyphenyl)acetylamino]-4-(4-pyrimidinyl)isoxazole $^1$H-NMR(CDCl$_3$)δ: 11.43(bs, 1H), 8.63(d, J=1.4 Hz, 1H), 8.37(d, J=5.4 Hz, 1H), 7.48-7.43(m, 2H), 7.36(t, J=8.1 Hz, 1H), 7.22-7.16(m, 2H), 6.96-6.92(m, 3H), 6.72(dd, J=1.4 Hz, 5.4 Hz, 1H), 4.58(m, J=5.8 Hz, 1H), 3.87(s, 2H), 1.33(d, J=5.8 Hz, 6H).
Mass, m/e: 432(M$^+$), 240(base).

Example 26

5-[(2,3-Dimethoxyphenyl)acetylamino]-3-(4-fluorophenyl)-4-(4-pyrimidinyl)isoxazole $^1$H-NMR(CDCl$_3$)δ: 11.47(s, 1H), 8.62(d, J=1.4 Hz, 1H), 8.36(d, J=5.5 Hz, 1H), 7.49-7.43(m, 2H), 7.23-7.16(m, 2H), 7.14(d, J=7.7 Hz, 1H), 7.00(dd, J=1.4 Hz, 8.3 Hz, 1H), 6.95(dd, J=1.4 Hz, 7.7 Hz, 1H), 6.72(dd, J=1.4 Hz, 5.5 Hz, 1H), 3.90(s, 3H), 3.89(s, 3H).
Mass, m/e: 434(M$^+$), 178(base).

Example 27

5-[(2,5-Dimethoxyphenyl)acetylamino]-3-(4-fluorophenyl)-4-(4-pyrimidinyl)isoxazole $^1$H-NMR(CDCl$_3$)δ: 11.35(s, 1H), 8.58(d, J=1.3 Hz, 1H), 8.36(d, J=5.5 Hz, 1H), 7.46(dd, J=5.2 Hz, 8.7 Hz, 2H), 7.19(t, J=8.7 Hz, 2H), 6.97-6.89(m, 3H), 6.73(dd, J=1.3 Hz, 5.5 Hz, 1H), 3.86(s, 2H), 3.81(s, 3H), 3.77(s, 3H).
Mass, m/e: 434(M$^+$), 178(base).

Example 28

5-[(3,5-Dimethoxyphenyl)acetylamino]-3-(4-fluorophenyl)-4-(4-pyrimidinyl)isoxazole $^1$H-NMR(CDCl$_3$)δ: 11.45(s, 1H), 8.70(d, J=1.3 Hz, 1H), 8.38(d, J=5.7 Hz, 1H), 7.49-7.43(m, 2H), 7.23-7.17(m, 2H), 6.74(dd, J=1.3 Hz, 5.7 Hz, 1H), 6.54(d, J=2.2 Hz, 2H), 6.51(t, J=2.2 Hz, 1H), 3.84(s, 2H), 3.81(s, 6H).
Mass, m/e: 434(M$^+$), 178(base).

Example 29

3-(4-Fluorophenyl)-4-(4-pyrimidinyl)-5-[(3,4,5-trimethoxyphenyl)-acetylamino]isoxazole $^1$H-NMR(CDCl$_3$)δ: 11.38(s, 1H), 8.71(s, 1H), 8.40(d, J=5.5 Hz, 1H), 7.50-7.44(m, 2H), 7.24-7.17(m, 2H), 6.75(dd, J=1.0 Hz, 5.5 Hz, 1H), 6.60(s, 2H), 3.89(s, 2H), 3.87(s, 6H), 3.86(s, 3H).
Mass, m/e: 464(M$^+$), 208(base).

Example 30

3-(4-Fluorophenyl)-5-[(2-methylphenyl)acetylamino]-4-(4-pyrimidinyl)isoxazole $^1$H-NMR(CDCl$_3$)δ: 11.35(s, 1H), 8.42(s, 1H), 8.35(d, J=5.5 Hz, 1H), 7.48-7.30(m, 6H), 7.19(t, J=8.7 Hz, 2H), 6.71(dd, J=1.3 Hz, 5.5 Hz, 1H), 3.92(s, 2H), 2.36(s, 3H).
Mass, m/e: 388(M$^+$), 240(base).

Example 31

3-(4-Fluorophenyl)-5-[(3-methylphenyl)acetylamino]-4-(4-pyrimidinyl)isoxazole $^1$H-NMR(CDCl$_3$)δ: 11.37(bs, 1H), 8.48(s, 1H), 8.36(d, J=5.4 Hz, 1H), 7.45(dd, J=5.4 Hz, 8.5 Hz, 2H), 7.37(t, J=7.7 Hz, 1H), 7.27(s, 1H), 7.21-7.17(m, 4H), 6.73(dd, J=1.2 Hz, 5.4 Hz, 1H), 3.88(s, 2H), 2.39(s, 3H).
Mass, m/e: 388(M$^+$), 240(base).

Example 32

5-[(2,5-Dimethylphenyl)acetylamino]-3-(4-fluorophenyl)-4-(4-pyrimidinyl)isoxazole $^1$H-NMR(CDCl$_3$)δ: 11.32(s, 1H), 8.39(d, J=1.4 Hz, 1H), 8.35(d, J=5.4 Hz, 1H), 7.49-7.43(m, 2H), 7.23-7.14(m, 5H), 6.72(dd, J=1.4 Hz, 5.4 Hz, 1H), 3.88(s, 2H), 2.39(s, 3H), 2.31(s, 3H).
Mass, m/e: 402(M$^+$), 240(base).

Example 33

5-[(3,5-Dimethylphenyl)acetylamino]-3-(4-fluorophenyl)-4-(4-pyrimidinyl)isoxazole $^1$H-NMR(CDCl$_3$)δ: 11.36(s, 1H), 8.46(s, 1H), 8.36(d, J=5.7 Hz, 1H), 7.49-7.43(m, 2H), 7.20(t, J=8.7 Hz, 2H), 7.08(s, 1H), 7.00(s, 2H), 6.73(dd, J=1.3 Hz, 5.7 Hz, 1H), 3.84(s, 2H), 2.35(s, 6H)
Mass, m/e: 402(M$^+$), 283(base).

Example 34

3-(4-Fluorophenyl)-5-[(2-nitrophenyl)acetylamino]-4-(4-pyrimidinyl)isoxazole $^1$H-NMR(CDCl$_3$)δ: 11.67(s, 1H), 8.89(bs, 1H), 8.89(s, 1H), 8.44(d, J=5.4 Hz, 1H), 8.20(d, J=8.5 Hz, 1H), 7.72(dt, J=1.5 Hz, 7.7 Hz, 1H), 7.59(t, J=7.7 Hz, 2H), 7.53-7.47(m, 2H), 7.22(t, J=8.7 Hz, 1H), 6.80(dd, J=1.5 Hz, 5.4 Hz, 1H), 4.31(s, 2H).
Mass, m/e: 419(M$^+$), 240(base).

Example 35

3-(4-Fluorophenyl)-5-[(4-nitrophenyl)acetylamino]-4-(4-pyrimidinyl)isoxazole $^1$H-NMR(CDCl$_3$)δ: 11.57(s, 1H), 8.88(s, 1H), 8.45(d, J=5.5 Hz, 1H), 8.29(d, J=8.9 Hz, 2H), 7.59(d, J=8.9 Hz, 2H), 7.52-7.46(m, 2H), 7.25-7.20(m, 2H), 6.82(dd, J=1.3 Hz, 5.5 Hz, 1H), 4.10(s, 2H).
Mass, m/e: 419(M$^+$), 240(base).

Example 36

3-(4-Fluorophenyl)-4-(4-pyrimidinyl)-5-[(2-trifluoromethylphenyl)acetylamino]isoxazole $^1$H-NMR(CDCl$_3$)δ: 11.38(s, 1H), 8.58(s, 1H), 8.39(d, J=5.7 Hz, 1H), 7.82(d, J=8.1 Hz, 1H), 7.67(t, J=7.3 Hz, 1H), 7.61-7.53(m, 2H), 7.50-7.44(m, 2H), 7.20(t, J=8.7 Hz, 2H), 6.76(dd, J=1.4 Hz, 5.7 Hz, 1H), 4.12(s, 2H).
Mass, m/e: 442(M$^+$), 240(base).

Example 37

3-(4-Fluorophenyl)-4-(4-pyrimidinyl)-5-[(3-trifluoromethylthiophenyl)acetylamino]isoxazole $^1$H-NMR(CDCl$_3$)δ: 11.47(s, 1H), 8.64(s, 1H), 8.41(d, J=5.5 Hz, 1H), 7.74-7.68(m, 2H), 7.57-7.45(m, 4H), 7.25-7.18(m, 2H), 6.78(dd, J=1.3 Hz, 5.5 Hz, 1H), 3.99(s, 2H).
Mass, m/e: 474(M$^+$), 240(base).

Example 38

3-(4-Fluorophenyl)-5-(2-phenylpropionylamino)-4-(4-pyrimidinyl)isoxazole $^1$H-NMR(CDCl$_3$)δ: 11.40(bs, 1H), 8.57(d, J=1.4 Hz, 1H), 8.35(d, J=5.6 Hz, 1H), 7.50-7.38(m, 7H), 7.19(t, J=8.7 Hz, 2H), 6.72(dd, J=1.4 Hz, 5.6 Hz, 1H), 3.93(q, J=7.3 Hz, 1H), 1.68(d, J=7.3 Hz, 3H).
Mass, m/e: 388(M$^+$), 240(base).

Example 39

3-(4-Fluorophenyl)-5-(2-methyl-2-phenylpropionylamino)-4-(4-pyrimidinyl)isoxazole $^1$H-NMR(CDCl$_3$)δ: 11.32(s, 1H), 8.43(d, J=1.4 Hz, 1H), 8.33(d, J=5.4 Hz, 1H), 7.52-7.42(m, 6H), 7.41-7.36(m, 1H), 7.19(t, J=8.7 Hz, 2H), 6.70(dd, J=1.4 Hz, 5.4 Hz, 1H), 1.74(s, 6H)
Mass, m/e: 402(M$^+$), 240(base).

Example 40

3-(4-Fluorophenyl)-5-[2-(4-isobutylphenyl)propionylamino]-4-(4-pyrimidinyl)isoxazole ¹H-NMR(CDCl₃)δ: 11.42(s, 1H), 8.62(d, J=1.4 Hz, 1H), 8.36(d, J=5.4 Hz, 1H), 7.46(dd, J=5.4 Hz, 8.9 Hz, 2H), 7.31 (d, J=8.3 Hz, 2H), 7.22(d, J=8.3 Hz, 2H), 7.18(d, J=8.9 Hz, 2H), 6.72(dd, J=1.4 Hz, 5.4 Hz, 1H), 3.89(q, J=7.1 Hz, 1H), 2.51(d, J=7.3 Hz, 2H), 1.94-1.82(m, 1H), 1.66(d, J=7.1 Hz, 3H), 0.89(dd, J=3.9 Hz, 6.6 Hz, 6H).
Mass, m/e: 444(M⁺), 240(base).

Example 41

3-(4-Fluorophenyl)-4-(4-pyrimidinyl)-5-[(2-thienyl)acetylamino]-isoxazole

¹H-NMR(CDCl₃)δ: 11.62(bs, 1H), 8.68(s, 1H), 8.39(d, J=5.6 Hz, 1H), 7.47(dd, J=5.4 Hz, 8.9 Hz, 2H), 7.42(dd, J=1.5 Hz, 5.0 Hz, 1H), 7.22-7.14(m, 4H), 6.76(dd, J=1.5 Hz, 5.6 Hz, 1H), 4.13(s, 2H).
Mass, m/e: 380(M⁺), 240(base).

Example 42

3-(4-Fluorophenyl)-5-{[5-(3-methylisoxazoyl)]acetylamino}-4-(4-pyrimidinyl)isoxazole ¹H-NMR(CDCl₃)δ: 11.96(bs, 1H), 9.13(d, J=1.4 Hz, 1H), 8.46(d, J=5.6 Hz, 1H), 7.49(dd, J=5.4 Hz, 8.9 Hz, 2H), 7.22(t, J=8.9 Hz, 2H), 6.81(dd, J=1.4 Hz, 5.6 Hz, 1H), 6.21(s, 1H), 4.09(s, 2H), 2.35(s, 3H).
Mass, m/e: 379(M⁺), 240(base).

Example 43

3-(4-Fluorophenyl)-4-(4-pyrimidinyl)-5-[(3-thienyl)acetylamino]-isoxazole

¹H-NMR(CDCl₃)δ: 11.44(s, 1H), 8.75(s, 1H), 8.40(d, J=5.4 Hz, 1H), 7.50-7.44(m, 3H), 7.37-7.35(m, 1H), 7.20(t, J=8.5 Hz, 2H), 7.13(d, J=5.0 Hz, 1H), 6.76(dd, J=1.2 Hz, 5.4 Hz, 1H), 3.97(s, 2H).
Mass, m/e: 380(M⁺), 240(base).

In the following, the compounds of Examples 44-299 were synthesized in the manner similar to Examples 1 and 2.

Example 44

3-Phenyl-5-(phenylacetylamino)-4-(4-pyrimidinyl)isoxazole a: 5-Amino-3-phenyl-4-(4-pyrimidinyl)isoxazole ¹H-NMR(DMSO-d₆)δ: 8.99(d, J=1.4 Hz, 1H), 8.35(d, J=5.4 Hz, 1H), 8.29(bs, 2H), 7.59-7.50(m, 5H), 6.56(dd, J=1.4 Hz, 5.4 Hz, 1H).
Mass, m/e: 238(M⁺), 77(base).

b: 3-Phenyl-5-(phenylacetylamino)-4-(4-pyrimidinyl)isoxazole

¹H-NMR(CDCl₃)δ: 11.42(bs, 1H), 8.48(s, 1H), 8.32(d, J=5.6 Hz, 1H), 7.53-7.39(m, 10H), 6.73(dd, J=1.5 Hz, 5.6 Hz, 1H), 3.94(s, 2H)
Mass, m/e: 356(M⁺), 222(base)..

Example 45

5-[2-(Chlorophenyl)acetylamino]-3-phenyl-4-(4-pyrimidinyl)isoxazole

¹H-NMR(CDCl₃)δ: 11.47(bs, 1H), 8.52(s, 1H), 8.34(d, J=5.4 Hz, 1H), 7.54-7.39(m, 9H), 6.75(dd, J=0.8 Hz, 5.4 Hz, 1H), 4.06(s, 2H).
Mass, m/e: 390(M⁺), 222(base).

Example 46

5-[(2,6-Dichlorophenyl)acetylamino]-3-phenyl-4-(4-pyrimidinyl)-isoxazole

¹H-NMR(CDCl₃)δ: 11.50(bs, 1H), 8.59(s, 1H), 8.36(d, J=5.4 Hz, 1H), 7.55-7.46(m, 7H), 7.35(dd, J=7.3 Hz, 8.5 Hz, 1H), 6.79(dd, J=1.6 Hz, 5.4 Hz, 1H), 4.32(s, 2H).
Mass, m/e: 424(M⁺), 222(base).

Example 47

5-[(3-Methylphenyl)acetylamino]-3-phenyl-4-(4-pyrimidinyl)isoxazole

¹H-NMR(CDCl₃)δ: 11.41(s, 1H), 8.47(s, 1H), 8.33(d, J=5.4 Hz, 1H), 7.56-7.44(m, 5H), 7.40-7.36(m, 1H), 7.28-7.18(m, 3H), 6.74(dd, J=1.5 Hz, 5.4 Hz, 1H), 3.90(s, 2H), 2.40(s, 3H).
Mass, m/e: 370(M⁺), 77(base).

Example 48

5-[(2,5-Dimethylphenyl)acetylamino]-3-phenyl-4-(4-pyrimidinyl)-isoxazole

¹H-NMR(CDCl₃)δ: 11.35(s, 1H), 8.37(d, J=1.4 Hz, 1H), 8.33(d, J=5.4 Hz, 1H), 7.56-7.44(m, 5H), 7.40-7.36(m, 1H), 7.21-7.16(m, 2H), 6.74(dd, J=1.4 Hz, 5.4 Hz, 1H), 3.88(s, 2H), 2.39(s, 3H), 2.31(s, 3H).
Mass, m/e: 384(M⁺), 222(base).

Example 49

3-(3-Fluorophenyl)-5-(phenylacetylamino)-4-(4-pyrimidinyl)isoxazole a: 5-Amino-3-(3-fluorophenyl)-4-(4-pyrimidinyl)isoxazole ¹H-NMR(CDCl₃)δ: 9.03(d, J=1.5 Hz, 1H), 8.33(d, J=5.7 Hz, 1H), 7.53-7.46(m, 1H), 7.31(dt, J=1.3 Hz, 8.1 Hz, 1H), 7.28-7.21(m, 3H), 6.92-6.82(bs, 2H), 6.71(dd, J=1.5 Hz, 5.7 Hz, 1H).
Mass, m/e: 256(M⁺), 111(base).

b: 3-(3-Fluorophenyl)-5-(phenylacetylamino)-4-(4-pyrimidinyl)-isoxazole

¹H-NMR(CDCl₃)δ: 11.40(s, 1H), 8.52-8.47(bs, 1H), 8.37 (d, J=5.4 Hz, 1H), 7.52-7.39(m, 6H), 7.28-7.17(m, 3H), 6.74 (dd, J=1.5 Hz, 5.4 Hz, 1H), 3.94(s, 2H).
Mass, m/e: 374(M⁺), 91(base).

Example 50

3-(3-Fluorophenyl)-5-[(2-fluorophenyl)acetylamino]-4-(4-pyrimidinyl)-isoxazole $^1$H-NMR(CDCl$_3$)δ: 11.58(s, 1H), 8.62(s, 1H), 8.40(d, J=5.5 Hz, 1H), 7.52-7.39(m, 3H), 7.29-7.17(m, 5H), 6.77(dd, J=1.3 Hz, 5.5 Hz, 1H), 3.97(s, 2H).

Mass, m/e: 392(M$^+$), 109(base).

Example 51

5-[(2-Chlorophenyl)acetylamino]-3-(3-fluorophenyl)-4-(4-pyrimidinyl)-isoxazole $^1$H-NMR(CDCl$_3$)δ: 11.46(s, 1H), 8.57-8.52(bs, 1H), 8.39 (d, J=5.5 Hz, 1H), 7.55-7.38(m, 5H), 7.28-7.18(m, 3H), 6.76 (dd, J=1.3 Hz, 5.5 Hz, 1H), 4.07(s, 2H).

Mass, m/e: 408(M$^+$), 240(base).

Example 52

3-(2-Chlorophenyl)-5-(phenylacetylamino)-4-(4-pyrimidinyl)isoxazole a: 5-Amino-3-(2-chlorophenyl)-4-(4-pyrimidinyl)isoxazole $^1$H-NMR(CDCl$_3$)δ: 9.00(d, J=1.3 Hz, 1H), 8.29(d, J=5.6 Hz, 1H), 7.58-7.40(m, 4H), 6.92(bs, 2H), 6.41(dd, J=1.3 Hz, 5.6 Hz, 1H).

Mass, m/e: 272(M$^+$), 237(base).

b: 3-(2-Chlorophenyl)-5-(phenylacetylamino)-4-(4-pyrimidinyl)-isoxazole $^1$H-NMR(CDCl$_3$)δ: 11.50(s, 1H), 8.47(bs, 1H), 8.33(d, J=5.7 Hz, 1H), 7.55-7.40(m, 9H), 6.46(dd, J=1.3 Hz, 5.7 Hz, 1H), 3.95(s, 2H).

Mass, m/e: 390(M$^+$), 91(base).

Example 53

3-(2-Chlorophenyl)-5-[(2-fluorophenyl)acetylamino]-4-(4-pyrimidinyl)isoxazole $^1$H-NMR(CDCl$_3$)δ: 11.67(s, 1H), 8.59(s, 1H), 8.36(d, J=5.7 Hz, 1H), 7.56-7.40(m, 5H), 7.29-7.18(m, 3H), 6.49(dd, J=1.3 Hz, 5.7 Hz, 1H), 3.98(s, 2H).

Mass, m/e: 408(M$^+$), 109(base).

Example 54

3-(2-Chlorophenyl)-5-[(2-chlorophenyl)acetylamino]-4-(4-pyrimidinyl)isoxazole $^1$H-NMR(CDCl$_3$)δ: 11.55(s, 1H), 8.52(s, 1H), 8.35(d, J=5.5 Hz, 1H), 7.56-7.38(m, 8H), 6.49(dd, J=1.3 Hz, 5.5 Hz, 1H), 4.08(s, 2H)

Mass, m/e: 424(M$^+$), 256(base).

Example 55

3-(3-Chlorophenyl)-5-(phenylacetylamino)-4-(4-pyrimidinyl)isoxazole a: 5-Amino-3-(3-chlorophenyl)-4-(4-pyrimidinyl)isoxazole $^1$H-NMR(CDCl$_3$)δ: 9.03(d, J=1.3 Hz, 1H), 8.34(d, J=5.5 Hz, 1H), 7.56-7.50(m, 2H), 7.45(t, J=7.5 Hz, 1H), 7.41(dt, J=1.5 Hz, 7.5 Hz, 1H), 6.88(bs, 2H), 6.69(dd, J=1.3 Hz, 5.5 Hz, 1H).

Mass, m/e: 272(M$^+$), 127(base).

b: 3-(3-Chlorophenyl)-5-(phenylacetylamino)-4-(4-pyrimidinyl)-isoxazole $^1$H-NMR(CDCl$_3$)δ: 11.40(s, 1H), 8.50(bs, 1H), 8.38(d, J=5.7 Hz, 1H), 7.55-7.32(m, 9H), 6.73(dd, J=1.5 Hz, 5.7 Hz, 1H), 3.94(s, 2H).

Mass, m/e: 390(M$^+$), 91(base).

Example 56

3-(3-Chlorophenyl)-5-[(2-fluorophenyl)acetylamino]-4-(4-pyrimidinyl)-Isoxazole $^1$H-NMR(CDCl$_3$)δ: 11.59(s, 1H), 8.62(bs, 1H), 8.41(d, J=5.5 Hz, 1H), 7.55-7.34(m, 6H), 7.29-7.17(m, 2H), 6.76(dd, J=1.3 Hz, 5.5 Hz, 1H), 3.97(s, 2H).

Mass, m/e: 408(M$^+$), 256(base).

Example 57

3-(3-Chlorophenyl)-5-[(2-chlorophenyl)acetylamino]-4-(4-pyrimidinyl)-isoxazole $^1$H-NMR(CDCl$_3$)δ: 11.46(s, 1H), 8.55(bs, 1H), 8.40(d, J=5.5 Hz, 1H), 7.56-7.33(m, 8H), 6.75(dd, J=1.3 Hz, 5.5 Hz, 1H), 4.07(s, 2H).

Mass, m/e: 424(M$^+$), 256(base).

Example 58

3-(4-Chlorophenyl)-5-(phenylacetylamino)-4-(4-pyrimidinyl)isoxazole a: 5-Amino-3-(4-chlorophenyl)-4-(4-pyrimidinyl)-isoxazole $^1$H-NMR(CDCl$_3$)δ: 9.02(d, J=1.2 Hz, 1H), 8.32(d, J=5.4 Hz, 1H), 7.51-7.45(m, 4H), 6.88(s, 2H), 6.70(dd, J=1.2 Hz, 5.4 Hz, 1H).

Mass, m/e: 272(M$^+$), 127(base).

b: 3-(4-Chlorophenyl)-5-(phenylacetylamino)-4-(4-pyrimidinyl)-isoxazole $^1$H-NMR(CDCl$_3$)δ: 11.38(bs, 1H), 8.49(s, 1H), 8.37(d, J=5.6 Hz, 1H), 7.51-7.39(m, 9H), 6.73(dd, J=1.5 Hz, 5.6 Hz, 1H), 3.93(s, 2H)

Mass, m/e: 390(M$^+$), 91(base).

Example 59

3-(4-Chlorophenyl)-5-[(2-fluorophenyl)acetylamino]-4-(4-pyrimidinyl)-isoxazole $^1$H-NMR(CDCl$_3$)δ: 11.57(bs, 1H), 8.61(s, 1H), 8.40(d, J=5.6 Hz, 1H), 7.50-7.40(m, 6H), 7.27-7.17(m, 2H), 6.77(dd, J=1.5, 5.6 Hz, 1H), 3.96(s, 2H).
Mass, m/e: 408(M$^+$), 109(base).

Example 60

3-(4-Chlorophenyl)-5-[(3-fluorophenyl)acetylamino]-4-(4-pyrimidinyl)-isoxazole $^1$H-NMR(CDCl$_3$)δ: 11.42(bs, 1H), 8.66(s, 1H), 8.40(d, J=5.4 Hz, 1H), 7.49(d, J=8.7 Hz, 2H), 7.46-7.40(m, 1H), 7.42(d, J=8.7 Hz, 2H), 7.20-7.12(m, 3H), 6.77(dd, J=1.5 Hz, 5.4 Hz, 1H), 3.94(s, 2H).
Mass, m/e: 408(M$^+$), 109(base).

Example 61

3-(4-Chlorophenyl)-5-[(2-chlorophenyl)acetylamino]-4-(4-pyrimidinyl)-isoxazole $^1$H-NMR(CDCl$_3$)δ: 11.44(bs, 1H), 8.53(s, 1H), 8.39(d, J=5.6 Hz, 1H), 7.54-7.39(m, 8H), 6.76(dd, J=1.5 Hz, 5.6 Hz, 1H), 4.06(s, 2H).
Mass, m/e: 424(M$^+$), 256(base).

Example 62

5-[(2-Bromophenyl)acetylamino]-3-(4-chlorophenyl)-4-(4-pyrimidinyl)-isoxazole $^1$H-NMR(CDCl$_3$)δ: 11.42(bs, 1H), 8.52(s, 1H), 8.39(d, J=5.4 Hz, 1H), 7.72(d, J=8.1 Hz, 1H), 7.50-7.40(m, 6H), 7.36-7.31(m, 1H), 6.76(dd, J=1.2 Hz, 5.4 Hz, 1H), 4.08(s, 2H).
Mass, m/e: 468(M$^+$), 256(base).

Example 63

3-(4-Chlorophenyl)-5-[(2-iodophenyl)acetylamino]-4-(4-pyrimidinyl)-isoxazole $^1$H-NMR(CDCl$_3$)δ: 11.37(bs, 1H), 8.50(s, 1H), 8.38(d, J=5.6 Hz, 1H), 8.00(d, J=7.7 Hz, 1H), 7.50-7.46(m, 4H), 7.42(d, J=8.5 Hz, 2H), 7.18-7.14(m, 1H), 6.76(dd, J=1.5 Hz, 5.6 Hz, 1H), 4.09(s, 2H).
Mass, m/e: 516(M$^+$), 256(base).

Example 64

3-(4-Chlorophenyl)-5-[(2,5-difluorophenyl)acetylamino]-4-(4-pyrimidinyl)isoxazole $^1$H-NMR(CDCl$_3$)δ: 11.61(bs, 1H), 8.80(s, 1H), 8.44(d, J=5.8 Hz, 1H), 7.50(d, J=8.5 Hz, 2H), 7.43(d, J=8.5 Hz, 2H), 7.17-7.06(m, 3H), 6.80(dd, J=1.6 Hz, 5.8 Hz, 1H), 3.94(s, 2H).
Mass, m/e: 426(M$^+$), 127(base).

Example 65

3-(4-Chlorophenyl)-5-[(3,5-difluorophenyl)acetylamino]-4-(4-pyrimidinyl)isoxazole $^1$H-NMR(CDCl$_3$)δ: 11.46(bs, 1H), 8.82(s, 1H), 8.44(d, J=5.4 Hz, 1H), 7.50(d, J=8.9 Hz, 2H), 7.43(d, J=8.9 Hz, 2H), 6.98-6.93(m, 2H), 6.90-6.84(m, 1H), 6.80(dd, J=1.2 Hz, 5.4 Hz, 1H), 3.93(s, 2H).
Mass, m/e: 426(M$^+$), 256(base).

Example 66

3-(4-Chlorophenyl)-5-[(2,6-difluorophenyl)acetylamino]-4-(4-pyrimidinyl)isoxazole $^1$H-NMR(CDCl$_3$)δ: 11.64(bs, 1H), 8.70(s, 1H), 8.42(d, J=5.4 Hz, 1H), 7.50(d, J=8.5 Hz, 2H), 7.43(d, J=8.5 Hz, 2H), 7.40-7.37(m, 1H), 7.07-7.01(m, 2H), 6.80(dd, J=1.5 Hz, 5.4 Hz, 1H), 4.01(s, 2H).
Mass, m/e: 426(M$^+$), 127(base).

Example 67

5-[(2-Chloro-4-fluorophenyl)acetylamino]-3-(4-chlorophenyl)-4-(4-pyrimidinyl)isoxazole $^1$H-NMR(CDCl$_3$)δ: 11.47(bs, 1H), 8.72(s, 1H), 8.43(d, J=5.6 Hz, 1H), 7.51-7.41(m, 5H), 7.27(dd, J=2.7 Hz, 8.5 Hz, 1H), 7.11(dt, J=2.7 Hz, 8.1 Hz, 1H), 6.73(dd, J=1.5 Hz, 5.6 Hz, 1H), 4.03(s, 2H).
Mass, m/e: 442(M$^+$), 256(base).

Example 68

5-[(2-Chloro-6-fluorophenyl)acetylamino]-3-(4-chlorophenyl)-4-(4-pyrimidinyl)isoxazole $^1$H-NMR(CDCl$_3$)δ: 11.54(bs, 1H), 8.64(s, 1H), 8.41(d, J=5.4 Hz, 1H), 7.49(d, J=8.5 Hz, 2H), 7.43(d, J=8.5 Hz, 2H), 7.40-7.34(m, 2H), 7.17(dt, J=1.2 Hz, 8.9 Hz, 1H), 6.79(dd, J=1.2 Hz, 5.4 Hz, 1H), 4.13(s, 2H).
Mass, m/e: 442(M$^+$), 256(base).

Example 69

3-(4-Chlorophenyl)-5-[(2,4-dichlorophenyl)acetylamino]-4-(4-pyrimidinyl)isoxazole $^1$H-NMR(CDCl$_3$)δ: 11.47(bs, 1H), 8.70(s, 1H), 8.43(d, J=5.6 Hz, 1H), 7.54-7.48(m, 3H), 7.44-7.36(m, 4H), 6.79(dd, J=1.5 Hz, 5.6 Hz, 1H), 4.04(s, 2H).
Mass, m/e: 458(M$^+$), 256(base).

Example 70

3-(4-Chlorophenyl)-5-[(2,6-dichlorophenyl)acetylamino]-4-(4-pyrimidinyl)isoxazole $^1$H-NMR(CDCl$_3$)δ: 11.47(bs, 1H), 8.60(s, 1H), 8.40(d, J=5.4 Hz, 1H), 7.51-7.47(m, 4H), 7.42(d, J=8.5 Hz, 2H), 7.35(dd, J=7.3 Hz, 8.4 Hz, 1H), 6.78(dd, J=1.5 Hz, 5.4 Hz, 1H), 4.31(s, 2H)
Mass, m/e: 458(M$^+$), 256(base).

Example 71

3-(4-Chlorophenyl)-5-[(2-methoxyphenyl)acetylamino]-4-(4-pyrimidinyl)isoxazole $^1$H-NMR(CDCl$_3$)δ: 11.33(bs, 1H), 8.46(d, J=1.4 Hz, 1H), 8.37(d, J=5.6 Hz, 1H), 7.49-7.40(m, 5H), 7.34(dd, J=1.4 Hz, 7.5 Hz, 1H), 7.08(dt, J=1.4 Hz, 7.5 Hz, 1H), 6.99(d, J=8.1 Hz, 1H), 6.73(dd, J=1.4 Hz, 5.6 Hz, 1H), 3.88(s, 2H), 3.80(s, 3H).
Mass, m/e: 420(M$^+$), 91(base).

Example 72

3-(4-Chlorophenyl)-5-[(3-methoxyphenyl)acetylamino]-4-(4-pyrimidinyl)isoxazole $^1$H-NMR(CDCl$_3$)δ: 11.41(bs, 1H), 8.60(d, J=1.4 Hz, 1H), 8.38(d, J=5.4 Hz, 1H), 7.48(d, J=8.9 Hz, 2H), 7.42-7.37(m, 3H), 6.99-6.94(m, 3H), 6.74(dd, J=1.4 Hz, 5.4 Hz, 1H), 3.89(s, 2H), 3.83(s, 3H).
Mass, m/e: 420(M$^+$), 148(base).

Example 73

3-(4-Chlorophenyl)-5-[(2,3-dimethoxyphenyl)acetylamino]-4-(4-pyrimidinyl)isoxazole $^1$H-NMR(CDCl$_3$)δ: 11.46(bs, 1H), 8.61(d, J=1.5 Hz, 1H), 8.36(d, J=5.4 Hz, 1H), 7.47(d, J=8.5 Hz, 2H), 7.27(d, J=8.5 Hz, 2H), 7.14(t, J=8.1 Hz, 1H), 7.00(dd, J=1.5 Hz, 8.1 Hz, 1H), 6.95(dd, J=1.5 Hz, 7.7 Hz, 1H), 6.72(dd, J=1.5 Hz, 5.4 Hz, 1H), 3.89(s, 2H), 3.89(s, 3H), 3.88(s, 3H).
Mass, m/e: 450(M$^+$), 178(base).

Example 74

3-(4-Chlorophenyl)-5-[(2,5-dimethoxyphenyl)acetylamino]-4-(4-pyrimidinyl)isoxazole $^1$H-NMR(CDCl$_3$)δ: 11.34(bs, 1H), 8.58(d, J=1.3 Hz, 1H), 8.37(d, J=5.4 Hz, 1H), 7.48(d, J=8.5 Hz, 2H), 7.41(d, J=8.5 Hz, 2H), 6.96-6.89(m, 3H), 6.74(dd, J=1.3 Hz, 5.4 Hz, 1H), 3.85(s, 2H), 3.81(s, 3H), 3.76(s, 3H).
Mass, m/e: 450(M$^+$), 178(base).

Example 75

3-(4-Chlorophenyl)-5-[(3,5-dimethoxyphenyl)acetylamino]-4-(4-pyrimidinyl)isoxazole $^1$H-NMR(CDCl$_3$)δ: 11.44(bs, 1H), 8.70(d, J=1.3 Hz, 1H), 8.39(d, J=5.4 Hz, 1H), 7.48(d, J=8.5 Hz, 2H), 7.41(d, J=8.5 Hz, 2H), 6.74(dd, J=1.3 Hz, 5.4 Hz, 1H), 6.54-6.50(m, 3H), 3.84(s, 2H), 3.81(s, 6H).
Mass, m/e: 450(M$^+$), 178(base).

Example 76

3-(4-Chlorophenyl)-5-[(2-methylphenyl)acetylamino]-4-(4-pyrimidinyl)isoxazole $^1$H-NMR(CDCl$_3$)δ: 11.35(bs, 1H), 8.41(d, J=1.4 Hz, 1H), 8.36(d, J=5.6 Hz, 1H), 7.48(d, J=8.5 Hz, 2H), 7.40(d, J=8.5 Hz, 2H), 7.37-7.31(m, 4H), 6.74(dd, J=1.4 Hz, 5.6 Hz, 1H), 3.92(s, 2H), 2.35(s, 3H)
Mass, m/e: 404(M$^+$), 256(base). .

Example 77

3-(4-Chlorophenyl)-5-[(3-methylphenyl)acetylamino]-4-(4-pyrimidinyl)isoxazole $^1$H-NMR(CDCl$_3$)δ: 11.38(s, 1H), 8.48(d, J=1.2 Hz, 1H), 8.38(d, J=5.8 Hz, 1H), 7.50-7.47(m, 2H), 7.43-7.36(m, 3H), 7.27-7.19(m, 3H), 6.74(dd, J=1.5 Hz, 5.8 Hz, 1H), 3.89(s, 2H), 2.39(s, 3H).
Mass, m/e: 404(M$^+$), 105(base).

Example 78

3-(4-Chlorophenyl)-5-[(2,5-dimethylphenyl)acetylamino]-4-(4-pyrimidinyl)isoxazole $^1$H-NMR(CDCl$_3$)δ: 11.31(bs, 1H), 8.38(d, J=1.4 Hz, 1H), 8.36(d, J=5.4 Hz, 1H), 7.48(d, J=8.5 Hz, 2H), 7.40(d, J=8.5 Hz, 2H), 7.20(s, 2H), 7.15(s, 1H), 6.73(dd, J=1.4 Hz, 5.4 Hz, 1H), 3.87(s, 2H), 2.38(s, 3H), 2.30(s, 3H).
Mass, m/e: 418(M$^+$), 146(base).

Example 79

3-(4-Chlorophenyl)-4-(4-pyrimidinyl)-5-[(2-trifluorophenyl)-acetylamino]isoxazole $^1$H-NMR(CDCl$_3$)δ: 11.37(bs, 1H), 8.57(s, 1H), 8.40(d, J=5.6 Hz, 1H), 7.81(d, J=8.1 Hz, 1H), 7.68-7.54(m, 3H), 7.49(d, J=8.5 Hz, 2H), 7.42(d, J=8.5 Hz, 2H), 6.77(dd, J=1.5 Hz, 5.6 Hz, 1H), 4.12(s, 2H).
Mass, m/e: 458(M$^+$), 256(base).

Example 80

3-(4-Chlorophenyl)-5-(2-phenylpropionylamino)-4-(4-pyrimidinyl)-isoxazole $^1$H-NMR(CDCl$_3$)δ: 11.39(bs, 1H), 8.56(d, 1.3 Hz, 1H), 8.36(d, J=5.4 Hz, 1H), 7.49-7.38(m, 9H), 6.72(dd, J=1.3 Hz, 5.4 Hz, 1H), 3.92(q, J=7.1 Hz, 1H), 1.68(d, J=7.1 Hz, 3H).
Mass, m/e: 404(M$^+$), 91(base).

Example 81

3-(4-Chlorophenyl)-5-(3-phenylpropionylamino)-4-(4-pyrimidinyl)-isoxazole $^1$H-NMR(CDCl$_3$)δ: 11.42(bs, 1H), 9.07(d, J=1.3 Hz, 1H), 8.46(d, J=5.4 Hz, 1H), 7.51(d, J=8.5 Hz, 2H), 7.45(d, J=8.5 Hz, 2H), 7.31-7.27(m, 4H), 7.20-7.16(m, 1H), 6.77(dd, J=1.3 Hz, 5.4 Hz, 1H), 3.12(t, J=7.5 Hz, 2H), 2.97(t, J=7.5 Hz, 2H).
Mass, m/e: 404(M$^+$), 105(base).

Example 82

3-(4-Chlorophenyl)-1-[(1-phenyl-cyclopropane)carbonylamino]-4-(4-pyrimidinyl)isoxazole $^1$H-NMR(CDCl$_3$)δ: 11.38(bs, 1H), 8.21(d, J=1.4 Hz, 1H), 8.32(d, J=5.4 Hz, 1H), 7.56-7.45(m, 7H), 7.40-7.37(m, 2H), 6.69(dd, J=1.4 Hz, 5.4 Hz, 1H), 1.81(q, J=3.5 Hz, 2H), 1.31(q, J=3.5 Hz, 2H)
Mass, m/e: 416(M$^+$), 117(base). .

Example 83

3-(3-Bromophenyl)-5-(phenylacetylamino)-4-(4-pyrimidinyl)isoxazole a: 5-Amino-3-(3-bromophenyl)-4-(4-pyrimidinyl)isoxazole $^1$H-NMR(CDCl$_3$)δ: 9.03(d, J=1.4 Hz, 1H), 8.34(d, J=5.7 Hz, 1H), 7.71-7.66(m, 2H), 7.46(dt, J=1.3 Hz, 7.7 Hz, 1H), 7.39(t, J=7.7 Hz, 1H), 6.90(bs, 2H), 6.71(dd, J=1.4 Hz, 5.7 Hz, 1H).
Mass, m/e: 316(M$^+$), 76(base).

b: 3-(3-Bromophenyl)-5-(phenylacetylamino)-4-(4-pyrimidinyl)-isoxazole $^1$H-NMR(CDCl$_3$)δ: 11.40(s, 1H), 8.50(bs, 1H), 8.39(d, J=5.7 Hz, 1H), 7.68(dt, J=1.9 Hz, 6.9 Hz, 1H), 7.65-7.63(m, 1H), 7.52-7.35(m, 7H), 6.73(dd, J=1.3 Hz, 5.7 Hz, 1H), 3.94 (s, 2H).
Mass, m/e: 434(M$^+$), 91(base).

Example 84

3-(3-Bromophenyl)-5-[(2-fluorophenyl)acetylamino]-4-(4-pyrimidinyl)-isoxazole

$^1$H-NMR(CDCl$_3$)δ: 11.58(s, 1H), 8.62(s, 1H), 8.41(d, J=5.7 Hz, 1H), 7.69(dt, J=1.9 Hz, 7.3 Hz, 1H), 7.66-7.64(m, 1H), 7.47-7.36(m, 4H), 7.29-7.17(m, 2H), 6.77(dd, J=1.3 Hz, 5.7 Hz, 1H), 3.97(s, 2H).
Mass, m/e: 452(M$^+$), 109(base).

Example 85

3-(3-Bromophenyl)-5-[(2-chlorophenyl)acetylamino]-4-(4-pyrimidinyl)-isoxazole

$^1$H-NMR(CDCl$_3$)δ: 11.46(s, 1H), 8.55(dd, J=1.3 Hz, 1H), 8.40(d, J=5.5 Hz, 1H), 7.68(dt, J=1.9 Hz, 7.3 Hz, 1H), 7.67-7.64(m, 1H), 7.56-7.45(m, 2H), 7.45-7.35(m, 4H), 6.76(dd, J=1.3 Hz, 5.5 Hz, 1H), 4.07(s, 2H).
Mass, m/e: 468(M$^+$), 125(base).

Example 86

3-(3-Bromophenyl)-5-[(2-bromophenyl)acetylamino]-4-(4-pyrimidinyl)isoxazole

$^1$H-NMR(CDCl$_3$)δ: 11.44(s, 1H), 8.53(s, 1H), 8.40(d, J=5.5 Hz, 1H), 7.72(dd, J=0.8 Hz, 8.8 Hz, 1H), 7.68(dt, J=1.9 Hz, 6.9 Hz, 1H), 7.67-7.64(m, 1H), 7.51-7.31(m, 5H), 6.76 (dd, J=1.5 Hz, 5.5 Hz, 1H), 4.09(s, 2H).
Mass, m/e: 512(M$^+$), 300(base).

Example 87

3-(3-Bromophenyl)-5-[(2-chloro-4-fluorophenyl)acetylamino]-4-(4-pyrimidinyl)isoxazole

$^1$H-NMR(CDCl$_3$)δ: 11.49(s, 1H), 8.73(s, 1H), 8.44(d, J=5.4 Hz, 1H), 7.69(dt, J=1.9 Hz, 7.3 Hz, 1H), 7.67-7.65(m, 1H), 7.48-7.36(m, 3H), 7.28(dd, J=2.7 Hz, 8.1 Hz, 1H), 7.12 (td, J=2.7 Hz, 8.1 Hz, 1H), 6.79(dd, J=1.5 Hz, 5.4 Hz, 1H), 4.04(s, 2H).
Mass, m/e: 486(M$^+$), 143(base).

Example 88

3-(3-Bromophenyl)-5-[(2-chloro-6-fluorophenyl)acetylamino]-4-(4-pyrimidinyl)isoxazole

$^1$H-NMR(CDCl$_3$)δ: 11.56(s, 1H), 8.65(s, 1H), 8.43(d, J=5.7 Hz, 1H), 7.69(dt, J=1.8 Hz, 7.1 Hz, 1H), 7.67-7.64(m, 1H), 7.44-7.34(m, 4H), 7.17(td, J=1.7 Hz, 8.1 Hz, 1H), 6.79 (dd, J=1.3 Hz, 5.7 Hz, 1H), 4.15(d, J=1.5 Hz, 2H).
Mass, m/e: 486(M$^+$), 143(base).

Example 89

3-(3-Bromophenyl)-5-[(2,6-dichlorophenyl)acetylamino]-4-(4-pyrimidinyl)isoxazole

$^1$H-NMR(CDCl$_3$)δ: 11.48(s, 1H), 8.61(s, 1H), 8.42(d, J=5.4 Hz, 1H), 7.69(dt, J=1.9 Hz, 7.3 Hz, 1H), 7.67-7.64(m, 1H), 7.49(d, J=8.1 Hz, 2H), 7.44-7.33(m, 3H), 6.78(dd, J=1.3 Hz, 5.5 Hz, 1H), 4.32(s, 2H).
Mass, m/e: 502(M$^+$), 300(base).

Example 90

3-(3-Bromophenyl)-5-[(3-methoxyphenyl)acetylamino]-4-(4-pyrimidinyl)isoxazole

$^1$H-NMR(CDCl$_3$)δ: 11.43(s, 1H), 8.61(d, J=1.3 Hz, 1H), 8.39(d, J=5.5 Hz, 1H), 7.68(dt, J=2.1 Hz, 6.9 Hz, 1H), 7.66-7.62(m, 1H), 7.43-7.36(m, 3H), 7.00-6.93(m, 3H), 6.74(dd, J=1.3 Hz, 5.5 Hz, 1H), 3.90(s, 2H), 3.84(s, 3H).
Mass, m/e: 464(M$^+$), 148(base).

Example 91

3-(3-Bromophenyl)-5-[(2,5-dimethoxyphenyl)acetylamino]-4-(4-pyrimidinyl)isoxazole

$^1$H-NMR(CDCl$_3$)δ: 11.36(s, 1H), 8.59(d, J=1.4 Hz, 1H), 8.39(d, J=5.7 Hz, 1H), 7.67(dt, J=1.9 Hz, 7.3 Hz, 1H), 7.66-7.63(m, 1H), 7.42-7.34(m, 2H), 6.98-6.89(m, 3H), 6.74(dd, J=1.4 Hz, 5.7 Hz, 1H), 3.86(s, 2H), 3.81(s, 3H), 3.77(s, 3H).

Example 92

3-(3-Bromophenyl)-5-[(2-methylphenyl)acetylamino]-4-(4-pyrimidinyl)isoxazole

$^1$H-NMR(CDCl$_3$)δ: 11.37(s, 1H), 8.42(d, J=1.4 Hz, 1H), 8.37(d, J=5.5 Hz, 1H), 7.68(dt, J=2.1 Hz, 6.6 Hz, 1H), 7.65-7.62(m, 1H), 7.43-7.31(m, 6H), 6.72(dd, J=1.4 Hz, 5.5 Hz, 1H), 3.93(s, 2H), 2.36(s, 3H).
Mass, m/e: 448(M$^+$), 132(base).

Example 93

3-(3-Bromophenyl)-5-[(3-methylphenyl)acetylamino]-4-(4-pyrimidinyl)isoxazole

$^1$H-NMR(CDCl$_3$)δ: 11.39(s, 1H), 8.49(s, 1H), 8.39(d, J=5.7 Hz, 1H), 7.68(dt, J=2.1 Hz, 6.9 Hz, 1H), 7.66-7.63(m, 1H), 7.42-7.35(m, 3H), 7.29-7.18(m, 3H), 6.74(dd, J=1.3 Hz, 5.7 Hz, 1H), 3.89(s, 2H), 2.40(s, 3H)
Mass, m/e: 448(M$^+$), 132(base). .

Example 94

3-(3-Bromophenyl)-5-[(2,5-dimethylphenyl)acetylamino]-4-(4-pyrimidinyl)isoxazole $^1$H-NMR(CDCl$_3$)δ: 11.33(s, 1H), 8.39(d, J=1.4 Hz, 1H), 8.37(d, J=5.7 Hz, 1H), 7.68(dt, J=1.9 Hz, 6.9 Hz, 1H), 7.65-7.62(m, 1H), 7.41-7.34(m, 2H), 7.21(bs, 2H), 7.15(bs, 1H), 6.72(dd, J=1.4 Hz, 5.7 Hz, 1H), 3.88(s, 2H), 2.39(s, 3H), 2.31(s, 3H).
Mass, m/e: 462(M$^+$), 119(base).

Example 95

3-(3-Bromophenyl)-4-(4-pyrimidinyl)-5-[(2-trifluoromethylphenyl)-acetylamino]isoxazole $^1$H-NMR(CDCl$_3$)δ: 11.39(s, 1H), 8.58(s, 1H), 8.41(d, J=5.4 Hz, 1H), 7.82(d, J=8.1 Hz, 1H), 7.71-7.63(m, 3H), 7.61-7.54(m, 2H), 7.43-7.36(m, 2H), 6.76(dd, J=1.5 Hz, 5.4 Hz, 1H), 4.13(s, 2H).
Mass, m/e: 502(M$^+$), 159(base).

Example 96

3-(4-Bromophenyl)-5-(phenylacetylamino)-4-(4-pyrimidinyl)isoxazole a: 5-Amino-3-(4-bromophenyl)-4-(4-pyrimidinyl)isoxazole $^1$H-NMR(CDCl$_3$)δ: 9.03(d, J=1.5 Hz, 1H), 8.34(d, J=5.8 Hz, 1H), 7.66(dt, J=2.3 Hz, 8.5 Hz, 2H), 7.41(dt, J=2.3 Hz, 8.5 Hz, 2H), 6.87(bs, 2H), 6.80(dd, J=1.5 Hz, 5.8 Hz, 1H).
Mass, m/e: 315(M$^+$), 173(base).

b: 3-(4-Bromophenyl)-5-(phenylacetylamino)-4-(4-pyrimidinyl)-isoxazole $^1$H-NMR(CDCl$_3$)δ: 11.39(s, 1H), 8.50(s, 1H), 8.38(d, J=5.8 Hz, 1H), 7.66-7.63(m, 2H), 7.51-7.34(m, 7H), 6.74(dd, J=1.5 Hz, 5.8 Hz, 1H), 3.94(s, 2H).
Mass, m/e: 434(M$^+$), 91(base).

Example 97

3-(4-Bromophenyl)-5-[(2-fluorophenyl)acetylamino]-4-(4-pyrimidinyl)isoxazole $^1$H-NMR(CDCl$_3$)δ: 11.57(s, 1H), 8.62(s, 1H), 8.42(d, J=5.4 Hz, 1H), 7.67-7.63(dt, J=2.1 Hz, 8.5 Hz, 2H), 7.47-7.40(m, 2H), 7.38-7.34(m, 2H), 7.28-7.18(m, 2H), 6.78(dd, J=1.5 Hz, 5.4 Hz, 1H), 3.97(s, 2H).
Mass, m/e: 452(M$^+$), 109(base).

Example 98

3-(4-Bromophenyl)-5-[(2-chlorophenyl)]acetylamino]-4-(4-pyrimidinyl)isoxazole $^1$H-NMR(CDCl$_3$)δ: 11.44(s, 1H), 8.54(s, 1H), 8.40(d, J=5.8 Hz, 1H), 7.67-7.63(m, 2H), 7.54-7.40(m, 4H), 7.37-7.34(m, 2H), 6.77(dd, J=1.5 Hz, 5.8 Hz, 1H), 4.07(s, 2H)
Mass, m/e: 468(M$^+$), 125(base).

Example 99

3-(2,3-Difluorophenyl)-5-(phenylacetylamino)-4-(4-pyrimidinyl)-isoxazole a: 5-Amino-3-(2,3-difluorophenyl)-4-(4-pyrimidinyl)isoxazole $^1$H-NMR(CDCl$_3$)δ: 9.03(d, J=1.5 Hz, 1H), 8.36(d, J=5.4 Hz, 1H), 7.41-7.24(m, 3H), 6.92(bs, 2H), 6.60(dt, J=1.5 Hz, 5.4 Hz, 1H).
Mass, m/e: 274(M$^+$), 52(base).

b: 3-(2,3-Difluorophenyl)-5-(phenylacetylamino)-4-(4-pyrimidinyl)-isoxazole $^1$H-NMR(CDCl$_3$)δ: 11.45(s, 1H), 8.49(d, J=1.2 Hz, 1H), 8.41(d, J=5.4 Hz, 1H), 7.52-7.35(m, 6H), 7.30-7.24(m, 2H), 6.74(dt, J=1.5 Hz, 5.4 Hz, 1H), 3.95(s, 2H).
Mass, m/e: 392(M$^+$), 91(base).

Example 100

3-(2,3-Difluorophenyl)-5-[(2-fluorophenyl)acetylamino]-4-(4-pyrimidinyl)isoxazole $^1$H-NMR(CDCl$_3$)δ: 11.63(s, 1H), 8.62(d, J=1.2 Hz, 1H), 8.44(d, J=5.8 Hz, 1H), 7.47-7.36(m, 3H), 7.31-7.19(m, 4H), 6.68(dt, J=1.5 Hz, 5.8 Hz, 1H), 3.98(d, J=1.2 Hz, 2H).
Mass, m/e: 410(M$^+$), 109(base).

Example 101

5-[(2-Chlorophenyl)acetylamino]-3-(2,3-difluorophenyl)-4-(4-pyrimidinyl)isoxazole $^1$H-NMR(CDCl$_3$)δ: 11.51(s, 1H), 8.55(d, J=0.8 Hz, 1H), 8.43(d, J=5.4 Hz, 1H), 7.55-7.36(m, 5H), 7.29-7.24(m, 2H), 6.67(dt, J=1.5 Hz, 5.4 Hz, 1H), 4.08(s, 2H).
Mass, m/e: 426(M$^+$), 125(base).

Example 102

3-(2,4-Difluorophenyl)-5-(phenylacetylamino)-4-(4-pyrimidinyl)-isoxazole a: 5-Amino-3-(2,4-difluorophenyl)-4-(4-pyrimidinyl)isoxazole $^1$H-NMR(CDCl$_3$)δ: 9.02(d, J=1.2 Hz, 1H), 8.35(d, J=5.4 Hz, 1H), 7.51(dt, J=6.6 Hz, 8.5 Hz, 1H), 7.08-6.97(m, 2H), 6.92(bs, 2H), 6.60(td, J=1.2 Hz, 5.4 Hz, 1H).
Mass, m/e: 274(M$^+$), 129(base).

b: 3-(2,4-Difluorophenyl)-5-(phenylacetylamino)-4-(4-pyrimidinyl)-isoxazole $^1$H-NMR(CDCl$_3$)δ: 11.44(bs, 1H), 8.48(s, 1H), 8.40(d, J=5.6 Hz, 1H), 7.54-7.39(m, 6H), 7.06(dt, J=1.9 Hz, 8.1 Hz, 1H), 6.97(dt, J=2.3 Hz, 9.3 Hz, 1H), 6.65(td, J=1.5 Hz, 5.6 Hz, 1H), 3.94(s, 2H)
Mass, m/e: 392(M$^+$), 91(base).

Example 103

3-(2,4-Difluorophenyl)-5-[(2-fluorophenyl)acetylamino]-4-(4-pyrimidinyl)isoxazole $^1$H-NMR(CDCl$_3$)δ: 11.61(bs, 1H), 8.61(d, J=1.4 Hz, 1H), 8.42(d, J=5.6 Hz, 1H), 7.51(dt, J=6.2 Hz, 8.1 Hz, 1H), 7.44-7.41(m, 2H), 7.28-7.24(m, 1H), 7.20(t, J=9.6 Hz, 1H), 7.09-7.04(m, 1H), 7.00-6.95(m, 1H), 6.71(td, J=1.4 Hz, 5.6 Hz, 1H), 3.96(s, 2H).
Mass, m/e: 410(M$^+$), 109(base).

Example 104

3-(2,4-Difluorophenyl)-5-[(3-fluorophenyl)acetylamino]-4-(4-pyrimidinyl)isoxazole $^1$H-NMR(CDCl$_3$)δ: 11.47(s, 1H), 8.65(s, 1H), 8.43(d, J=5.4 Hz, 1H), 7.52(dt, J=6.2 Hz, 8.1 Hz, 1H), 7.47-7.43(m, 1H), 7.19(d, J=7.7 Hz, 1H), 7.16-7.12(m, 2H), 7.07(dt, J=2.3 Hz, 7.7 Hz, 1H), 6.98(dt, J=2.3 Hz, 8.5 Hz, 1H), 6.68(td, J=1.9 Hz, 5.4 Hz, 1H), 3.94(s, 2H).
Mass, m/e: 410(M$^+$), 258(base).

Example 105

5-[(2-Chlorophenyl)acetylamino]-3-(2,4-difluorophenyl)-4-(4-pyrimidinyl)isoxazole $^1$H-NMR(CDCl$_3$)δ: 11.49(bs, 1H), 8.53(s, 1H), 8.41(d, J=5.4 Hz, 1H), 7.54-7.40(m, 5H), 7.09-7.04(m, 1H), 6.98(dt, J=2.3 Hz, 8.5 Hz, 1H), 6.67(td, J=1.5 Hz, 5.4 Hz, 1H), 4.07(s, 2H).
Mass, m/e: 426(M$^+$), 258(base).

Example 106

5-[(2-Bromophenyl)acetylamino]-3-(2,4-difluorophenyl)-4-(4-pyrimidinyl)isoxazole $^1$H-NMR(CDCl$_3$)δ: 11.47(bs, 1H), 9.02(d, J=1.5 Hz, 1H), 8.52(s, 1H), 8.41(d, J=5.2 Hz, 1H), 7.72(d, J=8.1 Hz, 1H), 7.54-7.45(m, 3H), 7.36-7.32(m, 1H), 7.09-6.95(m, 1H), 6.67(td, J=1.5 Hz, 5.2 Hz, 1H), 4.09(s, 2H).
Mass, m/e: 470(M$^+$), 258(base).

Example 107

3-(2,4-Difluorophenyl)-5-[(2-iodophenyl)acetylamino]-4-(4-pyrimidinyl)isoxazole $^1$H-NMR(CDCl$_3$)δ: 11.42(s, 1H), 8.51(s, 1H), 8.41(d, J=5.4 Hz, 1H), 8.00(d, J=7.7 Hz, 1H), 7.52(dt, J=6.2 Hz, 8.5 Hz, 1H), 7.49-7.48(m, 2H), 7.18-7.14(m, 1H), 7.06(dt, J=2.7 Hz, 8.9 Hz, 1H), 6.98(dt, J=2.3 Hz, 8.9 Hz, 1H), 6.67(td, J=1.5 Hz, 5.4 Hz, 1H), 4.10(s, 2H).
Mass, m/e: 518(M$^+$), 258(base).

Example 108

3-(2,4-Difluorophenyl)-5-[(2,4-difluorophenyl)acetylamino]-4-(4-pyrimidinyl)isoxazole $^1$H-NMR(CDCl$_3$)δ: 11.64(s, 1H), 8.79(d, J=1.2 Hz, 1H), 8.46(d, J=5.6 Hz, 1H), 7.53(dt, J=6.2 Hz, 8.5 Hz, 1H), 7.40(dt, J=6.6 Hz, 8.5 Hz, 1H), 7.10-7.05(m, 1H), 7.01-6.92(m, 3H), 6.72(td, J=1.2 Hz, 5.6 Hz, 1H), 3.93(s, 2H).
Mass, m/e: 428(M$^+$), 254(base).

Example 109

3-(2,4-Difluorophenyl)-5-[(2,5-difluorophenyl)acetylamino]-4-(4-pyrimidinyl)isoxazole $^1$H-NMR(CDCl$_3$)δ: 11.67(s, 1H), 8.79(s, 1H), 8.46(d, J=5.6 Hz, 1H), 7.53(dt, J=6.2 Hz, 8.5 Hz, 1H), 7.18-7.05(m, 4H), 6.99(dt, J=2.7 Hz, 8.9 Hz, 1H), 6.72(td, J=1.9 Hz, 5.6 Hz, 1H), 3.95(s, 2H).
Mass, m/e: 428(M$^+$), 258(base).

Example 110

3-(2,4-Difluorophenyl)-5-[(2,6-difluorophenyl)acetylamino]-4-(4-pyrimidinyl)isoxazole $^1$H-NMR(CDCl$_3$)δ: 11.69(s, 1H), 8.69(s, 1H), 8.46(d, J=5.4 Hz, 1H), 7.53(dt, J=6.2 Hz, 8.1 Hz, 1H), 7.45-7.37(m, 1H), 7.10-6.96(m, 4H), 6.71(td, J=1.5 Hz, 5.4 Hz, 1H), 4.01(s, 2H).
Mass, m/e: 428(M$^+$), 258(base).

Example 111

5-[(2-Chloro-4-fluorophenyl)acetylamino]-3-(2,4-difluorophenyl)-4-(4-pyrimidinyl)isoxazole $^1$H-NMR(CDCl$_3$)δ: 11.52(bs, 1H), 8.71(s, 1H), 8.45(d, J=5.4 Hz, 1H), 7.53(dt, J=6.2 Hz, 8.1 Hz, 1H), 7.45(dd, J=5.8 Hz, 8.5 Hz, 1H), 7.28(dd, J=2.7 Hz, 8.1 Hz, 1H), 7.14-7.05(m, 2H), 6.99(dt, J=2.3 Hz, 9.6 Hz, 1H), 6.71(td, J=1.9 Hz, 5.4 Hz, 1H), 4.04(s, 2H).
Mass, m/e: 444(M$^+$), 258(base).

Example 112

3-(2,4-Difluorophenyl)-5-[(2-chloro-6-fluorophenyl)acetylamino]-4-(4-pyrimidinyl)isoxazole $^1$H-NMR(CDCl$_3$)δ: 11.59(s, 1H), 8.64(s, 1H), 8.44(d, J=5.2 Hz, 1H), 7.53(dt, J=6.2 Hz, 8.1 Hz, 1H), 7.42-7.35(m, 2H), 7.16(dt, J=1.5 Hz, 8.9 Hz, 1H), 7.10-7.05(m, 1H), 6.99(dt, J=2.3 Hz, 8.5 Hz, 1H), 6.78(td, J=1.9 Hz, 5.2 Hz, 1H), 4.14(s, 2H).
Mass, m/e: 444(M$^+$), 258(base).

Example 113

5-[(2,4-Dichlorophenyl)acetylamino]-3-(2,4-difluorophenyl)-4-(4-pyrimidinyl)isoxazole $^1$H-NMR(CDCl$_3$)δ: 10.11(bs, 1H), 8.70(s, 1H), 8.46(d, J=5.6 Hz, 1H), 7.55-7.50(m, 2H), 7.42-7.36(m, 2H), 7.10-7.05(m, 1H), 7.01-6.96(m, 1H), 6.71(td, J=1.6 Hz, 5.6 Hz, 1H), 4.04(s, 2H).
Mass, m/e: 460(M$^+$), 258(base).

Example 114

5-[(2,6-Dichlorophenyl)acetylamino]-3-(2,4-difluorophenyl)-4-(4-pyrimidinyl)isoxazole $^1$H-NMR(CDCl$_3$)δ: 11.51(bs, 1H), 8.60(s, 1H), 8.43(d, J=5.4 Hz, 1H), 7.55-7.48(m, 3H), 7.35(dd, J=7.7 Hz, 8.5 Hz, 1H), 7.07(dt, J=1.5 Hz, 7.7 Hz, 1H), 6.98(dt, J=2.7 Hz, 9.6 Hz, 1H), 6.70(td, J=1.9 Hz, 5.4 Hz, 1H), 4.31(s, 2H).
Mass, m/e: 460(M$^+$), 258(base).

Example 115

3-(2,4-Difluorophenyl)-5-[(2-methoxyphenyl)acetylamino]-4-(4-pyrimidinyl)isoxazole $^1$H-NMR(CDCl$_3$)δ: 11.48(s, 1H), 8.46(d, J=1.2 Hz, 1H), 8.38(d, J=5.6 Hz, 1H), 7.51(dt, J=6.6 Hz, 8.5 Hz, 1H), 7.45 (dt, J=1.5 Hz, 8.1 Hz, 1H), 7.34(dd, J=1.5 Hz, 7.3 Hz, 1H), 7.11-7.03(m, 2H), 7.00-6.94(m, 2H), 6.64(td, J=1.5 Hz, 5.6 Hz, 1H), 3.88(s, 2H), 3.81(s, 3H).
Mass, m/e: 422(M$^+$), 91(base).

Example 116

3-(2,4-Difluorophenyl)-5-[(3-methoxyphenyl)acetylamino]-4-(4-pyrimidinyl)isoxazole $^1$H-NMR(CDCl$_3$)δ: 11.46(s, 1H), 8.59(d, J=1.4 Hz, 1H), 8.39(d, J=5.6 Hz, 1H), 7.51(dt, J=6.6 Hz, 8.5 Hz, 1H), 7.40(t, J=7.7 Hz, 1H), 7.06(dt, J=1.5 Hz, 7.7 Hz, 1H), 6.99-6.94(m, 4H), 6.66(td, J=1.4 Hz, 5.6 Hz, 1H), 3.90(s, 2H), 3.83(s, 3H).
Mass, m/e: 422(M$^+$), 148(base).

Example 117

3-(2,4-Difluorophenyl)-5-[(2,3-dimethoxyphenyl)acetylamino]-4-(4-pyrimidinyl)isoxazole $^1$H-NMR(CDCl$_3$)δ: 11.51(s, 1H), 8.62(d, J=1.7 Hz, 1H), 8.39(d, J=5.4 Hz, 1H), 7.50(dt, J=6.2 Hz, 8.5 Hz, 1H), 7.14(t, J=7.7 Hz, 1H), 7.08-7.03(m, 1H), 7.01-6.94(m, 3H), 6.64(td, J=1.7 Hz, 5.4 Hz, 1H), 3.90(s, 2H), 3.89(s, 3H), 3.89(s, 3H).
Mass, m/e: 452(M$^+$), 178(base).

Example 118

3-(2,4-Difluorophenyl)-5-[(2,5-dimethylphenyl)acetylamino]-4-(4-pyrimidinyl)isoxazole $^1$H-NMR(CDCl$_3$)δ: 11.39(s, 1H), 8.58(d, J=1.4 Hz, 1H), 8.40(d, J=5.6 Hz, 1H), 7.51(dt, J=6.2 Hz, 8.5 Hz, 1H), 7.06 (dt, J=2.3 Hz, 8.5 Hz, 1H), 6.99-6.90(m, 4H), 6.65(td, J=1.4 Hz, 5.6 Hz, 1H), 3.86(s, 2H), 3.81(s, 3H), 3.77(s, 3H).
Mass, m/e: 452(M$^+$), 178(base).

Example 119

3-(2,4-Difluorophenyl)-5-[(3,5-dimethylphenyl)acetylamino]-4-(4-pyrimidinyl)isoxazole $^1$H-NMR(CDCl$_3$)δ: 11.49(s, 1H), 8.70(d, J=1.7 Hz, 1H), 8.41(d, J=5.6 Hz, 1H), 7.51(dt, J=6.2 Hz, 8.5 Hz, 1H), 7.09-7.04(m, 1H), 7.00-6.95(m, 1H), 6.66(td, J=1.7 Hz, 5.6 Hz, 1H), 6.54(d, J=2.3 Hz, 2H), 6.51(t, J=2.3 Hz, 1H), 3.84(s, 2H), 3.81(s, 6H).
Mass, m/e: 452(M$^+$), 178(base).

Example 120

3-(2,4-Difluorophenyl)-5-[(2-methylphenyl)acetylamino]-4-(4-pyrimidinyl)isoxazole $^1$H-NMR(CDCl$_3$)δ: 11.40(s, 1H), 8.41(d, J=1.54 Hz, 1H), 8.38(d, J=5.4 Hz, 1H), 7.50(dt, J=6.2 Hz, 8.5 Hz, 1H), 7.42-7.31(m, 4H), 7.08-7.03(m, 1H), 6.97(dt, J=2.3 Hz, 8.9 Hz, 1H), 6.64(td, J=1.9 Hz, 5.4 Hz, 1H), 3.92(s, 2H), 2.36(s, 3H).
Mass, m/e: 406(M$^+$), 258(base).

Example 121

3-(2,4-Difluorophenyl)-5-[(3-methylphenyl)acetylamino]-4-(4-pyrimidinyl)isoxazole $^1$H-NMR(CDCl$_3$)δ: 11.43(s, 1H), 8.48(s, 1H), 8.40(d, J=5.4 Hz, 1H), 7.54-7.49(m, 1H), 7.40-7.36(m, 1H), 7.28-7.20(m, 3H), 7.09-7.04(m, 1H), 7.00-6.95(m, 1H), 6.76(dt, J=1.5 Hz, 5.4 Hz, 1H), 3.89(s, 2H), 2.40(s, 3H).
Mass, m/e: 406(M$^+$), 258(base).

Example 122

3-(2,4-Difluorophenyl)-5-[(2,5-dimethylphenyl)acetylamino]-4-(4-pyrimidinyl)isoxazole $^1$H-NMR(CDCl$_3$)δ: 11.36(s, 1H), 8.39(d, J=5.4 Hz, 1H), 8.38(s, 1H), 7.50(dt, J=6.2 Hz, 8.1 Hz, 1H), 7.20(bs, 2H), 7.15(s, 1H), 7.06(dt, J=2.7 Hz, 8.9 Hz, 1H), 6.97(dt, J=2.7 Hz, 8.9 Hz, 1H), 6.64(td, J=1.9 Hz, 5.4 Hz, 1H), 3.88(s, 2H), 2.38(s, 3H), 2.31(s, 3H).
Mass, m/e: 420(M$^+$), 258(base).

Example 123

3-(2,4-Difluorophenyl)-4-(4-pyrimidinyl)-5-[(2-trifluoromethylphenyl)-acetylamino]isoxazole $^1$H-NMR(CDCl$_3$)δ: 11.42(s, 1H), 8.57(s, 1H), 8.42(d, J=5.4 Hz, 1H), 7.82(d, J=8.1 Hz, 1H), 7.67(t, J=6.9 Hz, 1H), 7.59-7.49(m, 3H), 7.07(dt, J=2.7 Hz, 8.9 Hz, 1H), 6.98(dt, J=2.7 Hz, 8.9 Hz, 1H), 6.68(td, J=1.9 Hz, 5.4 Hz, 1H), 4.12(s, 2H).
Mass, m/e: 460(M$^+$), 258(base).

Example 124

3-(2,4-Difluorophenyl)-5-(3-phenylpropionylamino)-4-(4-pyrimidinyl)-isoxazole $^1$H-NMR(CDCl$_3$)δ: 11.49(bs, 1H), 9.07(d, J=1.5 Hz, 1H), 8.48(d, J=5.4 Hz, 1H), 7.55(dt, J=6.2 Hz, 8.5 Hz, 1H), 7.31-7.26(m, 5H), 7.11-7.06(m, 1H), 7.03-6.98(m, 1H), 6.73(td, J=1.5 Hz, 5.4 Hz, 1H), 3.12(t, J=7.5 Hz, 2H), 2.98(t, J=7.5 Hz, 2H).
Mass, m/e: 406(M$^+$), 91(base).

Example 125

3-(2,4-Difluorophenyl)-5-(1-phenylcyclopropanecarbonylamino)-4-(4-pyrimidinyl)isoxazole $^1$H-NMR(CDCl$_3$)δ: 11.44(bs, 1H), 8.35(d, J=5.8 Hz, 1H), 8.21(d, J=1.3 Hz, 1H), 7.57-7.46(m, 6H), 7.05(dt, J=2.5 Hz, 8.5 Hz, 1H), 6.95(dt, J=2.5 Hz, 9.3 Hz, 1H), 6.61(td, J=1.3 Hz, 5.8 Hz, 1H), 1.85(q, J=3.9 Hz, 2H), 1.31(q, J=3.9 Hz, 2H).
Mass, m/e: 418(M$^+$), 117(base).

Example 126

3-(2,6-Difluorophenyl)-5-(phenylacetylamino)-4-(4-pyrimidinyl)-isoxazole a: 5-Amino-3-(2,6-difluorophenyl)-4-(4-pyrimidinyl)isoxazole $^1$H-NMR(CDCl$_3$)δ: 9.02(d, J=1.5 Hz, 1H), 8.34(d, J=5.4 Hz, 1H), 7.58-7.50(m, 1H), 7.11-7.07(m, 2H), 6.94(bs, 2H), 6.57-6.54(m, 1H).
Mass, m/e: 274(M$^+$), 129(base).

b: 3-(2,6-Difluorophenyl)-5-(phenylacetylamino)-4-(4-pyrimidinyl)-isoxazole $^1$H-NMR(CDCl$_3$)δ: 11.48(s, 1H), 8.48(d, J=1.2 Hz, 1H), 8.38(d, J=5.4 Hz, 1H), 7.58-7.41(m, 6H), 7.11-7.06(m, 2H), 6.60(dd, J=1.2 Hz, 5.4 Hz, 1H), 3.95(s, 2H).
Mass, m/e: 392(M$^+$), 91(base).

Example 127

5-[(2-Chlorophenyl)acetylamino]-3-(2,6-difluorophenyl)-4-(4-pyrimidinyl)isoxazole $^1$H-NMR(CDCl$_3$)δ: 11.53(s, 1H), 8.54(bs, 1H), 8.40(d, J=5.8 Hz, 1H), 7.59-7.38(m, 5H), 7.10-7.06(m, 2H), 6.62(d, J=4.6 Hz, 1H), 4.08(s, 2H).
Mass, m/e: 426(M$^+$), 258(base).

Example 128

3-(3,4-Difluorophenyl)-5-(phenylacetylamino)-4-(4-pyrimidinyl)-isoxazole a: 5-Amino-3-(3,4-difluorophenyl)-4-(4-pyrimidinyl)isoxazole $^1$H-NMR(CDCl$_3$)δ: 9.04(d, J=1.4 Hz, 1H), 8.37(d, J=5.7 Hz, 1H), 7.55-7.10(m, 3H), 6.90(bs, 2H), 6.71(dd, J=1.4 Hz, 5.7 Hz, 1H).
Mass, m/e: 274(M$^+$), 129(base).

b: 3-(3,4-Difluorophenyl)-5-(phenylacetylamino)-4-(4-pyrimidinyl)-isoxazole $^1$H-NMR(CDCl$_3$)δ: 11.37(s, 1H), 8.50(d, J=0.8 Hz, 1H), 8.40(d, J=5.5 Hz, 1H), 7.52-7.20(m, 8H), 6.74(dd, J=1.3 Hz, 5.5 Hz, 1H), 3.94(s, 1H).
Mass, m/e: 392(M$^+$), 91(base).

Example 129

3-(2-Chloro-4-fluorophenyl)-5-(phenylacetylamino)-4-(4-pyrimidinyl)-isoxazole a: 5-Amino-3-(2-chloro-4-fluorophenyl)-4-(4-pyrimidinyl)isoxazole $^1$H-NMR(CDCl$_3$)δ: 9.00(d, J=1.6 Hz, 1H), 8.32(d, J=5.6 Hz, 1H), 7.47(dd, J=6.2 Hz, 8.5 Hz, 1H), 7.31(dd, J=2.7 Hz, 8.5 Hz, 1H), 7.16(dt, J=2.7 Hz, 8.5 Hz, 1H), 6.93(bs, 2H), 6.42(dd, J=1.6 Hz, 5.6 Hz, 1H), 2.41(s, 3H).
Mass, m/e: 290(M$^+$), 255(base).

b: 3-(2-Chloro-4-fluorophenyl)-5-(phenylacetylamino)-4-(4-pyrimidinyl)isoxazole $^1$H-NMR(CDCl$_3$)δ: 11.48(bs, 1H), 8.47(d, J=1.3 Hz, 1H), 8.37(d, J=5.6 Hz, 1H), 7.51-7.40(m, 6H), 7.29(dd, J=2.3 Hz, 8.1 Hz, 1H), 7.15(dt, J=2.7 Hz, 8.5 Hz, 1H), 6.47(dd, J=1.3 Hz, 5.6 Hz, 1H), 3.94(s, 2H).
Mass, m/e: 408(M$^+$), 91(base).

Example 130

3-(2-Chloro-4-fluorophenyl)-5-[(2-fluorophenyl)acetylamino]-4-(4-pyrimidinyl)isoxazole $^1$H-NMR(CDCl$_3$)δ: 11.65(s, 1H), 8.60(d, J=1.2 Hz, 1H), 8.40(d, J=5.8 Hz, 1H), 7.46-7.41(m, 3H), 7.31-7.16(m, 4H), 6.50(dd, J=1.2 Hz, 5.8 Hz, 1H), 3.96(s, 2H).
Mass, m/e: 426(M$^+$), 109(base).

Example 131

3-(2-Chloro-4-fluorophenyl)-5-[(2-chlorophenyl)acetylamino]-4-(4-pyrimidinyl)isoxazole $^1$H-NMR(CDCl$_3$)δ: 11.52(s, 1H), 8.52(d, J=1.2 Hz, 1H), 8.41(d, J=5.6 Hz, 1H), 7.54-7.52(m, 1H), 7.49-7.40(m, 4H), 7.29(dd, J=2.7 Hz, 8.3 Hz, 1H), 7.16(td, J=2.7 Hz, 8.3 Hz, 1H), 6.49(dd, J=1.2 Hz, 5.6 Hz, 1H), 4.07(s, 2H).
Mass, m/e: 442(M$^+$), 274(base).

Example 132

3-(3-Chloro-4-fluorophenyl)-5-(phenylacetylamino)-4-(4-pyrimidinyl)-isoxazole a: 5-Amino-3-(3-chloro-4-fluorophenyl)-4-(4-pyrimidinyl)-isoxazole $^1$H-NMR(CDCl$_3$)δ: 9.04(d, J=1.4 Hz, 1H), 8.37(d, J=5.6 Hz, 1H), 7.75-7.15(m, 3H), 6.89(bs, 2H), 6.71(dd, J=1.4 Hz, 5.6 Hz, 1H).
Mass, m/e: 290(M$^+$), 145(base).

b: 3-(3-Chloro-4-fluorophenyl)-5-(phenylacetylamino)-4-(4-pyrimidinyl)isoxazole $^1$H-NMR(CDCl$_3$)δ: 11.38(s, 1H), 8.50(d, J=1.4 Hz, 1H), 8.41(d, J=5.6 Hz, 1H), 7.56(dd, J=2.3 Hz, 6.9 Hz, 1H), 7.52-7.32(m, 6H), 7.28(t, J=8.5 Hz, 1H), 6.74(dd, J=1.4 Hz, 5.6 Hz, 1H), 3.94(s, 2H).
Mass, m/e: 408(M$^+$), 91(base).

Example 133

3-(3-Chloro-4-fluorophenyl)-5-[(2-fluorophenyl)acetylamino]-4-(4-pyrimidinyl)isoxazole $^1$H-NMR(CDCl$_3$)δ: 11.55(s, 1H), 8.63(s, 1H), 8.44(d, J=5.4 Hz, 1H), 7.55(t, J=7.7 Hz, 1H), 7.47-7.40(m, 2H), 7.30(dd, J=1.9 Hz, 8.9 Hz, 1H), 7.27(dd, J=1.2 Hz, 7.7 Hz, 1H), 7.24-7.17(m, 2H), 6.78(dd, J=1.2 Hz, 5.4 Hz, 1H), 3.96(s, 2H).
Mass, m/e: 426(M$^+$), 109(base).

Example 134

3-(2-Fluoro-4-chlorophenyl)-5-(phenylacetylamino)-4-(4-pyrimidinyl)-isoxazole a: 5-Amino-3-(4-chloro-2-fluorophenyl)-4-(4-pyrimidinyl)isoxazole $^1$H-NMR(CDCl$_3$)δ: 9.02(d, J=1.3 Hz, 1H), 8.36(d, J=5.6 Hz, 1H), 7.47(t, J=7.7 Hz, 1H), 7.32(dd, J=1.9 Hz, 8.5 Hz, 1H), 7.28(dd, J=1.9 Hz, 9.2 Hz, 1H), 6.91(bs, 2H), 6.61(dd, J=1.3 Hz, 5.6 Hz, 1H).
Mass, m/e: 290(M$^+$), 145(base).

b: 3-(2-Fluoro-4-chlorophenyl)-5-(phenylacetylamino)-4-(4-pyrimidinyl)isoxazole $^1$H-NMR(CDCl$_3$)δ: 11.44(bs, 1H), 8.49(d, J=1.4 Hz, 1H), 8.41(d, J=5.4 Hz, 1H), 7.51-7.39(m, 6H), 7.32(dd, J=2.3 Hz, 8.5 Hz, 1H), 7.25(dd, J=1.9 Hz, 9.3 Hz, 1H), 6.66(td, J=1.4 Hz, 5.4 Hz, 1H), 3.94(s, 2H).
Mass, m/e: 384(M$^+$), 91(base).

Example 135

3-(4-Chloro-2-fluorophenyl)-5-[(2-fluorophenyl)acetylamino]-4-(4-pyrimidinyl)isoxazole $^1$H-NMR(CDCl$_3$)δ: 11.62(s, 1H), 8.61(d, J=1.5 Hz, 1H), 8.44(d, J=5.2 Hz, 1H), 7.49-7.40(m, 3H), 7.33(dd, J=1.9 Hz, 7.7 Hz, 1H), 7.28-7.24(m, 2H), 7.20(t, J=8.5 Hz, 1H), 6.69(td, J=1.5 Hz, 5.2 Hz, 1H), 3.96(s, 2H).
Mass, m/e: 426(M$^+$), 109(base).

Example 136

3-(4-Chloro-2-fluorophenyl)-5-[(2-chlorophenyl)acetylamino]-4-(4-pyrimidinyl)isoxazole $^1$H-NMR(CDCl$_3$)δ: 11.49(s, 1H), 8.54(s, 1H), 8.42(d, J=5.8 Hz, 1H), 7.54-7.52(m, 1H), 7.49-7.45(m, 2H), 7.42-7.40(m, 2H), 7.32(dd, J=1.9 Hz, 8.5 Hz, 1H), 7.26(dd, J=2.3 Hz, 8.9 Hz, 1H), 6.49(td, J=1.5 Hz, 5.8 Hz, 1H), 4.07(s, 2H).
Mass, m/e: 442(M$^+$), 274(base).

Example 137

3-(4-Chloro-3-fluorophenyl)-5-(phenylacetylamino)-4-(4-pyrimidinyl)-isoxazole a: 5-Amino-3-(4-chloro-3-fluorophenyl)-4-(4-pyrimidinyl)-isoxazole $^1$H-NMR(CDCl$_3$)δ: 9.03(d, J=1.5 Hz, 1H), 8.36(d, J=5.8 Hz, 1H), 7.55(t, J=8.1 Hz, 1H), 7.35(dd, J=1.9 Hz, 9.3 Hz, 1H), 7.28-7.26(m, 1H), 6.91(bs, 2H), 6.72(dd, J=1.5 Hz, 5.8 Hz, 1H).
Mass, m/e: 290(M$^+$), 145(base).

b: 3-(4-Chloro-3-fluorophenyl)-5-(phenylacetylamino)-4-(4-pyrimidinyl)isoxazole $^1$H-NMR(CDCl$_3$)δ: 11.37(bs, 1H), 8.50(d, J=1.3 Hz, 1H), 8.41(d, J=5.6 Hz, 1H), 7.54(t, J=8.5 Hz, 1H), 7.49-7.45(m, 3H), 7.41-7.39(m, 2H), 7.29(dd, J=1.9 Hz, 8.9 Hz, 1H), 7.22-7.20(m, 1H), 6.75(dd, J=1.3 Hz, 5.6 Hz, 1H), 3.93(s, 2H).
Mass, m/e: 408(M$^+$), 91(base).

Example 138

3-(4-Chloro-3-fluorophenyl)-5-[(2-chlorophenyl)acetylamino]-4-(4-pyrimidinyl)isoxazole $^1$H-NMR(CDCl$_3$)δ: 11.43(s, 1H), 8.55(d, J=1.2 Hz, 1H), 8.42(d, J=5.6 Hz, 1H), 7.57-7.52(m, 2H), 7.48-7.46(m, 1H), 7.43-7.40(m, 2H), 7.30(dd, J=1.9 Hz, 8.9 Hz, 1H), 7.23-7.21(m, 1H), 6.77(dd, J=1.2 Hz, 5.6 Hz, 1H), 4.06(s, 2H).
Mass, m/e: 442(M$^+$), 274(base).

Example 139

3-(3-Bromo-4-fluorophenyl)-5-(phenylacetylamino)-4-(4-pyrimidinyl)isoxazole a: 5-Amino-3-(3-bromo-4-fluorophenyl)-4-(4-pyrimidinyl)-isoxazole $^1$H-NMR(CDCl$_3$)δ: 9.04(d, J=1.5 Hz, 1H), 8.36(d, J=5.8 Hz, 1H), 7.77(dd, J=1.5 Hz, 6.4 Hz, 1H), 7.48-7.44(m, 1H), 7.28-7.25(m, 1H), 6.88(bs, 2H), 6.71(dd, J=1.5 Hz, 5.8 Hz, 1H).
Mass, m/e: 334(M$^+$), 94(base).

b: 3-(3-Bromo-4-fluorophenyl)-5-(phenylacetylamino)-4-(4-pyrimidinyl)isoxazole $^1$H-NMR(CDCl$_3$)δ: 11.38(s, 1H), 8.51(bs, 1H), 8.41(d, J=5.4 Hz, 1H), 7.71(dd, J=6.6 Hz, 2.3 Hz, 1H), 7.51-7.39(m, 6H), 7.25-7.23(m, 1H), 6.74(dd, J=5.4 Hz, 1.5 Hz, 1H), 3.94(s, 2H).
Mass, m/e: 452(M$^+$), 91(base).

Example 140

3-(3-Bromo-4-fluorophenyl)-5-[(2-chlorophenyl)acetylamino]-4-(4-pyrimidinyl)isoxazole $^1$H-NMR(CDCl$_3$)δ: 10.09(s, 1H), 8.55(bs, 1H), 8.42(d, J=5.4 Hz, 1H), 7.72(dd, J=2.1 Hz, 6.4 Hz, 1H), 7.54-7.52(m, 1H), 7.47-7.39(m, 4H), 7.28-7.24(m, 1H), 6.76(dd, J=1.2 Hz, 5.4 Hz, 1H), 4.06(s, 2H).
Mass, m/e: 486(M$^+$), 125(base).

Example 141

3-(3,4-Dichlorophenyl)-5-(phenylacetylamino)-4-(4-pyrimidinyl)-isoxazole a: 5-Amino-3-(3,4-dichlorophenyl)-4-(4-pyrimidinyl)isoxazole $^1$H-NMR(CDCl$_3$)δ: 9.04(d, J=1.5 Hz, 1H), 8.37(d, J=5.8 Hz, 1H), 7.66(d, J=1.9 Hz, 1H), 7.60(d, J=8.1 Hz, 1H), 7.37(dd, J=1.9 Hz, 8.1 Hz, 1H), 6.89(bs, 2H), 6.72(dd, J=1.5 Hz, 5.8 Hz, 1H).
Mass, m/e: 305(M$^+$), 161(base).

b: 3-(3,4-Dichlorophenyl)-5-(phenylacetylamino)-4-4-pyrimidinyl)-isoxazole $^1$H-NMR(CDCl$_3$)δ: 11.38(s, 1H), 8.51(s, 1H), 8.42(d, J=5.6 Hz, 1H), 7.60-7.57(m, 2H), 7.52-7.39(m, 5H), 7.30(dd, J=1.9 Hz, 8.1 Hz, 1H), 6.75(dd, J=1.5 Hz, 5.6 Hz, 1H), 3.94(s, 2H)
Mass, m/e: 424(M$^+$), 91(base).

Example 142

3-(3,4-Dichlorophenyl)-5-[(2-fluorophenyl)acetylamino]-4-(4-pyrimidinyl)isoxazole $^1$H-NMR(CDCl$_3$)δ: 11.56(s, 1H), 8.63(s, 1H), 8.45(d, J=5.8 Hz, 1H), 7.62-7.59(m, 2H), 7.47-7.41(m, 2H), 7.32(dd, J=1.9 Hz, 8.1 Hz, 1H), 7.28-7.18(m, 2H), 6.79(dd, J=1.5 Hz, 5.8 Hz, 1H), 3.96(s, 2H).
Mass, m/e: 442(M$^+$), 109(base).

Example 143

5-[(2-Chlorophenyl)acetylamino]-3-(3,4-dichlorophenyl)-4-(4-pyrimidinyl)isoxazole $^1$H-NMR(CDCl$_3$)δ: 11.43(s, 1H), 8.56(d, J=1.2 Hz, 1H), 8.43(d, J=5.6 Hz, 1H), 7.61-7.58(m, 2H), 7.55-7.38(m, 4H), 7.32(dd, J=1.9 Hz, 8.1 Hz, 1H), 6.78(dd, J=1.5 Hz, 5.6 Hz, 1H), 4.07(s, 2H).
Mass, m/e: 459(M$^+$+1), 125(base).

Example 144

3-(3,5-Dichlorophenyl)-5-(phenylacetylamino)-4-(4-pyrimidinyl) isoxazole a: 5-Amino-3-(3,5-dichlorophenyl)-4-(4-pyrimidinyl)isoxazole $^1$H-NMR(CDCl$_3$)δ: 9.05(d, J=1.3 Hz, 1H), 8.39(d, J=5.5 Hz, 1H), 7.54(t, J=1.9 Hz, 1H), 7.43(d, J=1.9 Hz, 2H), 6.91(bs, 2H), 6.71(dd, J=1.3 Hz, 5.5 Hz, 1H).
Mass, m/e: 306(M$^+$), 161(base).

b: 3-(3,5-Dichlorophenyl)-5-(phenylacetylamino)-4-(4-pyrimidinyl) isoxazole $^1$H-NMR(CDCl$_3$)δ: 11.39(s, 1H), 8.51(d, J=1.3 Hz, 1H), 8.44(d, J=5.4 Hz, 1H), 7.54(t, J=1.9 Hz, 1H), 7.52-7.39(m, 5H), 7.37(d, J=1.9 Hz, 2H), 6.74(dd, J=1.3 Hz, 5.4 Hz, 1H), 3.94(s, 2H).
Mass, m/e: 424(M$^+$), 91(base).

Example 145

3-(3,5-Dichlorophenyl)-5-[(2-fluorophenyl)acetylamino]-4-(4-pyrimidinyl)isoxazole $^1$H-NMR(CDCl$_3$)δ: 11.57(s, 1H), 8.64(d, J=1.4 Hz, 1H), 8.47(d, J=5.5 Hz, 1H), 7.55(t, J=1.9 Hz, 1H), 7.48-7.40(m, 2H), 7.38(d, J=1.9 Hz, 2H), 7.30-7.24(m, 1H), 7.20(t, J=8.9 Hz, 1H), 6.77(dd, J=1.4 Hz, 5.5 Hz, 1H), 3.97(d, J=1.2 Hz, 2H).
Mass, m/e: 442(M$^+$), 109(base).

Example 146

5-[(2-Chlorophenyl)acetylamino]-3-(3,5-dichlorophenyl)-4-(4-pyrimidinyl)isoxazole $^1$H-NMR(CDCl$_3$)δ: 11.45(s, 1H), 8.56(d, J=1.3 Hz, 1H), 8.45(d, J=5.4 Hz, 1H), 7.56-7.52(m, 2H), 7.50-7.40(m, 3H), 7.38(d, 2H), 6.75(dd, J=1.3 Hz, 5.4 Hz, 1H), 4.07(s, 2H).
Mass, m/e: 458(M$^+$), 125(base).

Example 147

3-(2,6-Dichlorophenyl)-5-(phenylacetylamino)-4-(4-pyrimidinyl)isoxazole a: 5-Amino-3-(2,6-dichlorophenyl)-4-(4-pyrimidinyl)isoxazole $^1$H-NMR(CDCl$_3$)δ: 9.00(d, J=1.4 Hz, 1H), 8.30(d, J=5.6 Hz, 1H), 7.50-7.43(m, 3H), 7.00(bs, 2H), 6.29(dd, J=1.4 Hz, 5.6 Hz, 1H).
Mass, m/e: 306(M$^+$), 271(base).

b: 3-(2,6-Dichlorophenyl)-5-(phenylacetylamino)-4-(4-pyrimidinyl)isoxazole $^1$H-NMR(CDCl$_3$)δ: 11.50(s, 1H), 8.47(s, 1H), 8.35(d, J=5.6 Hz, 1H), 7.52-7.42(m, 8H), 6.34(dd, J=1.5 Hz, 5.6 Hz, 1H), 3.96(s, 2H).
Mass, m/e: 424(M$^+$), 91(base).

Example 148

3-(2,6-Dichlorophenyl)-5-[(2-fluorophenyl)acetylamino]-4-(4-pyrimidinyl)isoxazole $^1$H-NMR(CDCl$_3$)δ: 11.68(s, 1H), 8.60(s, 1H), 8.38(d, J=5.6 Hz, 1H), 7.50-7.43(m, 5H), 7.29-7.19(m, 2H), 6.37(dd, J=1.2 Hz, 5.6 Hz, 1H), 3.99(s, 2H).
Mass, m/e: 442(M$^+$), 109(base).

Example 149

5-[(2-Chlorophenyl)acetylamino]-3-(2,6-dichlorophenyl)-4-(4-pyrimidinyl)isoxazole $^1$H-NMR(CDCl$_3$)δ: 11.55(s, 1H), 8.54(s, 1H), 8.36(d, J=5.6 Hz, 1H), 7.55-7.40(m, 7H), 6.36(dd, J=1.5 Hz, 5.6 Hz, 1H), 4.09(s, 2H).
Mass, m/e: 460(M$^+$), 125(base).

Example 150

5-(Phenylacetylamino)-4-(4-pyrimidinyl)-3-(2,3,4-trifluorophenyl)isoxazole a: 5-Amino-4-(4-pyrimidinyl)-3-(2,3,4-trifluorophenyl)isoxazole $^1$H-NMR(CDCl$_3$)δ: 9.04(d, J=1.5 Hz, 1H), 8.39(d, J=5.8 Hz, 1H), 7.31-7.25(m, 1H), 7.21-7.13(m, 1H), 6.92(bs, 2H), 6.60(dt, J=1.5 Hz, 5.8 Hz, 1H).
Mass, m/e: 292(M$^+$), 147(base).

b: 5-(Phenylacetylamino)-4-(4-pyrimidinyl)-3-(2,3,4-trifluorophenyl)isoxazole $^1$H-NMR(CDCl$_3$)δ: 11.43(s, 1H), 8.50(d, J=1.2 Hz, 1H), 8.44(d, J=5.8 Hz, 1H), 7.52-7.39(m, 5H), 7.30-7.13(m, 2H), 6.64(dt, J=1.2 Hz, 5.8 Hz, 1H), 3.95(s, 2H).
Mass, m/e: 410(M$^+$), 91(base).

Example 151

5-[(2-fluorophenyl)acetylamino)-4-(4-pyrimidinyl)-3-(2,3,4-trifluorophenyl)isoxazole $^1$H-NMR(CDCl$_3$)δ: 11.61(s, 1H), 8.63(d, J=1.2 Hz, 1H), 8.47(d, J=5.4 Hz, 1H), 7.48-7.41(m, 2H), 7.31-7.14(m, 4H), 6.68(dt, J=1.2 Hz, 5.4 Hz, 1H), 3.97(s, 2H)
Mass, m/e: 428(M$^+$), 109(base).

Example 152

5-[(2-Chlorophenyl)acetylamino]-4-(4-pyrimidinyl)-3-(2,3,4-trifluorophenyl)isoxazole ¹H-NMR(CDCl₃)δ: 11.49(s, 1H), 8.56(d, J=1.2 Hz, 1H), 8.46(d, J=5.4 Hz, 1H), 7.55-7.41(m, 3H), 7.31-7.25(m, 2H), 7.20-7.13(m, 1H), 6.67(dt, J=1.2 Hz, 5.4 Hz, 1H), 4.07(s, 2H).
Mass, m/e: 444(M⁺), 125(base).

Example 153

3-(2,4,5-trifluorophenyl)-5-(phenylacetylamino)-4-(4-pyrimidinyl)isoxazole a: 5-Amino-4-(4-pyrimidinyl)-3-(2,4,5-trifluorophenyl)isoxazole ¹H-NMR(CDCl₃)δ: 9.04(d, J=1.5 Hz, 1H), 8.39(d, J=5.4 Hz, 1H), 7.43-7.37(m, 1H), 7.16-7.09(m, 1H), 6.91(bs, 2H), 6.63(dt, J=1.5 Hz, 5.4 Hz, 1H).
Mass, m/e: 292(M⁺), 147(base).

b: 3-(2,4,5-trifluorophenyl)-5-(phenylacetylamino)-4-(4-pyrimidinyl)isoxazole

¹H-NMR(CDCl₃)δ: 11.43(s, 1H), 8.50(bs, 1H), 8.44(d, J=5.4 Hz, 1H), 7.52-7.36(m, 6H), 7.13-7.07(m, 1H), 6.68-6.67(m, 1H), 3.94(s, 2H).
Mass, m/e: 410(M⁺), 91(base).

Example 154

5-[(2-Fluorophenyl)acetylamino]-3-(2,4,5-trifluorophenyl)-4-(4-pyrimidinyl)isoxazole ¹H-NMR(CDCl₃)δ: 11.61(s, 1H), 8.63(d, J=1.2 Hz, 1H), 8.46(d, J=5.4 Hz, 1H), 7.45-7.37(m, 3H), 7.29-7.18(m, 2H), 7.14-7.09(m, 1H), 6.71(dt, J=1.2 Hz, 5.4 Hz, 1H), 3.97(s, 2H).
Mass, m/e: 428(M⁺), 109(base).

Example 155

5-[(2-Chlorophenyl)acetylamino]-3-(2,4,5-trifluorophenyl)-4-(4-pyrimidinyl)isoxazole ¹H-NMR(CDCl₃)δ: 11.48(s, 1H), 8.55(bs, 1H), 8.45(d, J=5.4 Hz, 1H), 7.55-7.36(m, 5H), 7.14-7.08(m, 1H), 6.71-6.69(m, 1H), 4.07(s, 2H).
Mass, m/e: 444(M⁺), 276(base).

Example 156

5-(Phenylacetylamino)-4-(4-pyrimidinyl)-3-(2,4,6-trifluorophenyl)isoxazole a: 5-Amino-4-(4-pyrimidinyl)-3-(2,4,6-trifluorophenyl)isoxazole ¹H-NMR(CDCl₃)δ: 9.03(d, J=1.3 Hz, 1H), 8.38(d, J=5.7 Hz, 1H), 7.07-6.50(m, 5H)
Mass, m/e: 292(M⁺), 147(base).

b: 5-(Phenylacetylamino)-4-(4-pyrimidinyl)-3-(2,4,6-trifluorophenyl)isoxazole

¹H-NMR(CDCl₃)δ: 11.46(s, 1H), 8.49(d, J=1.2 Hz, 1H), 8.42(d, J=5.4 Hz, 1H), 7.52-7.40(m, 5H), 6.89-6.82(m, 2H), 6.61(dd, J=5.4 Hz, 1.2 Hz, 1H), 3.95(s, 2H).
Mass, m/e: 410(M⁺), 91(base).

Example 157

5-[(2-Fluorophenyl)acetylamino]-4-(4-pyrimidinyl)-3-(2,4,6-trifluorophenyl)isoxazole ¹H-NMR(CDCl₃)δ: 11.64(s, 1H), 8.62(bs, 1H), 8.45(d, J=5.4 Hz, 1H), 7.47-7.41(m, 2H), 7.29-7.18(m, 2H), 6.90-6.83(m, 2H), 6.65(dd, J=1.2 Hz, 5.4 Hz, 1H), 3.98(s, 2H).
Mass, m/e: 428(M⁺), 276(base).

Example 158

5-[(2-Chlorophenyl)acetylamino]-3-(2,4,6-trifluorophenyl)-4-(4-pyrimidinyl)isoxazole ¹H-NMR(CDCl₃)δ: 11.52(s, 1H), 8.55(bs, 1H), 8.44(d, J=5.4 Hz, 1H), 7.55-7.53(m, 1H), 7.49-7.47(m, 1H), 7.43-7.40(m, 2H), 6.87(dd, J=7.3 Hz, 8.5 Hz, 2H), 6.64(d, J=5.4 Hz, 1H), 4.08(s, 2H).
Mass, m/e: 444(M⁺), 276(base).

Example 159

5-[(3-Methoxyphenyl)acetylamino]-4-(4-pyrimidinyl)-3-(2,4,6-trifluorophenyl)isoxazole ¹H-NMR(CDCl₃)δ: 11.48(s, 1H), 8.60(d, J=1.5 Hz, 1H), 8.43(d, J=5.4 Hz, 1H), 7.40(t, J=7.9 Hz, 1H), 7.00-6.95(m, 3H), 6.89-6.84(m, 2H), 6.61(dd, J=1.5 Hz, 5.4 Hz, 1H), 3.91(s, 2H), 3.84(s, 3H).
Mass, m/e: 440(M⁺), 148(base).

Example 160

5-(Phenylacetylamino)-4-(4-pyrimidinyl)-3-(3,4,5-trifluorophenyl)isoxazole a: 5-Amino-4-(4-pyrimidinyl)-3-(3,4,5-trifluorophenyl)isoxazole ¹H-NMR(CDCl₃)δ: 9.04(d, J=1.5 Hz, 1H), 8.40(d, J=5.4 Hz, 1H), 7.19(t, J=7.7 Hz, 2H), 6.94(bs, 2H), 6.71(dd, J=1.5 Hz, 5.4 Hz, 1H).
Mass, m/e: 292(M⁺), 147(base).

b: 5-(Phenylacetylamino)-4-(4-pyrimidinyl)-3-(3,4,5-trifluorophenyl)isoxazole

¹H-NMR(CDCl₃)δ: 11.35(bs, 1H), 8.51(d, J=1.2 Hz, 1H), 8.45(d, J=5.4 Hz, 1H), 7.51-7.44(m, 3H), 7.41-7.38(m, 2H), 7.14(t, J=6.2 Hz, 2H), 6.75(dd, J=1.2 Hz, 5.4 Hz, 1H), 3.93(s, 2H).
Mass, m/e: 410(M⁺), 91(base).

Example 161

5-[(2-Fluorophenyl)acetylamino]-4-(4-pyrimidinyl)-3-(3,4,5-trifluorophenyl)isoxazole $^1$H-NMR(CDCl$_3$)δ: 11.54(s, 1H), 8.64(d, J=1.4 Hz, 1H), 8.47(d, J=5.6 Hz, 1H), 7.47-7.39(m, 2H), 7.28-7.13(m, 4H), 6.73(dd, J=1.4 Hz, 5.6 Hz, 1H), 3.96(s, 2H).
Mass, m/e: 428(M$^+$), 109(base).

Example 162

5-[(2-Chlorophenyl)acetylamino]-4-(4-pyrimidinyl)-3-(3,4,5-trifluorophenyl)isoxazole $^1$H-NMR(CDCl$_3$)δ: 11.41(s, 1H), 8.56(d, J=1.2 Hz, 1H), 8.41(d, J=5.4 Hz, 1H), 7.54-7.52(m, 1H), 7.48-7.40(m, 3H), 7.15(t, J=6.6 Hz, 2H), 6.77(dd, J=1.2 Hz, 5.4 Hz, 1H), 4.10(s, 2H).
Mass, m/e: 444(M$^+$), 125(base).

Example 163

3-(2-Methoxyphenyl)-5-(phenylacetylamino)-4-(4-pyrimidinyl)isoxazole a: 5-Amino-3-(2-methoxyphenyl)-4-(4-pyrimidinyl)isoxazole $^1$H-NMR(CDCl$_3$)δ: 8.99(d, J=1.5 Hz, 1H), 8.26(d, J=5.8 Hz, 1H), 7.51(td, J=1.7 Hz, 7.7 Hz, 1H), 7.42(dd, J=1.7 Hz, 1H), 7.09(ddd, J=1.0 Hz, 7.7 Hz, 15.7 Hz, 1H), 7.02(d, J=7.7 Hz, 1H), 6.83(bs, 2H), 6.55(dd, J=1.5 Hz, 5.8 Hz, 1H).
Mass, m/e: 268(M$^+$), 123(base).

b: 3-(2-Methoxyphenyl)-5-(phenylacetylamino)-4-(4-pyrimidinyl)isoxazole $^1$H-NMR(CDCl$_3$)δ: 11.46(s, 1H), 8.47(bs, 1H), 8.31(d, J=5.7 Hz, 1H), 7.55-7.22(m, 6H), 7.16-7.05(m, 2H), 6.98(d, J=8.5 Hz, 1H), 6.60(dd, J=1.5 Hz, 5.7 Hz, 1H), 3.94(s, 2H), 3.62(s, 3H).
Mass, m/e: 386(M$^+$), 252(base).

Example 164

5-[(2-Fluorophenyl)acetylamino]-3-(2-methoxyphenyl)-4-(4-pyrimidinyl)isoxazole $^1$H-NMR(CDCl$_3$)δ: 11.63(s, 1H), 8.59(s, 1H), 8.33(d, J=5.5 Hz, 1H), 7.55-7.49(m, 1H), 7.47-7.39(m, 3H), 7.29-7.16(m, 2H), 7.09(td, J=1.0 Hz, 7.3 Hz, 1H), 6.99(d, J=8.1 Hz, 1H), 6.63(dd, J=1.3 Hz, 5.5 Hz, 1H), 3.97(s, 2H), 3.63(s, 3H).
Mass, m/e: 404(M$^+$), 252(base).

Example 165

5-[(2-Chlorophenyl)acetylamino]-3-(2-methoxyphenyl)-4-(4-pyrimidinyl)isoxazole $^1$H-NMR(CDCl$_3$)δ: 11.51(s, 1H), 8.52(s, 1H), 8.32(d, J=5.5 Hz, 1H), 7.55-7.45(m, 3H), 7.44-7.38(m, 3H), 7.09(td, J=0.9 Hz, 7.3 Hz, 1H), 6.99(d, J=8.1 Hz, 1H), 6.63(dd, J=1.3 Hz, 5.5 Hz, 1H), 4.07(s, 2H).
Mass, m/e: 420(M$^+$), 252(base).

Example 166

3-(3-Methoxyphenyl)-5-(phenylacetylamino)-4-(4-pyrimidinyl)isoxazole a: 5-Amino-3-(3-methoxyphenyl)-4-(4-pyrimidinyl)isoxazole $^1$H-NMR(CDCl$_3$)δ: 9.01(d, J=1.3 Hz, 1H), 8.30(d, J=5.7 Hz, 1H), 7.42(t, J=7.9 Hz, 1H), 7.11(m, 3H), 6.87(bs, 2H), 6.76(dd, J=1.3 Hz, 5.7 Hz, 1H), 3.83(s, 3H).
Mass, m/e: 268(M$^+$), 77(base).

b: 3-(3-Methoxyphenyl)-5-(phenylacetylamino)-4-(4-pyrimidinyl)isoxazole $^1$H-NMR(CDCl$_3$)δ: 11.42(s, 1H), 8.49(s, 1H), 8.35(d, J=5.5 Hz, 1H), 7.52-7.37(m, 6H), 7.10-6.95(m, 3H), 6.78(dd, J=1.3 Hz, 5.5 Hz, 1H), 3.94(s, 2H), 3.81(s, 3H).
Mass, m/e: 386(M$^+$), 91(base).

Example 167

5-[(2-Fluorophenyl)acetylamino]-3-(3-methoxyphenyl)-4-(4-pyrimidinyl)isoxazole $^1$H-NMR(CDCl$_3$)δ: 11.60(s, 1H), 8.61(s, 1H), 8.37(d, J=5.7 Hz, 1H), 7.47-7.38(m, 3H), 7.29-7.16(m, 2H), 7.09-6.97(m, 3H), 6.81(dd, J=1.3 Hz, 5.7 Hz, 1H), 3.97(s, 2H), 3.82(s, 3H).
Mass, m/e: 404(M$^+$−1), 252(base).

Example 168

5-[(2-Chlorophenyl)acetylamino]-3-(3-methoxyphenyl)-4-(4-pyrimidinyl)isoxazole $^1$H-NMR(CDCl$_3$)δ: 11.48(s, 1H), 8.56-8.50(bs, 1H), 8.36(d, J=5.6 Hz, 1H), 7.56-7.37(m, 5H), 7.09(m, 3H), 6.79(dd, J=1.3 Hz, 5.6 Hz, 1H), 4.07(s, 2H), 3.81(s, 3H).
Mass, m/e: 420(M$^+$), 252(base).

Example 169

3-(4-Methoxyphenyl)-5-(phenylacetylamino)-4-(4-pyrimidinyl)isoxazole a: 5-Amino-3-(4-methoxyphenyl)-4-(4-pyrimidinyl)isoxazole $^1$H-NMR(CDCl$_3$)δ: 9.01(d, J=1.5 Hz, 1H), 8.30(d, J=5.8 Hz, 1H), 7.46-7.43(m, 2H), 7.04-7.00(m, 2H), 6.84(bs, 2H), 6.79(dd, J=1.5 Hz, 5.8 Hz, 1H), 3.88(s, 3H).
Mass, m/e: 268(M$^+$), 123(base).

b: 3-(4-Methoxyphenyl)-5-(phenylacetylamino)-4-(4-pyrimidinyl)isoxazole $^1$H-NMR(CDCl$_3$)δ: 11.40(s, 1H), 8.48(s, 1H), 8.35(d, J=5.4 Hz, 1H), 7.50-7.36(m, 7H), 7.02-6.98(m, 2H), 6.82(dd, J=1.5 Hz, 5.4 Hz, 1H), 3.93(s, 2H), 3.87(s, 3H)
Mass, m/e: 386(M$^+$), 91(base). .

Example 170

5-[(2-Fluorophenyl)acetylamino]-3-(4-methoxyphenyl)-4-(4-pyrimidinyl)isoxazole $^1$H-NMR(CDCl$_3$)δ: 11.57(s, 1H), 8.60(s, 1H), 8.38(d, J=5.4 Hz, 1H), 7.46-7.38(m, 4H), 7.27-7.17(m, 2H), 7.03-6.99(m, 2H), 6.83(dd, J=1.5 Hz, 5.4 Hz, 1H), 3.96(s, 2H), 3.87(s, 3H).
Mass, m/e: 404(M$^+$), 109(base).

Example 171

5-[(2-Chlorophenyl)acetylamino]-3-(4-methoxyphenyl)-4-(4-pyrimidinyl)isoxazole $^1$H-NMR(CDCl$_3$)δ: 11.45(s, 1H), 8.53(s, 1H), 8.36(d, J=5.4 Hz, 1H), 7.54-7.52(m, 1H), 7.48-7.46(m, 1H), 7.42-7.38(m, 4H), 7.03-7.00(m, 2H), 6.84(dd, J=1.5 Hz, 5.4 Hz, 1H), 4.06(s, 2H), 3.87(s, 3H).
Mass, m/e: 420(M$^+$), 135(base).

Example 172

3-(2-Fluoro-4-methoxyphenyl)-5-(phenylacetylamino)-4-(4-pyrimidinyl)isoxazole a: 5-Amino-3-(2-fluoro-4-methoxyphenyl)-4-(4-pyrimidinyl)isoxazole $^1$H-NMR(CDCl$_3$)δ: 8.98(d, J=1.5 Hz, 1H), 8.41(d, J=5.8 Hz, 1H), 8.31(bs, 2H), 7.47(t, J=8.5 Hz, 1H), 7.06(dd, J=2.3 Hz, 11.9 Hz, 1H), 6.97(dd, J=2.3 Hz, 8.5 Hz, 1H), 6.57(td, J=1.5 Hz, 5.8 Hz, 1H).
Mass, m/e: 286(M$^+$), 141(base).

b: 3-(2-Fluoro-4-methoxyphenyl)-5-(phenylacetylamino)-4-(4-pyrimidinyl)isoxazole $^1$H-NMR(CDCl$_3$)δ: 11.44(bs, 1H), 8.47(s, 1H), 8.38(d, J=5.8 Hz, 1H), 7.51-7.38(m, 6H), 6.83(dd, J=2.7 Hz, 8.5 Hz, 1H), 6.75-6.71(m, 2H), 3.93(s, 2H), 3.86(s, 3H).
Mass, m/e: 404(M$^+$), 91(base).

Example 173

3-(2-Fluoro-4-methoxyphenyl)-5-[(2-fluorophenyl)acetylamino]-4-(4-pyrimidinyl)isoxazole $^1$H-NMR(CDCl$_3$)δ: 11.62(bs, 1H), 8.59(s, 1H), 8.41(d, J=5.8 Hz, 1H), 7.45-7.39(m, 3H), 7.27-7.24(m, 1H), 7.19(t, J=9.3 Hz, 1H), 6.84(dd, J=2.3 Hz, 8.5 Hz, 1H), 6.77-6.72(m, 2H), 3.96(s, 2H), 3.87(s, 3H).
Mass, m/e: 422(M$^+$), 270(base).

Example 174

5-[(2-Chlorophenyl)acetylamino]-3-(2-fluoro-4-methoxyphenyl)-4-(4-pyrimidinyl)isoxazole $^1$H-NMR(CDCl$_3$)δ: 11.49(s, 1H), 8.52(s, 1H), 8.39(d, J=5.8 Hz, 1H), 7.54-7.51(m, 1H), 7.48-7.46(m, 1H), 7.43-7.39(m, 3H), 6.84(dd, J=2.3 Hz, 8.5 Hz, 1H), 6.76-6.72(m, 2H), 4.06(s, 2H), 3.87(s, 3H).
Mass, m/e: 438(M$^+$), 270(base).

Example 175

3-(2-Fluoro-4-methoxyphenyl)-5-[(2-methylphenyl)acetylamino]-4-(4-pyrimidinyl)isoxazole $^1$H-NMR(CDCl$_3$)δ: 11.40(bs, 1H), 8.40(d, J=1.2 Hz, 1H), 8.37(d, J=5.4 Hz, 1H), 7.42-7.31(m, 5H), 6.83(dd, J=1.9 Hz, 8.1 Hz, 1H), 6.75-6.70(m, 2H), 3.92(s, 2H), 3.86(s, 3H), 2.36(s, 3H).
Mass, m/e: 418(M$^+$), 270(base).

Example 176

3-(2-Fluoro-4-methoxyphenyl)-5-[(3-methylphenyl)acetylamino]-4-(4-pyrimidinyl)isoxazole $^1$H-NMR(CDCl$_3$)δ: 11.42(bs, 1H), 8.46(s, 1H), 8.38(d, J=5.8 Hz, 1H), 7.40(t, J=8.5 Hz, 2H), 7.37(t, J=7.3 Hz, 1H), 7.26(d, J=7.3 Hz, 1H), 7.21(d, J=7.3 Hz, 1H), 6.83(dd, J=2.7 Hz, 8.9 Hz, 1H), 6.75-6.71(m, 2H), 3.88(s, 2H), 3.86(s, 3H), 2.39(s, 3H).
Mass, m/e: 418(M$^+$), 270(base).

Example 177

5-[(2,5-Dimethylphenyl)acetylamino]-3-(2-fluoro-4-methoxyphenyl)-4-(4-pyrimidinyl)isoxazole $^1$H-NMR(CDCl$_3$)δ: 11.36(bs, 1H), 8.37(s, 1H), 8.37(d, J=5.4 Hz, 1H), 7.40(t, J=8.1 Hz, 1H), 7.20(s, 2H), 7.15(s, 1H), 6.83(dd, J=2.3 Hz, 8.5 Hz, 1H), 6.75-6.71(m, 2H), 3.87(s, 2H), 3.86(s, 3H), 2.38(s, 3H), 2.31(s, 3H).
Mass, m/e: 432(M$^+$), 270(base).

Example 178

3-(4-Ethylphenyl)-5-(phenylacetylamino)-4-(4-pyrimidinyl)isoxazole a: 5-Amino-3-(4-ethoxyphenyl)-4-(4-pyrimidinyl)isoxazole $^1$H-NMR(CDCl$_3$)δ: 9.01(d, J=1.5 Hz, 1H), 8.30(d, J=5.8 Hz, 1H), 7.45-7.41(m, 2H), 7.02-6.99(m, 2H), 6.83(bs, 2H), 6.79(dd, J=1.5 Hz, 5.8 Hz, 1H), 4.11(q, J=6.9 Hz, 2H), 1.46(t, J=6.9 Hz, 3H).
Mass, m/e: 282(M$^+$), 137(base).

b: 3-(4-Ethylphenyl)-5-(Phenylacetylamino)-4-(4-pyrimidinyl)isoxazole $^1$H-NMR(CDCl$_3$)δ: 11.39(s, 1H), 8.48(s, 1H), 8.34(d, J=5.8 Hz, 1H), 7.50-7.35(m, 7H), 7.00-6.97(m, 2H), 6.82(dd, J=1.5 Hz, 5.8 Hz, 1H), 4.09(q, J=6.9 Hz, 2H), 3.92(s, 2H), 1.45(t, J=6.9 Hz, 3H).
Mass, m/e: 400(M$^+$), 266(base).

Example 179

3-(4-Ethoxyphenyl)-5-[(2-fluorophenyl)acetylamino]-4-(4-pyrimidinyl)isoxazole $^1$H-NMR(CDCl$_3$)δ: 11.57(s, 1H), 8.60(s, 1H), 8.37(d, J=5.4 Hz, 1H), 7.46-7.36(m, 4H), 7.27-7.17(m, 2H), 7.01-6.97(m, 2H), 6.85(dd, J=1.5 Hz, 5.4 Hz, 1H), 4.09(q, J=6.9 Hz, 2H), 3.92(s, 2H), 1.45(t, J=6.9 Hz, 3H).
Mass, m/e: 418(M$^+$), 266(base).

Example 180

3-(4-Ethoxyphenyl)-5-[(2-chlorophenyl)acetylamino]-4-(4-pyrimidinyl)isoxazole $^1$H-NMR(CDCl$_3$)δ: 11.45(s, 1H), 8.53(s, 1H), 8.36(d, J=5.4 Hz, 1H), 7.54-7.36(m, 6H), 7.01-6.97(m, 2H), 6.85(dd, J=1.5 Hz, 5.4 Hz, 1H), 4.12-4.06(m, 4H), 1.45(t, J=6.9 Hz, 3H).
Mass, m/e: 434(M$^+$), 266(base).

Example 181

3-(3-Benzyloxyphenyl)-5-(phenylacetylamino)-4-(4-pyrimidinyl)isoxazole a: 5-Amino-3-(3-benzyloxyphenyl)-4-(4-pyrimidinyl)isoxazole $^1$H-NMR(CDCl$_3$)δ: 8.99(d, J=1.5 Hz, 1H), 8.29(d, J=5.6 Hz, 1H), 7.43-7.29(m, 7H), 7.11-7.07(m, 2H), 6.95(bs, 2H), 6.45(dd, J=1.5 Hz, 5.6 Hz, 1H), 5.06(s, 2H).
Mass, m/e: 344(M$^+$), 91(base).

b: 3-(3-Benzyloxyphenyl)-5-(phenylacetylamino)-4-(4-pyrimidinyl)isoxazole $^1$H-NMR(CDCl$_3$)δ: 11.48(bs, 1H), 8.46(d, J=1.4 Hz, 1H), 8.33(d, J=5.6 Hz, 1H), 7.51-7.29(m, 12H), 7.09(dd, J=3.1 Hz, 8.9 Hz, 1H), 7.04(d, J=3.1 Hz, 1H), 6.50(dd, J=1.4 Hz, 5.6 Hz, 1H), 5.05(s, 2H), 3.94(s, 2H).
Mass, m/e: 461(M$^+$), 91(base).

Example 182

3-(3-Benzyloxyphenyl)-5-[(2-chloro-4-fluorophenyl)acetylamino]-4-(4-pyrimidinyl)isoxazole $^1$H-NMR(CDCl$_3$)δ: 11.56(bs, 1H), 8.69(s, 1H), 8.39(d, J=5.6 Hz, 1H), 7.48-7.26(m, 9H), 7.14-7.09(m, 2H), 7.06(d, J=3.1 Hz, 1H), 6.55(dd, J=1.5 Hz, 5.6 Hz, 1H), 5.06(s, 2H), 4.05(s, 2H).
Mass, m/e: 513(M$^+$), 91(base).

Example 183

3-(3-Benzyloxyphenyl)-5-[(2,4-dichlorophenyl)acetylamino]-4-(4-pyrimidinyl)isoxazole $^1$H-NMR(CDCl$_3$)δ: 11.57(bs, 1H), 8.68(s, 1H), 8.39(d, J=5.6 Hz, 1H), 7.54(d, J=1.9 Hz, 1H), 7.43-7.31(m, 9H), 7.10(dd, J=3.1 Hz, 8.9 Hz, 1H), 7.06(d, J=3.1 Hz, 1H), 6.56(dd, J=1.5 Hz, 5.6 Hz, 1H), 5.06(s, 2H), 4.05(s, 2H).
Mass, m/e: 529(M$^+$), 91(base).

Example 184

3-(3-Benzyloxyphenyl)-5-[(2,6-dichlorophenyl)acetylamino]-4-(4-pyrimidinyl)isoxazole $^1$H-NMR(CDCl$_3$)δ: 11.55(bs, 1H), 8.58(s, 1H), 8.37(d, J=5.6 Hz, 1H), 7.49(d, J=8.1 Hz, 2H), 7.42-7.29(m, 8H), 7.10(dd, J=3.1 Hz, 8.9 Hz, 1H), 7.06(d, J=3.1 Hz, 1H), 6.55(dd, J=1.2 Hz, 5.6 Hz, 1H), 5.06(s, 2H), 4.32(s, 2H).
Mass, m/e: 529(M$^+$), 91(base).

Example 185

3-(2,3-Dimethoxyphenyl)-5-(phenylacetylamino)-4-(4-pyrimidinyl)isoxazole a: 5-Amino-3-(2,3-dimethoxyphenyl)-4-(4-pyrimidinyl)isoxazole $^1$H-NMR(CDCl$_3$)δ: 8.97(d, J=1.3 Hz, 1H), 8.26(d, J=5.8 Hz, 1H), 7.19(t, J=7.8 Hz, 1H), 7.10(dd, J=1.5 Hz, 8.5 Hz, 1H), 6.97(dd, J=1.5 Hz, 7.8 Hz, 1H), 6.86(bs, 2H), 6.56(dd, J=1.3 Hz, 5.8 Hz, 1H), 3.93(s, 3H), 3.72(s, 3H).
Mass, m/e: 298(M$^+$), 267(base).

b: 3-(2,3-Dimethoxyphenyl)-5-(phenylacetylamino)-4-(4-Pyrimidinyl)isoxazole $^1$H-NMR(CDCl$_3$)δ: 11.51(s, 1H), 8.44(s, 1H), 8.31(d, J=5.7 Hz, 1H), 7.52-7.40(m, 5H), 7.18(t, J=7.8 Hz, 1H), 7.10(dd, J=1.5 Hz, 8.5 Hz, 1H), 6.93(dd, J=1.5 Hz, 7.8 Hz, 1H), 6.61(dd, J=1.5 Hz, 5.7 Hz, 1H), 3.95(s, 2H), 3.91(s, 3H), 3.65(s, 3H).
Mass, m/e: 416(M$^+$), 91(base).

Example 186

3-(2,3-Dimethoxyphenyl)-5-[(2-fluorophenyl)acetylamino]-4-(4-pyrimidinyl)isoxazole $^1$H-NMR(CDCl$_3$)δ: 11.69(s, 1H), 8.56(s, 1H), 8.34(d, J=5.5 Hz, 1H), 7.47-7.40(m, 2H), 7.31-7.15(m, 4H), 6.94(dd, J=1.5 Hz, 7.3 Hz, 1H), 6.64(dd, J=1.5 Hz, 5.5 Hz, 1H), 3.98(s, 2H), 3.92(s, 3H), 3.66(s, 3H).
Mass, m/e: 434(M$^+$), 109(base).

Example 187

3-(2,3-Dimethoxyphenyl)-5-[(2-chlorophenyl)acetylamino]-4-(4-pyrimidinyl)isoxazole $^1$H-NMR(CDCl$_3$)δ: 11.32(s, 1H), 8.49(s, 1H), 8.32(d, J=5.4 Hz, 1H), 7.55-7.38(m, 4H), 7.19(t, J=8.5 Hz, 1H), 7.10(dd, J=1.5 Hz, 8.5 Hz, 1H), 6.94(dd, J=1.5 Hz, 7.2 Hz, 1H), 6.64(dd, J=1.5 Hz, 5.4 Hz, 1H), 4.08(s, 2H), 3.92(s, 3H), 3.66(s, 3H).
Mass, m/e: 450(M$^+$), 282(base).

Example 188

3-(3,4-Dimethoxyphenyl)-5-(phenylacetylamino)-4-(4-pyrimidinyl)isoxazole a: 5-Amino-3-(3,4-dimethoxyphenyl)-4-(4-pyrimidinyl)isoxazole $^1$H-NMR(CDCl$_3$)δ: 9.02(d, J=1.3 Hz, 1H), 8.31(d, J=5.5 Hz, 1H), 7.08(dd, J=1.9 Hz, 8.4 Hz, 1H), 7.02(s, 1H), 7.00(t, J=8.4 Hz, 1H), 6.85(bs, 2H), 6.81(dd, J=1.3 Hz, 5.5 Hz, 1H), 3.96(s, 3H), 3.87(s, 3H).
Mass, m/e: 298(M$^+$), 153(base).

b: 3-(3,4-Dimethoxyphenyl)-5-(phenylacetylamino)-4-(4-pyrimidinyl)isoxazole $^1$H-NMR(CDCl$_3$)δ: 11.40(s, 1H), 8.50(bs, 1H), 8.36(d, J=5.7 Hz, 1H), 7.52-7.38(m, 5H), 7.04-6.93(m, 3H), 6.84(dd, J=1.3 Hz, 5.7 Hz, 1H), 3.94(s, 3H), 3.94(s, 2H), 3.84(s, 3H)
Mass, m/e: 416(M$^+$), 91(base).

Example 189

3-(3,4-Dimethoxyphenyl)-5-[(2-fluorophenyl)acetylamino]-4-(4-pyrimidinyl)isoxazole $^1$H-NMR(CDCl$_3$)δ: 11.58(s, 1H), 8.61(s, 1H), 8.38(d, J=5.5 Hz, 1H), 7.47-7.39(m, 2H), 7.30-7.16(m, 2H), 7.03(dd, J=1.9 Hz, 8.1 Hz, 1H), 6.99-6.95(m, 2H), 6.87(dd, J=1.3 Hz, 5.5 Hz, 1H), 3.97(s, 2H), 3.95(s, 3H), 3.85(s, 3H).
Mass, m/e: 434(M$^+$), 282(base).

Example 190

5-[(2-Chlorophenyl)acetylamino]-3-(3,4-dimethoxyphenyl)-4-(4-pyrimidinyl)isoxazole $^1$H-NMR(CDCl$_3$)δ: 11.46(s, 1H), 8.54(s, 1H), 8.37(d, J=5.5 Hz, 1H), 7.55-7.50(m, 1H), 7.49-7.45(m, 1H), 7.45-7.38(m, 2H), 7.02(dd, J=1.7 Hz, 8.3 Hz, 1H), 6.99-6.94(m, 2H), 6.86(dd, J=5.5 Hz, 1H), 4.07(s, 2H), 3.95(s, 3H), 3.84(s, 3H).
Mass, m/e: 450(M$^+$), 282(base).

Example 191

3-(2,3-Methylenedioxyphenyl)-5-(phenylacetylamino)-4-(4-pyrimidinyl)isoxazole a: 5-Amino-3-(2,3-methylenedioxyphenyl)-4-(4-pyrimidinyl)isoxazole $^1$H-NMR(CDCl$_3$)δ: 9.02(d, J=1.5 Hz, 1H), 8.39(d, J=5.8 Hz, 1H), 7.04-6.91(m, 1H), 6.83-6.81(m, 2H), 6.87(bs, 2H), 6.63(dd, J=1.5 Hz, 5.8 Hz, 1H), 5.95(s, 2H).
Mass, m/e: 282(M$^+$), 137(base).

b: 3-(2,3-Methylenedioxyphenyl)-5-(phenylacetylamino)-4-(4-pyrimidinyl)isoxazole $^1$H-NMR(CDCl$_3$)δ: 11.43(s, 1H), 8.50(bs, 1H), 8.41(d, J=5.8 Hz, 1H), 7.51-7.40(m, 5H), 6.99-6.95(m, 3H), 6.84(dd, J=1.4 Hz, 5.8 Hz, 1H), 5.89(s, 2H), 3.94(s, 2H).
Mass, m/e: 400(M$^+$), 91(base).

Example 192

5-[(2-Chlorophenyl)acetylamino]-3-(2,3-methylenedioxyphenyl)-4-(4-pyrimidinyl)isoxazole $^1$H-NMR(CDCl$_3$)δ: 11.48(s, 1H), 8.54(bs, 1H), 8.42(d, J=5.4 Hz, 1H), 7.54-7.52(m, 1H), 7.48-7.46(m, 1H), 7.42-7.39(m, 2H), 6.99-6.96(m, 3H), 6.87(dd, J=1.5 Hz, 5.4 Hz, 1H), 5.89(s, 2H), 4.07(s, 2H).
Mass, m/e: 434(M$^+$), 266(base).

Example 193

3-(3,4-Methylenedioxyphenyl)-5-(phenylacetylamino)-4-(4-pyrimidinyl)isoxazole a: 5-Amino-3-(3,4-methylenedioxyphenyl)-4-(4-pyrimidinyl)isoxazole $^1$H-NMR(CDCl$_3$)δ: 9.02(d, J=1.1 Hz, 1H), 8.34(d, J=5.7 Hz, 1H), 7.05-6.70(m, 6H), 6.06(s, 2H).
Mass, m/e: 282(M$^+$), 137(base).

b: 3-(3,4-Methylenedioxyphenyl)-5-(phenylacetylamino)-4-(4-pyrimidinyl)isoxazole $^1$H-NMR(CDCl$_3$)δ: 11.39(s, 1H), 8.48(s, 1H), 8.38(d, J=5.8 Hz, 1H), 7.52-7.38(m, 5H), 6.97-6.85(m, 4H), 6.05(s, 2H), 3.93(s, 1H).
Mass, m/e: 400(M$^+$), 91(base).

Example 194

3-(3,4-Ethylenedioxyphenyl)-5-[(2-fluorophenyl)acetylamino]-4-(4-pyrimidinyl)isoxazole a: 5-Amino-3-(3,4-ethylenedioxyphenyl)-4-(4-pyrimidinyl)isoxazole $^1$H-NMR(CDCl$_3$)δ: 9.03(d, J=1.2 Hz, 1H), 8.32(d, J=5.8 Hz, 1H), 7.04(bs, 1H), 6.98(d, J=1.2 Hz, 2H), 6.86(dd, J=1.2 Hz, 5.6 Hz, 1H), 6.82(bs, 2H), 4.35-4.30(m, 4H).
Mass, m/e: 296(M$^+$), 151(base).

b: 3-(3,4-Ethylenedioxyphenyl)-5-[(2-fluorophenyl)acetylamino]-4-(4-pyrimidinyl)isoxazole $^1$H-NMR(CDCl$_3$)δ: 11.57(s, 1H), 8.60(s, 1H), 8.40(d, J=5.4 Hz, 1H), 7.46-7.40(m, 2H), 7.28-7.17(m, 2H), 7.00-6.91(m, 4H), 4.34-4.28(m, 4H), 3.96(s, 2H).
Mass, m/e: 432(M$^+$), 280(base).

Example 195

3-(2-Methylphenyl)-5-(phenylacetylamino)-4-(4-pyrimidinyl)isoxazole a: 5-Amino-3-(2-methylphenyl)-4-(4-pyrimidinyl)isoxazole $^1$H-NMR(CDCl$_3$)δ: 8.99(d, J=1.5 Hz, 1H), 8.23(d, J=5.7 Hz, 1H), 7.46-7.43(m, 1H), 7.36-7.29(m, 3H), 6.90(bs, 2H), 6.34(dd, J=1.5 Hz, 5.7 Hz, 1H), 2.22(s, 3H).
Mass, m/e: 252(M$^+$), 130(base).

b: 3-(2-Methylphenyl)-5-(phenylacetylamino)-4-(4-pyrimidinyl)isoxazole $^1$H-NMR(CDCl$_3$)δ: 11.50(s, 1H), 8.46(bs, 1H), 8.28(d, J=5.7 Hz, 1H), 7.52-7.40(m, 6H), 7.34-7.25(m, 3H), 6.39(dd, J=1.5 Hz, 5.7 Hz, 1H), 3.96(s, 2H), 2.13(s, 3H).
Mass, m/e: 370(M$^+$), 91(base).

Example 196

5-[(2-Fluorophenyl)acetylamino]-3-(2-methylphenyl)-4-(4-pyrimidinyl)isoxazole $^1$H-NMR(CDCl$_3$)δ: 11.67(s, 1H), 8.58(s, 1H), 8.31(d, J=1.5 Hz, 1H), 7.48-7.40(m, 3H), 7.35-7.18(m, 5H), 6.42(dd, J=1.5 Hz, 5.4 Hz, 1H), 3.99(d, J=0.8 Hz, 2H), 2.14(s, 3H).
Mass, m/e: 388(M$^+$), 236(base).

Example 197

5-[(2-Chlorophenyl)acetylamino]-3-(2-methylphenyl)-4-(4-pyrimidinyl)isoxazole $^1$H-NMR(CDCl$_3$)δ: 11.55(s, 1H), 8.51(s, 1H), 8.29(d, J=5.7 Hz, 1H), 7.56-7.19(m, 8H), 6.41(dd, J=1.3 Hz, 5.7 Hz, 1H), 4.09(s, 2H), 2.14(s, 3H)
Mass, m/e: 404(M$^+$), 236(base). .

Example 198

3-(3-Methylphenyl)-5-(phenylacetylamino)-4-(4-pyrimidinyl)isoxazole a: 5-Amino-3-(3-methylphenyl)-4-(4-pyrimidinyl) isoxazole $^1$H-NMR(CDCl$_3$)δ: 9.00(d, J=1.6 Hz, 1H), 8.28(d, J=5.6 Hz, 1H), 7.40-7.28(m, 4H), 6.86(bs, 2H), 6.73(dd, J=1.6 Hz, 5.6 Hz, 1H), 2.41(s, 3H).
Mass, m/e: 252(M$^+$), 91(base).

b: 3-(3-Methylphenyl)-5-(phenylacetylamino)-4-(4-pyrimidinyl)isoxazole $^1$H-NMR(CDCl$_3$)δ: 11.42(bs, 1H), 8.48(s, 1H), 8.32(d, J=5.6 Hz, 1H), 7.48-7.21(m, 9H), 6.75(dd, J=1.5 Hz, 5.6 Hz, 1H), 3.93(s, 2H), 2.39(s, 3H).
Mass, m/e: 370(M$^+$), 91(base).

Example 199

5-[(2-Fluorophenyl)acetylamino]-3-(3-methylphenyl)-4-(4-pyrimidinyl)isoxazole $^1$H-NMR(CDCl$_3$)δ: 11.60(s, 1H), 8.60(s, 1H), 8.35(d, J=5.4 Hz, 1H), 7.45-7.17(m, 8H), 6.79(dd, J=1.5 Hz, 5.4 Hz, 1H), 3.96(s, 2H), 2.39(s, 3H).
Mass, m/e: 388(M$^+$), 236(base).

Example 200

5-[(3-Fluorophenyl)acetylamino]-3-(3-methylphenyl)-4-(4-pyrimidinyl)isoxazole $^1$H-NMR(CDCl$_3$)δ: 11.45(s, 1H), 8.65(s, 1H), 8.36(d, J=5.4 Hz, 1H), 7.47-7.33(m, 3H), 7.29(s, 1H), 7.24-7.13(m, 4H), 6.79(dd, J=1.2 Hz, 5.4 Hz, 1H), 3.94(s, 2H), 2.40(s, 3H).
Mass, m/e: 388(M$^+$), 236(base).

Example 201

5-[(2-Chlorophenyl)acetylamino]-3-(3-methylphenyl)-4-(4-pyrimidinyl)isoxazole $^1$H-NMR(CDCl$_3$)δ: 8.52(s, 1H), 8.34(d, J=5.4 Hz, 1H), 7.54-7.20(m, 8H), 6.78(dd, J=1.5 Hz, 5.4 Hz, 1H), 4.07(s, 2H), 2.39(s, 3H).
Mass, m/e: 404(M$^+$), 236(base).

Example 202

5-[(2-Bromophenyl)acetylamino]-3-(3-methylphenyl)-4-(4-pyrimidinyl)isoxazole $^1$H-NMR(CDCl$_3$)δ: 11.45(bs, 1H), 8.51(s, 1H), 8.34(d, J=5.5 Hz, 1H), 7.41(d, J=8.1 Hz, 1H), 7.49-7.31(m, 5H), 7.29(s,1H), 7.23(d, J=7.3 Hz, 1H), 6.77(dd, J=1.2 Hz, 5.5 Hz, 1H), 4.09(s, 2H), 2.39(s, 3H).
Mass, m/e: 448(M$^+$), 236(base).

Example 203

5-[(2-Iodophenyl)acetylamino]-3-(3-methylphenyl)-4-(4-pyrimidinyl)isoxazole $^1$H-NMR(CDCl$_3$)δ: 11.40(bs, 1H), 8.49(s, 1H), 8.33(d, J=5.6 Hz, 1H), 8.00(d, J=7.7 Hz, 1H), 7.48(d, J=3.9 Hz, 2H), 7.39-7.32(m, 2H), 7.29(s, 1H), 7.24(d, J=9.3 Hz, 1H), 7.18-7.12(m, 1H), 6.77(dd, J=1.2 Hz, 5.6 Hz, 1H), 4.12(s, 2H), 2.39(s, 3H).
Mass, m/e: 496(M$^+$), 236(base).

Example 204

5-[(2,4-Difluorophenyl)acetylamino]-3-(3-methylphenyl)-4-(4-pyrimidinyl)isoxazole $^1$H-NMR(CDCl$_3$)δ: 11.62(bs, 1H), 8.78(s, 1H), 8.39(d, J=5.6 Hz, 1H), 7.42-7.34(m, 3H), 7.30(s, 1H), 7.24(d, J=6.6 Hz, 1H), 7.00-6.91(m, 2H), 6.82(dd, J=1.6 Hz, 5.6 Hz, 1H), 3.94(s, 2H), 2.40(s, 3H).
Mass, m/e: 406(M$^+$), 236(base).

Example 205

5-[(2,5-Difluorophenyl)acetylamino]-3-(3-methylphenyl)-4-(4-pyrimidinyl)isoxazole $^1$H-NMR(CDCl$_3$)δ: 11.65(bs, 1H), 8.79(s, 1H), 8.39(d, J=5.6 Hz, 1H), 7.40-7.34(m, 2H), 7.30(bs, 1H), 7.25-7.24(m, 1H), 7.17-7.05(m, 3H), 6.82(dd, J=1.2 Hz, 5.6 Hz, 1H), 3.95 (s, 2H), 2.40(s, 3H).
Mass, m/e: 406(M$^+$), 236(base).

Example 206

5-[(2-Chloro-4-fluorophenyl)acetylamino]-3-(3-methylphenyl)-4-(4-pyrimidinyl)isoxazole $^1$H-NMR(CDCl$_3$)δ: 11.50(s, 1H), 8.70(s, 1H), 8.38(d, J=5.6 Hz, 1H), 7.45(dd, J=5.8 Hz, 8.5 Hz, 1H), 7.40-7.33(m, 2H), 7.30-7.23(m, 3H), 7.11(dt, J=2.3 Hz, 7.7 Hz, 1H), 6.81 (dd, J=1.5 Hz, 5.6 Hz, 1H), 4.04(s, 2H), 2.40(s, 3H).
Mass, m/e: 422(M$^+$), 236(base).

Example 207

5-[(2-Fluoro-6-chlorophenyl)acetylamino]-3-(3-methylphenyl)-4-(4-pyrimidinyl)isoxazole $^1$H-NMR(CDCl$_3$)δ: 11.58(s, 1H), 8.63(s, 1H), 8.37(d, J=5.6 Hz, 1H), 7.41-7.33(m, 4H), 7.30(s, 1H), 7.24(d, J=5.8 Hz, 1H), 7.16(dt, J=1.5 Hz, 8.9 Hz, 1H), 6.80(dd, J=1.5 Hz, 5.6 Hz, 1H), 4.14(d, J=1.5 Hz, 2H), 2.40(s, 3H).
Mass, m/e: 422(M$^+$), 236(base).

Example 208

5-[(2,6-Dichlorophenyl)acetylamino]-3-(3-methylphenyl)-4-(4-pyrimidinyl)isoxazole $^1$H-NMR(CDCl$_3$)δ: 11.50(s, 1H), 8.59(s, 1H), 8.36(d, J=5.4 Hz, 1H), 7.48(d, J=7.7 Hz, 2H), 7.40-7.32(m, 3H), 7.30(s, 1H), 7.25-7.23(m, 1H), 6.80(dd, J=1.9 Hz, 5.4 Hz, 1H), 4.32(s, 2H), 2.40(s, 3H).
Mass, m/e: 438(M$^+$), 236(base).

Example 209

5-[(2-Methoxyphenyl)acetylamino]-3-(3-methylphenyl)-4-(4-pyrimidinyl)isoxazole $^1$H-NMR(CDCl$_3$)δ: 11.36(s, 1H), 8.44(d, J=1.2 Hz, 1H), 8.31(d, J=5.6 Hz, 1H), 7.44(dt, J=1.5 Hz, 8.1 Hz, 1H), 7.38-

7.31(m, 3H), 7.28(s, 1H), 7.22(d, J=7.3 Hz, 1H), 7.08(t, J=7.3 Hz, 1H), 6.99(d, J=8.1 Hz, 1H), 6.74(dd, J=1.2 Hz, 5.6 Hz, 1H), 3.88(s, 2H), 3.80(s, 3H), 2.38(s, 3H).

Mass, m/e: 400($M^+$), 91(base).

Example 210

5-[(3-Methoxyphenyl)acetylamino]-3-(3-methylphenyl)-4-(4-pyrimidinyl)isoxazole $^1$H-NMR(CDCl$_3$)δ: 11.44(s, 1H), 8.58(s, 1H), 8.33(d, J=5.6 Hz, 1H), 7.41-7.32(m, 3H), 7.28(s, 1H), 7.22(d, J=7.3 Hz, 1H), 6.99-6.94(m, 3H), 6.76(dd, J=1.2 Hz, 5.6 Hz, 1H), 3.89(s, 2H), 3.83(s, 3H), 2.39(s, 3H).

Mass, m/e: 400($M^+$), 236(base).

Example 211

5-[(2,5-Dimethoxyphenyl)acetylamino]-3-(3-methylphenyl)-4-(4-pyrimidinyl)isoxazole $^1$H-NMR(CDCl$_3$)δ: 11.37(s, 1H), 8.56(d, J=1.4 Hz, 1H), 8.33(d, J=5.4 Hz, 1H), 7.38-7.31(m, 2H), 7.28(s, 1H), 7.22(d, J=7.3 Hz, 1H), 6.94-6.92(m, 1H), 6.76(dd, J=1.4 Hz, 5.4 Hz, 1H), 3.86(s, 2H), 3.81(s, 3H), 3.77(s, 3H), 2.39(s, 3H).

Mass, m/e: 430($M^+$), 178(base).

Example 212

5-[(2,3-Dimethoxyphenyl)acetylamino]-3-(3-methylphenyl)-4-(4-pyrimidinyl)isoxazole $^1$H-NMR(CDCl$_3$)δ: 11.49(s, 1H), 8.59(d, J=1.5 Hz, 1H), 8.32(d, J=5.4 Hz, 1H), 7.38-7.31(m, 2H), 7.28(s, 1H), 7.22(d, J=6.9 Hz, 1H), 7.14(t, J=8.1 Hz, 1H), 7.00(dd, J=1.2 Hz, 8.1 Hz, 1H), 6.95(dd, J=1.2 Hz, 7.3 Hz, 1H), 6.74(dd, J=1.5 Hz, 5.4 Hz, 1H), 3.90(s, 2H), 3.89(s, 3H), 3.88(s, 3H), 2.42(s, 3H).

Mass, m/e: 430($M^+$), 178(base).

Example 213

5-[(3,5-Dimethoxyphenyl)acetylamino]-3-(3-methylphenyl)-4-(4-pyrimidinyl)isoxazole $^1$H-NMR(CDCl$_3$)δ: 11.47(bs, 1H), 8.69(d, J=1.3 Hz, 1H), 8.34(d, J=5.6 Hz, 1H), 7.36(q, J=7.3 Hz, 1H), 7.33(d, J=7.3 Hz, 1H), 7.28(s, 1H), 7.22(d, J=7.3 Hz, 1H), 6.76(dd, J=1.3 Hz, 5.6 Hz, 1H), 6.54(d, J=2.3 Hz, 2H), 6.50(t, J=2.3 Hz, 1H), 3.84(s, 2H), 3.81(s, 6H), 2.39(s, 3H).

Mass, m/e: 430($M^+$), 178(base).

Example 214

3-(3-Methylphenyl)-5-[(2-methylphenyl)acetylamino]-4-(4-pyrimidinyl)isoxazole $^1$H-NMR(CDCl$_3$)δ: 11.38(s, 1H), 8.40(d, J=1.4 Hz, 1H), 8.31(d, J=5.6 Hz, 1H), 7.41-7.31(m, 6H), 7.27(bs, 1H), 7.21(dd, J=7.7 Hz, 1H), 6.74(dd, J=1.4 Hz, 5.6 Hz, 1H), 3.92(s, 2H), 2.38(s, 3H), 2.36(s, 3H).

Mass, m/e: 384($M^+$), 236(base).

Example 215

3-(3-Methylphenyl)-5-[(3-methylphenyl)acetylamino]-4-(4-pyrimidinyl)isoxazole $^1$H-NMR(CDCl$_3$)δ: 11.49(s, 1H), 8.47(s, 1H), 8.33(d, J=5.4 Hz, 1H), 7.39-7.32(m, 3H), 7.28-7.19(m, 5H), 6.76(dd, J=1.5 Hz, 5.4 Hz, 1H), 3.89(s, 2H), 2.39(s, 6H).

Mass, m/e: 384($M^+$), 236(base).

Example 216

5-[(2,5-Dimethylphenyl)acetylamino]-3-(3-methylphenyl)-4-(4-pyrimidinyl)isoxazole $^1$H-NMR(CDCl$_3$)δ: 11.34(s, 1H), 8.31(d, J=5.8 Hz, 1H), 8.37(d, J=1.4 Hz, 1H), 7.38-7.32(m, 2H), 7.28(s, 1H), 7.22-7.20(m, 3H), 7.15(s, 1H), 6.74(dd, J=1.4 Hz, 5.8 Hz, 1H), 3.87(s, 2H), 2.39(s, 6H), 2.31(s, 3H).

Mass, m/e: 398($M^+$), 236(base).

Example 217

3-(3-Methylphenyl)-4-(4-pyrimidinyl)-5-[(2-trifluoromethylphenyl)acetylamino]isoxazole $^1$H-NMR(CDCl$_3$)δ: 11.41(bs, 1H), 8.56(s, 1H), 8.35(d, J=5.6 Hz, 1H), 7.81(d, J=7.7 Hz, 1H), 7.66(t, J=7.7 Hz, 1H), 7.58(d, J=6.9 Hz, 1H), 7.54(d, J=7.7 Hz, 1H), 7.39-7.32(m, 2H), 7.29(s, 1H), 7.23(d, J=6.9 Hz, 1H), 6.78(dd, J=1.5 Hz, 5.6 Hz, 1H), 4.12(s, 2H), 2.35(s, 3H).

Mass, m/e: 438($M^+$), 236(base).

Example 218

3-(3-Methylphenyl)-5-(3-phenylpropionylamino)-4-(4-pyrimidinyl)isoxazole $^1$H-NMR(CDCl$_3$)δ: 11.46(bs, 1H), 9.06(d, J=1.4 Hz, 1H), 8.41(d, J=5.4 Hz, 1H), 7.41-7.25(m, 8H), 7.20-7.17(m, 1H), 6.83(dd, J=1.4 Hz, 5.4 Hz, 1H), 3.12(t, J=7.5 Hz, 2H), 2.98(t, J=7.5 Hz, 2H), 2.41(s, 3H).

Mass, m/e: 384($M^+$), 91(base).

Example 219

3-(3-Methylphenyl)-5-[(1-phenyl-cyclopropane)carbonylamino]-4-(4-pyrimidinyl)isoxazole $^1$H-NMR(CDCl$_3$)δ: 11.41(bs, 1H), 8.28(d, J=5.6 Hz, 1H), 8.19(d, J=1.5 Hz, 1H), 7.57-7.50(m, 5H), 7.37-7.30(m, 2H), 7.26(s, 1H), 7.20(d, J=7.3 Hz, 1H), 6.72(dd, J=1.5 Hz, 5.6 Hz, 1H), 2.38(s, 3H), 1.84(q, J=3.9 Hz, 2H), 1.30(q, J=3.9 Hz, 2H).

Mass, m/e: 396($M^+$), 117(base).

Example 220

3-(4-Methylphenyl)-5-(phenylacetylamino)-4-(4-pyrimidinyl)isoxazole a: 5-Amino-3-(4-methylphenyl)-4-(4-pyrimidinyl)isoxazole $^1$H-NMR(CDCl$_3$)δ: 9.01(d, J=1.4 Hz, 1H), 8.29(d, J=5.7 Hz, 1H), 7.50-7.20(m, 4H), 6.87(bs, 2H), 6.76(dd, J=1.4 Hz, 5.7 Hz, 1H), 2.45(s, 3H)

Mass, m/e: 252($M^+$), 107(base).

b: 3-(4-Methylphenyl)-5-(Phenylacetylamino)-4-(4-pyrimidinyl)isoxazole $^1$H-NMR(CDCl$_3$)δ: 11.41(s, 1H), 8.48(s, 1H), 8.33(d, J=5.6 Hz, 1H), 7.51-7.38(m, 5H), 7.36-7.27(m, 4H), 6.79(dd, J=1.4 Hz, 5.6 Hz, 1H), 3.94(s, 2H), 2.43(s, 3H).
Mass, m/e: 370(M$^+$), 236(base).

Example 221

3-(4-Ethylphenyl)-5-(phenylacetylamino)-4-(4-pyrimidinyl)isoxazole a: 5-Amino-3-(4-ethylphenyl)-4-(4-pyrimidinyl)isoxazole $^1$H-NMR(CDCl$_3$)δ: 9.01(d, J=1.2 Hz, 1H), 8.30(d, J=5.4 Hz, 1H), 7.43(d, J=8.1 Hz, 2H), 7.33(d, J=8.1 Hz, 2H), 6.85(bs, 2H), 6.77(dd, J=1.2 Hz, 5.4 Hz, 1H), 2.74(q, J=7.7 Hz, 2H), 1.30(t, J=7.7 Hz, 3H).
Mass, m/e: 266(M$^+$), 106(base).

b: 3-(4-Ethylphenyl)-5-(phenylacetylamino)-4-(4-pyrimidinyl)isoxazole $^1$H-NMR(CDCl$_3$)δ: 11.42(s, 1H), 8.48(s, 1H), 8.34(d, J=5.8 Hz, 1H), 7.49-7.30(m, 9H), 6.80(dd, J=1.5 Hz, 5.8 Hz, 1H), 3.94(s, 2H), 2.56(q, J=7.7 Hz, 2H), 1.27(t, J=7.7 Hz, 3H).
Mass, m/e: 384(M$^+$), 250(base).

Example 222

3-(4-Ethylphenyl)-5-[(2-fluorophenyl)acetylamino]-4-(4-pyrimidinyl)isoxazole $^1$H-NMR(CDCl$_3$)δ: 11.60(s, 1H), 8.61(s, 1H), 8.37(d, J=5.4 Hz, 1H), 7.46-7.17(m, 8H), 6.84(dd, J=1.5 Hz, 5.4 Hz, 1H), 4.00(s, 2H), 2.73(q, J=7.7 Hz, 2H), 1.29(t, J=7.7 Hz, 3H).
Mass, m/e: 402(M$^+$), 250(base).

Example 223

3-(4-Ethylphenyl)-5-[(2-chlorophenyl)acetylamino]-4-(4-pyrimidinyl)isoxazole $^1$H-NMR(CDCl$_3$)δ: 11.48(s, 1H), 8.53(s, 1H), 8.36(d, J=5.8 Hz, 1H), 7.54-7.31(m, 8H), 6.83(dd, J=1.5 Hz, 5.8 Hz, 1H), 4.07(s, 2H), 2.73(q, J=7.7 Hz, 2H), 1.28(t, J=7.7 Hz, 3H).
Mass, m/e: 418(M$^+$), 250(base).

Example 224

3-(2-Fluoro-5-methylphenyl)-5-(phenylacetylamino)-4-(4-pyrimidinyl)isoxazole a: 5-Amino-3-(2-fluoro-5-methylphenyl)-4-(4-pyrimidinyl)isoxazole $^1$H-NMR(CDCl$_3$)δ: 9.00(d, J=1.5 Hz, 1H), 8.32(d, J=5.4 Hz, 1H), 7.10(t, J=9.3 Hz, 1H), 7.34-7.30(m, 2H), 6.88(bs, 2H), 6.65(td, J=1.5 Hz, 5.4 Hz, 1H).
Mass, m/e: 270(M$^+$), 125(base).

b: 3-(2-Fluoro-5-methylphenyl)-5-(phenylacetylamino)-4-(4-pyrimidinyl)isoxazole $^1$H-NMR(CDCl$_3$)δ: 11.46(bs, 1H), 8.47(s, 1H), 8.37(d, J=5.4 Hz, 1H), 7.51-7.40(m, 5H), 7.34-7.28(m, 2H), 7.07(t, J=9.3 Hz, 1H), 6.70(td, J=1.9 Hz, 5.4 Hz, 1H), 3.94(s, 2H), 2.37(s, 3H).
Mass, m/e: 388(M$^+$), 254(base).

Example 225

3-(2-Fluoro-5-methylphenyl)-5-[(2-fluorophenyl)acetylamino]-4-(4-pyrimidinyl)isoxazole $^1$H-NMR(CDCl$_3$)δ: 11.64(s, 1H), 8.60(s, 1H), 8.39(d, J=5.8 Hz, 1H), 7.42(t, J=6.9 Hz, 2H), 7.33-7.26(m, 3H), 7.20(t, J=9.6 Hz, 1H), 7.08(t, J=8.9 Hz, 1H), 6.73(d, J=5.8 Hz, 1H), 3.97(s, 2H), 2.38(s, 3H).
Mass, m/e: 406(M$^+$), 254(base).

Example 226

3-(2-Fluoro-5-methylphenyl)-5-[(3-fluorophenyl)acetylamino]-4-(4-pyrimidinyl)isoxazole $^1$H-NMR(CDCl$_3$)δ: 11.50(bs, 1H), 8.64(s, 1H), 8.40(d, J=6.0 Hz, 1H), 7.47-7.42(m, 1H), 7.35-7.29(m, 2H), 7.20(d, J=7.7 Hz, 1H), 7.16-7.11(m, 2H), 7.08(t, J=9.3 Hz, 1H), 6.73(td, J=1.5 Hz, 6.0 Hz, 1H), 3.94(s, 2H), 2.38(s, 3H).
Mass, m/e: 406(M$^+$), 254(base).

Example 227

5-[(2-Chlorophenyl)acetylamino]-3-(2-fluoro-5-methylphenyl)-4-(4-pyrimidinyl)isoxazole $^1$H-NMR(CDCl$_3$)δ: 11.51(s, 1H), 8.52(s, 1H), 8.38(d, J=5.6 Hz, 1H), 7.54-7.51(m, 1H), 7.49-7.46(m, 1H), 7.42-7.39(m, 2H), 7.34-7.29(m, 2H), 7.07(t, J=9.3 Hz, 1H), 6.72(td, J=1.5 Hz, 5.6 Hz, 1H), 4.07(s, 2H), 2.37(s, 3H).
Mass, m/e: 422(M$^+$), 254(base).

Example 228

5-[(2-Bromophenyl)acetylamino]-3-(2-fluoro-5-methylphenyl)-4-(4-pyrimidinyl)isoxazole $^1$H-NMR(CDCl$_3$)δ: 11.49(bs, 1H), 8.51(s, 1H), 8.38(d, J=5.2 Hz, 1H), 7.72(dd, J=1.2 Hz, 7.7 Hz, 1H), 7.50-7.43(m, 2H), 7.35-7.29(m, 3H), 7.08(t, J=9.3 Hz, 1H), 6.72(td, J=1.9 Hz, 5.2 Hz, 1H), 4.09(s, 2H), 2.38(s, 3H).
Mass, m/e: 466(M$^+$), 254(base).

Example 229

3-(2-Fluoro-5-methylphenyl)-5-[(2-iodophenyl)acetylamino]-4-(4-pyrimidinyl)isoxazole $^1$H-NMR(CDCl$_3$)δ: 11.44(bs, 1H), 8.49(s, 1H), 8.38(d, J=5.4 Hz, 1H), 8.00(d, J=7.7 Hz, 1H), 7.48(d, J=4.2 Hz, 2H), 7.34-7.30(m, 2H), 7.18-7.13(m, 1H), 7.08(t, J=8.5 Hz, 1H), 6.72(td, J=1.9 Hz, 5.4 Hz, 1H), 4.10(s, 2H), 2.38(s, 3H)
Mass, m/e: 514(M$^+$), 254(base). .

Example 230

3-(2-Fluoro-5-methylphenyl)-5-[(2,4-difluorophenyl)acetylamino]-4-(4-pyrimidinyl)isoxazole $^1$H-NMR(CDCl$_3$)δ: 11.66(bs, 1H), 8.77(s, 1H), 8.43(d, J=5.6 Hz, 1H), 7.40(dt, J=6.2 Hz, 8.5 Hz, 1H), 7.36-7.30(m, 2H), 7.09(t, J=8.9 Hz, 1H), 7.01-6.92(m, 2H), 6.78(d, J=5.6 Hz, 1H), 3.94(s, 2H), 2.38(s, 3H).
Mass, m/e: 424(M$^+$), 254(base).

Example 231

5-[(2,5-Difluorophenyl)acetylamino]-3-(2-fluoro-5-methylphenyl)-4-(4-pyrimidinyl)isoxazole $^1$H-NMR(CDCl$_3$)δ: 11.69(bs, 1H), 8.78(s, 1H), 8.43(d, J=5.4 Hz, 1H), 7.36-7.29(m, 2H), 7.18-7.06(m, 4H), 6.77(td, J=1.9 Hz, 5.4 Hz, 1H), 3.95(s, 2H), 2.39(s, 3H).
Mass, m/e: 424(M$^+$), 254(base).

Example 232

5-[(2-Chloro-4-fluorophenyl)acetylamino]-3-(2-fluoro-5-methylphenyl)-4-(4-pyrimidinyl)isoxazole $^1$H-NMR(CDCl$_3$)δ: 11.54(bs, 1H), 8.70(s, 1H), 8.42(d, J=5.6 Hz, 1H), 7.45(dd, J=6.2 Hz, 8.9 Hz, 1H), 7.36-7.26(m, 3H), 7.14-7.06(m, 2H), 6.75(td, J=1.5 Hz, 5.6 Hz, 1H), 4.04(s, 2H), 2.38(s, 3H).
Mass, m/e: 440(M$^+$), 254(base).

Example 233

5-[(2-Chloro-6-fluorophenyl)acetylamino]-3-(2-fluoro-5-methylphenyl)-4-(4-pyrimidinyl)isoxazole $^1$H-NMR(CDCl$_3$)δ: 11.61(bs, 1H), 8.63(s, 1H), 8.41(d, J=5.4 Hz, 1H), 7.42-7.29(m, 4H), 7.16(dd, J=2.3 Hz, 6.9 Hz, 1H), 7.09(t, J=9.3 Hz, 1H), 6.75(td, J=1.9 Hz, 5.4 Hz, 1H), 4.14(d, J=1.9 Hz, 2H), 2.38(s, 3H).
Mass, m/e: 440(M$^+$), 254(base).

Example 234

5-[(2,6-Dichlorophenyl)acetylamino]-3-(2-fluoro-5-methylphenyl)-4-(4-pyrimidinyl)isoxazole $^1$H-NMR(CDCl$_3$)δ: 11.54(bs, 1H), 8.59(s, 1H), 8.40(d, J=5.4 Hz, 1H), 7.48(d, J=8.1 Hz, 2H), 7.37-7.30(m, 3H), 7.09(t, J=8.9 Hz, 1H), 6.74(td, J=1.9 Hz, 5.4 Hz, 1H), 4.31(s, 2H), 2.38(s, 3H).
Mass, m/e: 456(M$^+$), 254(base).

Example 235

3-(2-Fluoro-5-methylphenyl)-5-[(3-methoxyphenyl)acetylamino]-4-(4-pyrimidinyl)isoxazole $^1$H-NMR(CDCl$_3$)δ: 11.48(bs, 1H), 8.58(d, J=1.5 Hz, 1H), 8.37(d, J=5.2 Hz, 1H), 7.39(t, J=7.7 Hz, 1H), 7.34-7.28(m, 2H), 7.07(t, J=9.2 Hz, 1H), 7.00-6.94(m, 3H), 6.70(td, J=1.5 Hz, 5.2 Hz, 1H), 3.90(s, 2H), 3.83(s, 3H), 2.37(s, 3H)
Mass, m/e: 418(M$^+$), 148(base).

Example 236

5-[(2,3-Dimethoxyphenyl)acetylamino]-3-(2-fluoro-5-methylphenyl)-4-(4-pyrimidinyl)isoxazole $^1$H-NMR(CDCl$_3$)δ: 11.54(bs, 1H), 8.60(d, J=1.7 Hz, 1H), 8.36(d, J=5.6 Hz, 1H), 7.33-7.28(m, 2H), 7.14(t, J=8.1 Hz, 1H), 7.06(t, J=9.3 Hz, 1H), 7.00(dd, J=1.4 Hz, 8.1 Hz, 1H), 6.96(dd, J=1.4 Hz, 7.7 Hz, 1H), 6.69(td, J=1.7 Hz, 5.6 Hz, 1H), 3.91(s, 2H), 3.89(s, 3H), 3.88(s, 3H), 2.37(s, 3H).
Mass, m/e: 448(M$^+$), 178(base).

Example 237

5-[(2,5-Dimethoxyphenyl)acetylamino]-3-(2-fluoro-5-methylphenyl)-4-(4-pyrimidinyl)isoxazole $^1$H-NMR(CDCl$_3$)δ: 11.41(bs, 1H), 8.56 (J=1.5 Hz, 1H), 8.36(d, J=5.4 Hz, 1H), 7.33-7.29(m, 2H), 7.07(t, J=8.9 Hz, 1H), 6.96-6.90(m, 3H), 6.70(td, J=1.5 Hz, 5.4 Hz, 1H), 3.86(s, 2H), 3.81(s, 3H), 3.77(s, 3H), 2.37(s, 3H).
Mass, m/e: 448(M$^+$), 178(base).

Example 238

3-(2-Fluoro-5-methylphenyl)-5-[(2-methylphenyl)acetylamino]-4-(4-pyrimidinyl)isoxazole $^1$H-NMR(CDCl$_3$)δ: 11.42(bs, 1H), 8.40(d, J=1.3 Hz, 1H), 8.35(d, J=5.4 Hz, 1H), 7.41-7.28(m, 6H), 7.07(t, J=8.9 Hz, 1H), 6.68(td, J=1.3 Hz, 5.4 Hz, 1H), 3.92(s, 2H), 2.37(s, 3H), 2.36(s, 3H).
Mass, m/e: 402(M$^+$), 254(base).

Example 239

5-[(2,5-Dimethylphenyl)acetylamino]-3-(2-fluoro-5-methylphenyl)-4-(4-pyrimidinyl)isoxazole $^1$H-NMR(CDCl$_3$)δ: 11.39(bs, 1H), 8.37-8.35(m, 2H), 7.34-7.28(m, 2H), 7.20(t, J=8.1 Hz, 2H), 7.15(s, 1H), 7.07(t, J=9.2 Hz, 1H), 6.69(td, J=1.9 Hz, 5.8 Hz, 1H), 3.88(s, 2H), 2.38(s, 3H), 2.37(s, 3H), 2.31(s, 3H).
Mass, m/e: 416(M$^+$), 254(base).

Example 240

3-(2-Fluoro-5-methylphenyl)-4-(4-pyrimidinyl)-5-[(2-trifluoromethylphenyl)acetylamino]isoxazole $^1$H-NMR(CDCl$_3$)δ: 11.45(bs, 1H), 8.55(s, 1H), 8.39(d, J=5.6 Hz, 1H), 7.81(d, J=8.1 Hz, 1H), 7.67(t, J=7.7 Hz, 1H), 7.58(d, J=6.9 Hz, 1H), 7.55(d, J=7.7 Hz, 1H), 7.35-7.29(m, 2H), 7.08(t, J=9.3 Hz, 1H), 6.73(td, J=1.9 Hz, 5.6 Hz, 1H), 4.12(s, 2H), 2.38(s, 3H).
Mass, m/e: 456(M$^+$), 254(base).

Example 241

3-(3-Methyl-4-fluorophenyl)-5-(phenylacetylamino)-4-(4-pyrimidinyl)isoxazole a: 5-Amino-3-(3-methyl-4-fluorophenyl)-4-(4-pyrimidinyl)isoxazole $^1$H-NMR(CDCl$_3$)δ: 9.02(d, J=1.5 Hz, 1H), 8.32(d, J=5.4 Hz, 1H), 7.37(dd, J=7.3 Hz, 1.6 Hz, 1H), 7.32-7.28(m, 1H), 7.13(t, J=8.5 Hz, 1H), 6.89(bs, 2H), 6.73(dd, J=1.2 Hz, 5.4 Hz, 1H), 2.33(d, J=1.5 Hz, 3H).
Mass, m/e: 270($M^+$), 125(base).

b: 3-(3-Methyl-4-fluorophenyl)-5-(phenylacetylamino)-4-(4-pyrimidinyl)isoxazole $^1$H-NMR(CDCl$_3$)δ: 11.39(bs, 1H), 8.48(s, 1H), 8.35(d, J=5.8 Hz, 1H), 7.51-7.39(m, 4H), 7.34-7.30(m, 1H), 7.26-7.21(m, 2H), 7.11(t, J=8.5 Hz, 1H), 6.76(dd, J=1.5 Hz, 5.8 Hz, 1H), 3.93(s, 2H), 2.31(d, J=1.9 Hz, 3H).
Mass, m/e: 388($M^+$), 91(base).

Example 242

5-[(2-Fluorophenyl)acetylamino]-3-(3-methyl-4-fluorophenyl)-4-(4-pyrimidinyl)isoxazole $^1$H-NMR(CDCl$_3$)δ: 11.57(bs, 1H), 8.61(s, 1H), 8.38(d, J=5.8 Hz, 1H), 7.46-7.40(m, 3H), 7.32(dd, J=1.9 Hz, 7.3 Hz, 1H), 7.28-7.17(m, 2H), 7.12(t, J=8.5 Hz, 1H), 6.78(dd, J=1.5 Hz, 5.8 Hz, 1H), 3.96(s, 2H), 2.31(d, J=1.9 Hz, 3H).
Mass, m/e: 406($M^+$), 254(base).

Example 243

5-[(3-Fluorophenyl)acetylamino]-3-(3-methyl-4-fluorophenyl)-4-(4-pyrimidinyl)isoxazole $^1$H-NMR(CDCl$_3$)δ: 11.43(bs, 1H), 8.65(s, 1H), 8.39(d, J=5.6 Hz, 1H), 7.47-7.40(m, 2H), 7.32(dd, J=1.9 Hz, 7.3 Hz, 1H), 7.28-7.17(m, 3H), 7.12(t, J=8.5 Hz, 1H), 6.78(dd, J=1.5 Hz, 5.6 Hz, 1H), 3.96(s, 2H), 2.31(d, J=1.9 Hz, 3H).
Mass, m/e: 406($M^+$), 254(base).

Example 244

5-[(2-Chlorophenyl)acetylamino]-3-(3-methyl-4-fluorophenyl)-4-(4-pyrimidinyl)isoxazole $^1$H-NMR(CDCl$_3$)δ: 11.45(bs, 1H), 8.53(s, 1H), 8.37(d, J=5.6 Hz, 1H), 7.54-7.51(m, 1H), 7.48-7.45(m, 1H), 7.42-7.39(m, 2H), 7.32(d, J=7.3 Hz, 1H), 7.26-7.22(m, 1H), 7.12(t, J=8.9 Hz, 1H), 6.77(dd, J=1.6 Hz, 5.6 Hz, 1H), 4.06(s, 2H), 2.31(d, J=1.5 Hz, 3H).
Mass, m/e: 422($M^+$), 254(base).

Example 245

5-[(2-Bromophenyl)acetylamino]-3-(3-methyl-4-fluorophenyl)-4-(4-pyrimidinyl)isoxazole $^1$H-NMR(CDCl$_3$)δ: 11.43(bs, 1H), 8.51(s, 1H), 8.37(d, J=5.8 Hz, 1H), 7.71(d, J=8.1 Hz, 1H), 7.49-7.43(m, 2H), 7.35-7.31(m, 2H), 7.26-7.22(m, 1H), 7.12(t, J=8.9 Hz, 1H), 6.77(dd, J=1.6 Hz, 5.8 Hz, 1H), 4.08(s, 2H), 2.31(d, J=1.9 Hz, 3H).
Mass, m/e: 468($M^+$), 254(base).

Example 246

5-[(2-Iodophenyl)acetylamino]-3-(3-methyl-4-fluorophenyl)-4-(4-pyrimidinyl)isoxazole $^1$H-NMR(CDCl$_3$)δ: 11.38(bs, 1H), 8.50(s, 1H), 8.37(d, J=5.4 Hz, 1H), 8.00(d, J=7.7 Hz, 1H), 7.49-7.46(m, 2H), 7.32(d, J=6.9 Hz, 1H), 7.26-7.22(m, 1H), 7.18-7.10(m, 2H), 6.76(dd, J=1.2 Hz, 5.4 Hz, 1H), 4.09(s, 2H), 2.31(d, J=1.9 Hz, 3H).
Mass, m/e: 514($M^+$), 254(base).

Example 247

5-[(2,4-Difluorophenyl)acetylamino]-3-(3-methyl-4-fluorophenyl)-4-(4-pyrimidinyl)isoxazole $^1$H-NMR(CDCl$_3$)δ: 11.59(s, 1H), 8.79(s, 1H), 8.42(d, J=5.4 Hz, 1H), 7.39(t, J=6.6 Hz, 8.5 Hz, 1H), 7.33(dd, J=1.9 Hz, 7.3 Hz, 1H), 7.29-7.24(m, 1H), 7.13(t, J=8.9 Hz, 1H), 7.00-6.91(m, 2H), 6.82(dd, J=1.2 Hz, 5.4 Hz, 1H), 3.97(s, 2H), 2.32(d, J=1.9 Hz, 3H).
Mass, m/e: 424($M^+$), 254(base).

Example 248

5-[(2,5-Difluorophenyl)acetylamino]-3-(3-methyl-4-fluorophenyl)-4-(4-pyrimidinyl)isoxazole $^1$H-NMR(CDCl$_3$)δ: 11.62(bs, 1H), 8.79(s, 1H), 8.42(d, J=5.4 Hz, 1H), 7.33(dd, J=1.5 Hz, 7.3 Hz, 1H), 7.28-7.24(m, 1H), 7.17-7.06(m, 4H), 6.82(dd, J=1.6 Hz, 5.4 Hz, 1H), 3.94(s, 2H), 2.32(d, J=1.5 Hz, 3H).
Mass, m/e: 424($M^+$), 254(base).

Example 249

5-[(2-Chloro-4-fluorophenyl)acetylamino]-3-(3-methyl-4-fluorophenyl)-4-(4-pyrimidinyl)isoxazole $^1$H-NMR(CDCl$_3$) δ: 11.48(bs, 1H), 8.71(s, 1H), 8.41(d, J=5.6 Hz, 1H), 7.45(dd, J=6.2 Hz, 8.9 Hz, 1H), 7.33(dd, J=1.9 Hz, 7.3 Hz, 1H), 7.28-7.23(m, 2H), 7.15-7.09(m, 2H), 6.81 (dd, J=1.5 Hz, 5.6 Hz, 1H), 4.03(s, 2H), 2.32(d, J=1.9 Hz, 3H).
Mass, m/e: 440($M^+$), 254(base).

Example 250

5-[(2-Chloro-6-fluorophenyl)acetylamino]-3-(3-methyl-4-fluorophenyl)-4-(4-pyrimidinyl)isoxazole $^1$H-NMR(CDCl$_3$) δ: 11.55(bs, 1H), 8.63(s, 1H), 8.40(d, J=5.4 Hz, 1H), 7.42-7.32(m, 3H), 7.27-7.23(m, 1H), 7.18-7.11(m, 2H), 6.80(dd, J=1.2 Hz, 5.4 Hz, 1H), 4.14(s, 2H), 2.32(d, J=1.9 Hz, 3H).
Mass, m/e: 440($M^+$), 254(base).

Example 251

5-[(2,6-Dichlorophenyl)acetylamino]-3-(3-methyl-4-fluorophenyl)-4-(4-pyrimidinyl)isoxazole $^1$H-NMR(CDCl$_3$) δ: 11.47(bs, 1H), 8.60(s, 1H), 8.39(d, J=5.6 Hz, 1H), 7.48(d, J=8.1 Hz, 2H), 7.37-7.32(m, 2H), 7.27-7.23(m, 1H), 7.13(t, J=9.3 Hz, 1H), 6.80(dd, J=1.5 Hz, 5.6 Hz, 1H), 4.31(s, 2H), 2.32(d, J=1.9 Hz, 3H).
Mass, m/e: 456($M^+$), 254(base).

Example 252

5-[(2-Methoxyphenyl)acetylamino]-3-(3-methyl-4-fluorophenyl)-4-(4-pyrimidinyl)isoxazole $^1$H-NMR(CDCl$_3$) δ: 11.34(bs, 1H), 8.45(d, J=1.4 Hz, 1H), 8.34(d, J=5.6 Hz, 1H), 7.45(dt, J=1.9 Hz, 8.1 Hz, 1H), 7.35-

7.30(m, 2H), 7.24-7.20(m, 1H), 7.13-7.06(m, 2H), 6.99(d, J=8.1 Hz, 1H), 6.73(dd, J=1.4 Hz, 5.6 Hz, 1H), 3.88(s, 2H), 3.80(s, 3H), 2.31(d, J=1.9 Hz, 3H).

Mass, m/e: 418(M⁺), 148(base).

Example 253

5-[(3-Methoxyphenyl)acetylamino]-3-(3-methyl-4-fluorophenyl)-4-(4-pyrimidinyl)isoxazole ¹H-NMR(CDCl₃) δ: 11.41(s, 1H), 8.59(s, 1H), 8.36(d, J=5.8 Hz, 1H), 7.39(t, J=8.1 Hz, 1H), 7.31(d, J=7.0 Hz, 1H), 7.25-7.22(m, 1H), 7.11(t, J=9.3 Hz, 1H), 6.98-6.94(m, 3H), 6.76(dd, J=1.2 Hz, 5.8 Hz, 1H), 3.89(s, 2H), 3.83(s, 3H), 2.31(s, 3H).

Mass, m/e: 418(M⁺), 254(base).

Example 254

5-[(2,3-Dimethoxyphenyl)acetylamino]-3-(3-methyl-4-fluorophenyl)-4-(4-pyrimidinyl)isoxazole ¹H-NMR(CDCl₃) δ: 11.47(bs, 1H), 8.60(d, J=1.4 Hz, 1H), 8.39(d, J=5.6 Hz, 1H), 7.31(dd, J=1.9 Hz, 6.9 Hz, 1H), 7.24-7.21(m, 1H), 7.16-7.09(m, 2H), 7.00(dd, J=1.5 Hz, 8.1 Hz, 1H), 6.95(dd, J=1.5 Hz, 7.7 Hz, 1H), 6.74(dd, J=1.4 Hz, 5.6 Hz, 1H), 3.90(s, 2H), 3.89(s, 3H), 3.88(s, 3H), 2.31(s, 3H).

Mass, m/e: 448(M⁺), 178(base).

Example 255

5-[(2,5-Dimethoxyphenyl)acetylamino]-3-(3-methyl-4-fluorophenyl)-4-(4-pyrimidinyl)isoxazole ¹H-NMR(CDCl₃) δ: 11.35(bs, 1H), 8.57(d, J=1.4 Hz, 1H), 8.35(d, J=5.4 Hz, 1H), 7.32(dd, J=1.5 Hz, 6.9 Hz, 1H), 7.25-7.21(m, 1H), 7.11(t, J=8.5 Hz, 1H), 6.96-6.91(m, 3H), 6.75(dd, J=1.4 Hz, 5.4 Hz, 1H), 3.85(s, 2H), 3.81(s, 3H), 3.76(s, 3H), 2.31(d, J=1.9 Hz, 3H).

Mass, m/e: 448(M⁺), 178(base).

Example 256

5-[(3,5-Dimethoxyphenyl)acetylamino]-3-(3-methyl-4-fluorophenyl)-4-(4-pyrimidinyl)isoxazole ¹H-NMR(CDCl₃) δ: 11.45(bs, 1H), 8.69(d, J=1.5 Hz, 1H), 8.37(d, J=5.8 Hz, 1H), 7.31(dd, J=1.9 Hz, 7.3 Hz, 1H), 7.25-7.21(m, 1H), 7.12(t, J=8.9 Hz, 1H), 6.76(dd, J=1.5 Hz, 5.8 Hz, 1H), 6.53(d, J=2.3 Hz, 2H), 6.50(t, J=2.3 Hz, 1H), 3.84(s, 2H), 3.81(s, 6H), 2.31(d, J=1.9 Hz, 3H).

Mass, m/e: 448(M⁺), 178(base).

Example 257

3-(3-Methyl-4-fluorophenyl)-5-[(2-methylphenyl)acetylamino]-4-(4-pyrimidinyl)isoxazole ¹H-NMR(CDCl₃) δ: 11.35(bs, 1H), 8.41(d, J=1.4 Hz, 1H), 8.34(d, J=5.4 Hz, 1H), 7.41-7.30(m, 5H), 7.24-7.20(m, 1H), 7.11(t, J=9.3 Hz, 1H), 6.74(dd, J=1.4 Hz, 5.4 Hz, 1H), 3.92(s, 2H), 2.35(s, 3H), 2.30(d, J=1.9 Hz, 3H).

Mass, m/e: 402(M⁺), 254(base).

Example 258

3-(3-Methyl-4-fluorophenyl)-5-[(3-methylphenyl)acetylamino]-4-(4-pyrimidinyl)isoxazole ¹H-NMR(CDCl₃) δ: 11.37(bs, 1H), 8.48(s, 1H), 8.35(d, J=5.6 Hz, 1H), 7.37(t, J=7.3 Hz, 1H), 7.31(d, J=7.3 Hz, 1H), 7.27-7.18(m, 4H), 7.11(t, J=8.9 Hz, 1H), 6.76(dd, J=1.2 Hz, 5.6 Hz, 1H), 3.88(s, 2H), 2.39(s, 3H), 2.31(s, 3H).

Mass, m/e: 402(M⁺), 254(base).

Example 259

5-[(2,5-Dimethylphenyl)acetylamino]-3-(3-methyl-4-fluorophenyl)-4-(4-pyrimidinyl)isoxazole ¹H-NMR(CDCl₃) δ: 11.32(bs, 1H), 8.38(d, J=1.2 Hz, 1H), 8.35(d, J=5.6 Hz, 1H), 7.31(dd, J=1.5 Hz, 7.3 Hz, 1H), 7.24-7.20(m, 3H), 7.15(s, 1H), 7.11(t, J=8.9 Hz, 1H), 6.74(dd, J=1.2 Hz, 5.6 Hz, 1H), 3.87(s, 2H), 2.38(s, 3H), 2.31(s, 3H), 2.31(s, 3H).

Mass, m/e: 416(M⁺), 254(base).

Example 260

3-(3-Methyl-4-fluorophenyl)-5-[(2-nitrophenyl)acetylamino]-4-(4-pyrimidinyl)isoxazole ¹H-NMR(CDCl₃) δ: 11.67(bs, 1H), 8.88(s, 1H), 8.43(d, J=5.8 Hz, 1H), 8.20(d, J=8.5 Hz, 1H), 7.72(t, J=7.7 Hz, 1H), 7.58(t, J=7.7 Hz, 2H), 7.35(d, J=7.3 Hz, 1H), 7.29-7.25(m, 1H), 7.14(t, J=8.9 Hz, 1H), 6.83(dd, J=1.5 Hz, 5.8 Hz, 1H), 4.31(s, 2H), 2.33(d, J=1.5 Hz, 3H).

Mass, m/e: 433(M⁺), 254(base).

Example 261

3-(3-Methyl-4-fluorophenyl)-4-(4-pyrimidinyl)-5-[(2-trifluoromethylphenyl)acetylamino]isoxazole ¹H-NMR(CDCl₃) δ: 11.38(bs, 1H), 8.57(s, 1H), 8.38(d, J=5.4 Hz, 1H), 7.81(d, J=8.1 Hz, 1H), 7.66(t, J=6.9 Hz, 1H), 7.58-7.54(m, 2H), 7.32(dd, J=1.5 Hz, 6.9 Hz, 1H), 7.26-7.22(m, 1H), 7.12(t, J=8.9 Hz, 1H), 6.78(dd, J=1.5 Hz, 5.4 Hz, 1H), 4.12(s, 2H), 2.31(d, J=1.9 Hz, 3H).

Mass, m/e: 456(M⁺), 254(base).

Example 262

3-(3-Fluoro-4-methylphenyl)-5-(phenylacetylamino)-4-(4-pyrimidinyl)isoxazole a: 5-Amino-3-(3-fluoro-4-methylphenyl)-4-(4-pyrimidinyl)isoxazole ¹H-NMR(CDCl₃) δ: 9.01(d, J=1.4 Hz, 1H), 8.32(d, J=5.8 Hz, 1H), 7.32(t, J=8.1 Hz, 1H), 7.20-7.17(m, 2H), 6.87(bs, 2H), 6.75(dd, J=1.4 Hz, 5.8 Hz, 1H), 2.46(s, 3H).

Mass, m/e: 270(M⁺), 125(base).

b: 3-(3-Fluoro-4-methylphenyl)-5-(phenylacetylamino)-4-(4-pyrimidinyl)isoxazole

¹H-NMR(CDCl₃) δ: 11.39(bs, 1H), 8.49(s, 1H), 8.37(d, J=5.4 Hz, 1H), 7.51-7.39(m, 5H), 7.30(t, J=7.1 Hz, 1H), 7.13(d, J=9.3 Hz, 2H), 6.78(dd, J=1.5 Hz, 5.4 Hz, 1H), 3.93(s, 2H), 2.35(d, J=1.5 Hz, 3H).

Mass, m/e: 388(M⁺), 254(base).

Example 263

3-(3-Fluoro-4-methylphenyl)-5-[(2-fluorophenyl)acetylamino]-4-(4-pyrimidinyl)isoxazole $^1$H-NMR(CDCl$_3$) δ: 11.57(s, 1H), 8.61(s, 1H), 8.40(d, J=5.4 Hz, 1H), 7.46-7.40(m, 2H), 7.39-7.13(m, 5H), 6.82(dd, J=1.5 Hz, 5.4 Hz, 1H), 3.96(d, J=0.8 Hz, 2H), 2.36(d, J=1.6 Hz, 3H).
Mass, m/e: 406(M$^+$), 109(base).

Example 264

5-[(2-Chlorophenyl)acetylamino]-3-(3-fluoro-4-methylphenyl)-4-(4-pyrimidinyl)isoxazole $^1$H-NMR(CDCl$_3$) δ: 11.45(s, 1H), 8.53(s, 1H), 8.38(d, J=5.4 Hz, 1H), 7.54-7.51(m, 1H), 7.48(m, 1H), 7.42-7.39(m, 1H), 7.33(t, J=7.7 Hz, 2H), 7.15-7.13(m, 2H), 6.81(dd, J=1.2 Hz, 5.4 Hz, 1H), 4.06(s, 2H), 2.35(d, J=1.9 Hz, 3H).
Mass, m/e: 422(M$^+$), 254(base).

Example 265

3-(4-Chloro-3-methylphenyl)-5-(phenylacetylamino)-4-(4-pyrimidinyl)isoxazole a: 5-Amino-3-(4-chloro-3-methylphenyl)-4-(4-pyrimidinyl)isoxazole $^1$H-NMR(CDCl$_3$) δ: 9.02(d, J=1.5 Hz, 1H), 8.33(d, J=5.8 Hz, 1H), 7.48(d, J=8.1H, 1H), 7.41(d, J=1.9 Hz, 1H), 7.28(dd, J=1.5 Hz, 8.1 Hz, 1H), 6.86(bs, 2H), 6.74(dd, J=1.5 Hz, 5.8 Hz, 1H), 2.43(s, 3H).
Mass, m/e: 286(M$^+$), 141(base).

b: 3-(4-Chloro-3-methylphenyl)-5-(phenylacetylamino)-4-(4-pyrimidinyl)isoxazole $^1$H-NMR(CDCl$_3$) δ: 11.40(s, 1H), 8.49(s, 1H), 8.37(d, J=5.7 Hz, 1H), 7.51-7.36(m, 7H), 7.20(dd, J=1.5 Hz, 8.1 Hz, 1H), 6.76(dd, J=1.5 Hz, 5.7 Hz, 1H), 3.97(s, 2H), 2.39(s, 3H).
Mass, m/e: 404(M$^+$), 91(base).

Example 266

3-(4-Chloro-3-methylphenyl)-5-[(2-fluorophenyl)acetylamino]-4-(4-pyrimidinyl)isoxazole $^1$H-NMR(CDCl$_3$) δ: 11.58(s, 1H), 8.61(s, 1H), 8.40(d, J=5.8 Hz, 1H), 7.48-7.37(m, 5H), 7.28-7.18(m, 2H), 6.80(dd, J=1.5 Hz, 5.8 Hz, 1H), 3.96(s, 2H), 2.42(s, 3H).
Mass, m/e: 422(M$^+$), 109(base).

Example 267

5-[(2-Chlorophenyl)acetylamino]-3-(4-chloro-3-methylphenyl)-4-(4-pyrimidinyl)isoxazole $^1$H-NMR(CDCl$_3$) δ: 11.45(s, 1H), 8.53(s, 1H), 8.39(d, J=5.4 Hz, 1H), 7.54-7.36(m, 6H), 7.21(dd, J=1.9 Hz, 8.1 Hz, 1H), 6.79(dd, J=1.5 Hz, 5.4 Hz, 1H), 4.07(s, 2H), 2.42(s, 3H).
Mass, m/e: 438(M$^+$), 270(base).

Example 268

3-(4-Methoxy-3-methylphenyl)-5-(phenylacetylamino)-4-(4-pyrimidinyl)isoxazole a: 5-Amino-3-(4-methoxy-3-methylphenyl)-4-(4-pyrimidinyl)isoxazole $^1$H-NMR(CDCl$_3$) δ: 9.00(bs, 1H), 8.31(d, J=5.4 Hz, 1H), 7.32-7.29(m, 2H), 6.92(d, J=8.1 Hz, 1H), 6.83-6.81(m, 3H), 3.90(s, 3H), 2.26(s, 3H).
Mass, m/e: 282(M$^+$), 137(base).

b: 3-(4-Methoxy-3-methylphenyl)-5-(phenylacetylamino)-4-(4-pyrimidinyl)isoxazole $^1$H-NMR(CDCl$_3$) δ: 11.40(s, 1H), 8.48(s, 1H), 8.34(d, J=5.4 Hz, 1H), 7.51-7.39(m, 5H), 7.23-7.22(m, 1H), 6.90(d, J=8.1 Hz, 1H), 6.85(dd, J=1.5 Hz, 5.4 Hz, 1H), 6.67(dt, J=1.5 Hz, 5.4 Hz, 1H), 3.93(s, 2H), 3.89(s, 3H), 2.23(s, 3H).
Mass, m/e: 400(M$^+$), 91(base).

Example 269

5-[(2-Fluorophenyl)acetylamino]-3-(4-methoxy-3-methylphenyl)-4-(4-pyrimidinyl)isoxazole $^1$H-NMR(CDCl$_3$) δ: 11.58(s, 1H), 8.60(s, 1H), 8.37(d, J=5.4 Hz, 1H), 7.45-7.40(m, 2H), 7.27-7.17(m, 3H), 6.91(d, J=8.1 Hz, 1H), 6.80(dd, J=1.5 Hz, 5.8 Hz, 1H), 6.67(dt, J=1.5 Hz, 5.4 Hz, 1H), 4.00(s, 2H), 3.89(s, 3H), 2.24(s, 3H).
Mass, m/e: 418(M$^+$), 109(base).

Example 270

5-[(2-Chlorophenyl)acetylamino]-3-(4-methoxy-3-methylphenyl)-4-(4-pyrimidinyl)isoxazole $^1$H-NMR(CDCl$_3$) δ: 11.46(s, 1H), 8.53(s, 1H), 8.36(d, J=5.8 Hz, 1H), 7.54-7.39(m, 4H), 7.26-7.24(m, 1H), 6.91(d, J=8.5 Hz, 1H), 6.87(dd, J=1.5 Hz, 5.8 Hz, 1H), 6.67(dt, J=1.5 Hz, 5.4 Hz, 1H), 4.06(s, 2H), 3.89(s, 3H), 2.24(s, 3H).
Mass, m/e: 434(M$^+$), 121(base).

Example 271

3-(2,3-Dimethylphenyl)-5-(phenylacetylamino)-4-(4-pyrimidinyl)isoxazole a: 5-Amino-3-(2,3-dimethylphenyl)-4-(4-pyrimidinyl)isoxazole $^1$H-NMR(CDCl$_3$) δ: 8.97(d, J=1.5 Hz, 1H), 8.22(d, J=5.6 Hz, 1H), 7.31(d, J=7.3 Hz, 1H), 7.22(d, J=7.3 Hz, 1H), 7.15(d, J=9.3 Hz, 1H), 6.93(bs, 2H), 6.33(dd, J=1.5 Hz, 5.6 Hz, 1H), 2.35(s, 3H), 2.11(s, 3H).
Mass, m/e: 266(M$^+$), 77(base).

b: 3-(2,3-Dimethylphenyl)-5-(phenylacetylamino)-4-(4-pyrimidinyl)isoxazole $^1$H-NMR(CDCl$_3$) δ: 11.49(bs, 1H), 8.45(s, 1H), 8.27(d, J=5.4 Hz, 1H), 7.49-7.41(m, 5H), 7.31(d, J=7.3 Hz, 1H), 7.20(t, J=7.3 Hz, 1H), 7.10(d, J=6.9 Hz, 1H), 6.39(dd, J=1.5 Hz, 5.4 Hz, 1H), 3.95(s, 2H), 2.32(s, 3H), 2.02(s, 3H)
Mass, m/e: 384(M$^+$), 94(base).

Example 272

3-(2,3-Dimethylphenyl)-5-[(2-fluorophenyl)acetylamino]-4-(4-pyrimidinyl)isoxazole $^1$H-NMR(CDCl$_3$) δ: 11.67(bs, 1H), 8.57(s, 1H), 8.29(d, J=5.4 Hz, 1H), 7.46(m, 2H), 7.32(d, J=7.7 Hz, 1H), 7.28-7.18 (m, 3H), 7.11(d, J=6.9 Hz, 1H), 6.42(dd, J=1.2 Hz, 5.4 Hz, 1H), 3.98(s, 2H), 2.33(s, 6H), 2.04(s, 3H).
Mass, m/e: 402(M$^+$), 250(base).

Example 273

3-(2,5-Dimethylphenyl)-5-(phenylacetylamino)-4-(4-pyrimidinyl)isoxazole a: 5-Amino-3-(2,5-dimethylphenyl)-4-(4-pyrimidinyl)isoxazole $^1$H-NMR(CDCl$_3$) δ: 8.97(d, J=1.3 Hz, 1H), 8.24(d, J=5.4 Hz, 1H), 7.26-7.20(m, 2H), 7.15(s, 1H), 6.91(bs, 2H), 6.38 (dd, J=1.3 Hz, 5.4 Hz, 1H), 2.35(s, 3H), 2.15(s, 3H).
Mass, m/e: 266(M$^+$), 77(base).

b: 3-(2,5-Dimethylphenyl)-5-(phenylacetylamino)-4-(4-pyrimidinyl)isoxazole $^1$H-NMR(CDCl$_3$) δ: 11.49(bs, 1H), 8.45(s, 1H), 8.28(d, J=5.8 Hz, 1H), 7.51-7.41(m, 5H), 7.24-7.18(m, 2H), 7.08(bs, 1H), 6.42(dd, J=1.5 Hz, 5.8 Hz, 1H), 3.95(s, 2H), 2.33(s, 3H), 2.06(s, 3H).
Mass, m/e: 384(M$^+$), 91(base).

Example 274

3-(2,5-Dimethylphenyl)-5-[(2-fluorophenyl)acetylamino]-4-(4-pyrimidinyl)isoxazole $^1$H-NMR(CDCl$_3$) δ: 11.66(bs, 1H), 8.57(s, 1H), 8.31(d, J=5.4 Hz, 1H), 7.45-7.41(m, 2H), 7.28-7.17(m, 4H), 7.09(bs, 1H), 6.45(dd, J=1.5 Hz, 5.4 Hz, 1H), 3.98(s, 2H), 2.33(s, 3H), 2.07(s, 3H).
Mass, m/e: 402(M$^+$), 109(base).

Example 275

5-[(2-Chlorophenyl)acetylamino]-3-(2,5-dimethylphenyl)-4-(4-pyrimidinyl)isoxazole $^1$H-NMR(CDCl$_3$) δ: 11.54(bs, 1H), 8.50(s, 1H), 8.30(d, J=5.4 Hz, 1H), 7.54-7.52(m, 1H), 7.50-7.46(m, 1H), 7.44-7.38(m, 2H), 7.22-7.19(m, 2H), 7.09(bs, 1H), 6.45(dd, J=1.6 Hz, 5.4 Hz, 1H), 4.08(s, 2H), 2.33(s, 3H), 2.07(s, 3H).
Mass, m/e: 418(M$^+$), 250(base).

Example 276

3-(2,6-Dimethylphenyl)-5-(phenylacetylamino)-4-(4-pyrimidinyl)isoxazole a: 5-Amino-3-(2,6-dimethylphenyl)-4-(4-pyrimidinyl)isoxazole $^1$H-NMR(CDCl$_3$) δ: 8.97(d, J=1.2 Hz, 1H), 8.21(d, J=5.6 Hz, 1H), 7.31(t, J=7.5 Hz, 1H), 7.16(d, J=7.5 Hz, 2H), 6.96 (bs, 2H), 6.21(dd, J=1.2 Hz, 5.6 Hz, 1H), 2.15(s, 6H).
Mass, m/e: 266(M$^+$), 77(base).

b: 3-(2,6-Dimethylphenyl)-5-(phenylacetylamino)-4-(4-pyrimidinyl)isoxazole $^1$H-NMR(CDCl$_3$) δ: 11.54(bs, 1H), 8.45(s, 1H), 8.26(d, J=5.4 Hz, 1H), 7.52-7.43(m, 5H), 7.31(t, J=7.5 Hz, 1H), 7.14(d, J=7.5 Hz, 2H), 6.26(dd, J=1.6 Hz, 5.4 Hz, 1H), 3.96(s, 2H), 2.06(s, 6H).
Mass, m/e: 384(M$^+$), 91(base).

Example 277

3-(2,6-Dimethylphenyl)-5-[(2-fluorophenyl)acetylamino]-4-(4-pyrimidinyl)isoxazole $^1$H-NMR(CDCl$_3$) δ: 11.71(s, 1H), 8.56(s, 1H), 8.29(d, J=5.6 Hz, 1H), 7.47-7.41(m, 2H), 7.33-7.19(m, 3H), 7.15(d, J=7.7 Hz, 2H), 6.29(td, J=1.5 Hz, 5.6 Hz, 1H), 3.99(s, 2H), 2.07(s, 6H).
Mass, m/e: 402(M$^+$), 250(base).

Example 278

5-[(2-Chlorophenyl)acetylamino]-3-(2,6-dimethylphenyl)-4-(4-pyrimidinyl)isoxazole $^1$H-NMR(CDCl$_3$) δ: 11.58(s, 1H), 8.50(s, 1H), 8.28(d, J=5.6 Hz, 1H), 7.55-7.53(m, 1H), 7.51-7.49(m, 1H), 7.44-7.39(m, 2H), 7.31(t, J=7.5 Hz, 1H), 7.15(d, J=7.5 Hz, 2H), 6.28(td, J=1.2 Hz, 5.6 Hz, 1H), 4.09(s, 2H), 2.07(s, 6H).
Mass, m/e: 418(M$^+$), 250(base).

Example 279

3-(3,4-Dimethylphenyl)-5-(phenylacetylamino)-4-(4-pyrimidinyl)isoxazole a: 5-Amino-3-(3,4-dimethylphenyl)-4-(4-pyrimidinyl)isoxazole $^1$H-NMR(CDCl$_3$) δ: 9.01(d, J=1.3 Hz, 1H), 8.29(d, J=5.7 Hz, 1H), 7.34-7.12(m, 3H), 7.00-6.70(m, 3H), 2.35(s, 3H), 2.32(s, 3H).
Mass, m/e: 266(M$^+$), 121(base).

b: 3-(3,4-Dimethylphenyl)-5-(phenylacetylamino)-4-(4-pyrimidinyl)isoxazole $^1$H-NMR(CDCl$_3$) δ: 11.42(s, 1H), 8.48(bs, 1H), 8.33(d, J=5.4 Hz, 1H), 7.51-7.39(m, 5H), 7.24-7.22(m, 2H), 7.16-7.14(m, 1H), 6.85(dd, J=1.4 Hz, 5.4 Hz, 1H), 4.07(s, 2H), 2.34(s, 3H), 2.29(s, 3H).
Mass, m/e: 384(M$^+$), 91(base).

Example 280

3-(3,4-Dimethylphenyl)-5-[(2-fluorophenyl)acetylamino]-4-(4-pyrimidinyl)isoxazole $^1$H-NMR(CDCl$_3$) δ: 11.59(s, 1H), 8.60(bs, 1H), 8.36(d, J=5.4 Hz, 1H), 7.45-7.40(m, 2H), 7.27-7.16(m, 5H), 6.82(dd, J=1.5 Hz, 5.4 Hz, 1H), 3.97(s, 2H), 2.38(s, 3H), 2.34(s, 3H)
Mass, m/e: 402(M$^+$), 109(base). .

Example 281

5-[(2-Chlorophenyl)acetylamino]-3-(3,4-dimethylphenyl)-4-(4-pyrimidinyl)isoxazole ¹H-NMR(CDCl₃) δ: 11.47(s, 1H), 8.52(bs, 1H), 8.35(d, J=5.4 Hz, 1H), 7.54-7.52(m, 1H), 7.49-7.46(m, 1H), 7.43-7.38(m, 2H), 7.25-7.23(m, 2H), 7.17-7.15(m, 1H), 6.84(dd, J=1.4 Hz, 5.4 Hz, 1H), 4.07(s, 2H), 2.34(s, 3H), 2.29(s, 3H).
Mass, m/e: 418(M⁺), 250(base).

Example 282

3-(3,5-Dimethylphenyl)-5-(phenylacetylamino)-4-(4-pyrimidinyl)isoxazole a: 5-Amino-3-(3,5-dimethylphenyl)-4-(4-pyrimidinyl)isoxazole ¹H-NMR(CDCl₃) δ: 9.00(d, J=1.4 Hz, 1H), 8.28(d, J=5.8 Hz, 1H), 7.14(s, 1H), 7.11(s, 2H), 6.88(bs, 2H), 6.75(dd, J=1.4 Hz, 5.8 Hz, 1H), 2.34(s, 6H).
Mass, m/e: 266(M⁺), 121(base).

b: 3-(3,5-Dimethylphenyl)-5-(phenylacetylamino)-4-(4-pyrimidinyl)isoxazole

¹H-NMR(CDCl₃) δ: 11.42(bs, 1H), 8.48(s, 1H), 8.33(d, J=5.6 Hz, 1H), 7.48-7.39(m, 5H), 7.14(s, 1H), 7.04(s, 2H), 6.78(dd, J=1.5 Hz, 5.6 Hz, 1H), 3.93(s, 2H), 2.34(s, 6H).
Mass, m/e: 384(M⁺), 250(base).

Example 283

3-(3,5-Dimethylphenyl)-5-[(2-fluorophenyl)acetylamino]-4-(4-pyrimidinyl)isoxazole ¹H-NMR(CDCl₃) δ: 11.60(s, 1H), 8.60(s, 1H), 8.36(d, J=5.4 Hz, 1H), 7.46-7.40(m, 2H), 7.27-7.23(m, 1H), 7.19-7.17(m, 1H), 7.15(s, 1H), 7.06(s, 2H), 6.81(dd, J=1.2 Hz, 5.4 Hz, 1H), 3.96(d, J=0.8 Hz, 2H), 2.34(s, 6H).
Mass, m/e: 402(M⁺), 250(base).

Example 284

5-[(2-Chlorophenyl)acetylamino]-3-(3,5-dimethylphenyl)-4-(4-pyrimidinyl)isoxazole ¹H-NMR(CDCl₃) δ: 11.48(s, 1H), 8.52(s, 1H), 8.34(d, J=5.6 Hz, 1H), 7.53(m, 1H), 7.48(m, 1H), 7.41-7.39(m, 2H), 7.15(s, 1H), 7.05(s, 2H), 6.80(dd, J=1.5 Hz, 5.6 Hz, 1H), 4.08(s, 2H), 2.34(s, 6H).
Mass, m/e: 418(M⁺), 250(base).

Example 285

3-(4-Biphenyl)-5-(phenylacetylamino)-4-(4-pyrimidinyl)isoxazole a: 5-Amino-3-(4-biphenyl)-4-(4-pyrimidinyl)isoxazole ¹H-NMR(CDCl₃) δ: 9.03(d, J=1.5 Hz, 1H), 8.32(d, J=5.4 Hz, 1H), 7.75-7.38(m, 9H), 6.88(bs, 2H), 6.84(dd, J=1.5 Hz, 5.4 Hz, 1H)
Mass, m/e: 314(M⁺), 169(base).

b: 3-(4-Biphenyl)-5-(phenylacetylamino)-4-(4-pyrimidinyl)isoxazole

¹H-NMR(CDCl₃) δ: 11.43(s, 1H), 8.51(s, 1H), 8.37(d, J=5.8 Hz, 1H), 7.73-7.71(m, 2H), 7.65-7.63(m, 2H), 7.55-7.38(m, 10H), 6.87(dd, J=1.5 Hz, 5.8 Hz, 1H), 3.95(s, 2H).
Mass, m/e: 432(M⁺), 298(base).

Example 286

3-(4-Biphenyl)-5-[(2-fluorophenyl)acetylamino]-4-(4-pyrimidinyl)isoxazole

¹H-NMR(CDCl₃) δ: 11.61(s, 1H), 8.63(s, 1H), 8.40(d, J=5.4 Hz, 1H), 7.74-7.72(m, 2H), 7.66-7.64(m, 2H), 7.57-7.54(m, 2H), 7.50-7.38(m, 5H), 7.29-7.18(m, 2H), 6.89(dd, J=1.5 Hz, 5.4 Hz, 1H), 3.98(s, 2H).
Mass, m/e: 450(M⁺), 298(base).

Example 287

3-(4-Biphenyl)-5-[(2-chlorophenyl)acetylamino]-4-(4-pyrimidinyl)isoxazole

¹H-NMR(CDCl₃) δ: 11.49(s, 1H), 8.55(s, 1H), 8.38(d, J=5.8 Hz, 1H), 7.75-7.72(m, 2H), 7.66-7.64(m, 2H), 7.56-7.38(m, 9H), 6.90(dd, J=1.5 Hz, 5.8 Hz, 1H), 4.08(s, 2H).
Mass, m/e: 466(M⁺), 298(base).

Example 288

5-[(2-Chlorophenyl)acetylamino]-3-(2-fluoro-3-trifluoromethylphenyl)-4-(4-pyrimidinyl)isoxazole a: 5-Amino-3-(2-fluoro-3-trifluoromethylphenyl)-4-(4-pyrimidinyl)isoxazole ¹H-NMR(CDCl₃) δ: 9.03(d, J=1.7 Hz, 1H), 8.34(d, J=5.2 Hz, 1H), 7.83(t, J=7.7 Hz, 1H), 7.75(t, J=7.7 Hz, 1H), 7.43(t, J=7.7 Hz, 1H), 6.98(bs, 2H), 6.53(td, J=1.7 Hz, 5.2 Hz, 1H).
Mass, m/e: 324(M⁺), 179(base).

b: 5-[(2-Chlorophenyl)acetylamino]-3-(2-fluoro-3-trifluoromethylphenyl)-4-(4-pyrimidinyl)isoxazole ¹H-NMR(CDCl₃) δ: 11.50(s, 1H), 8.54(d, J=1.5 Hz, 1H), 8.41(d, J=5.2 Hz, 1H), 7.84(t, J=8.1 Hz, 1H), 7.75(t, J=7.7 Hz, 1H), 7.54-7.40(m, 5H), 6.60(td, J=1.5 Hz, 5.2 Hz, 1H), 4.07(s, 2H).
Mass, m/e: 476(M⁺), 351(base).

Example 289

5-[(2-Chlorophenyl)acetylamino]-3-(2-fluoro-4-trifluoromethylphenyl)-4-(4-pyrimidinyl)isoxazole a: 5-Amino-3-(2-fluoro-4-trifluoromethylphenyl)-4-(4-pyrimidinyl)isoxazole ¹H-NMR(CDCl₃) δ: 9.04(s, 1H), 8.37(d, J=5.6 Hz, 1H), 7.69(t, J=7.7 Hz, 1H), 7.60(t, J=8.1 Hz, 1H), 7.52(d, J=9.3 Hz, 1H), 6.94(bs, 2H), 6.56(td, J=5.6 Hz, 1H).
Mass, m/e: 324(M⁺), 52(base).

b: 5-[(2-Chlorophenyl)acetylamino]-3-(2-fluoro-4-trifluoromethylphenyl)-4-(4-pyrimidinyl)isoxazole $^1$H-NMR(CDCl$_3$) δ: 11.50(s, 1H), 8.55(d, J=1.5 Hz, 1H), 8.43(d, J=5.4 Hz, 1H), 7.69(t, J=7.7 Hz, 1H), 7.61(d, J=8.1 Hz, 1H), 7.54-7.40(m, 5H), 6.63(td, J=5.4 Hz, 1H), 4.10(s, 2H).
Mass, m/e: 476(M$^+$), 308(base).

Example 290

5-[(2-Chlorophenyl)acetylamino]-3-(2-fluoro-5-trifluoromethylphenyl)-4-(4-pyrimidinyl)isoxazole a: 5-Amino-3-(2-fluoro-5-trifluoromethylphenyl)-4-(4-pyrimidinyl)isoxazole $^1$H-NMR(DMSO-d$_6$) δ: 8.98(d, J=1.5 Hz, 1H), 8.43(d, J=5.6 Hz, 1H), 8.37(bs, 2H), 8.10(m, 1H), 8.02(dd, J=2.3 Hz, 6.2 Hz, 1H), 7.69(t, J=9.3 Hz, 1H), 6.59(td, J=1.5 Hz, 5.6 Hz, 1H).
Mass, m/e: 324(M$^+$), 179(base).

b: 5-[(2-Chlorophenyl)acetylamino]-3-(2-fluoro-5-trifluoromethylphenyl)-4-(4-pyrimidinyl)isoxazole $^1$H-NMR(CDCl$_3$) δ: 11.50(s, 1H), 8.55(d, J=1.5 Hz, 1H), 8.42(d, J=5.4 Hz, 1H), 7.87-7.83(m, 2H), 7.55-7.52(m, 1H), 7.49-7.47(m, 1H), 7.43-7.40(m, 2H), 7.35(t, J=9.3 Hz, 1H), 6.62(td, J=1.5 Hz, 5.4 Hz, 1H), 4.08(s, 2H).
Mass, m/e: 476(M$^+$), 308(base).

Example 291

3-(3-Fluoro-5-trifluoromethylphenyl)-5-(phenylacetylamino)-4-(4-pyrimidinyl)isoxazole a: 5-Amino-3-(3-fluoro-5-trifluoromethylphenyl)-4-(4-pyrimidinyl)isoxazole $^1$H-NMR(CDCl$_3$) δ: 9.05(d, J=1.4 Hz, 1H), 8.37(d, J=5.6 Hz, 1H), 7.62(s, 1H), 7.51(d, J=8.1 Hz, 1H), 7.46(d, J=8.5 Hz, 1H), 7.00(bs, 2H), 6.65(dd, J=1.4 Hz, 5.6 Hz, 1H).
Mass, m/e: 324(M$^+$), 59(base).

b: 3-(3-Fluoro-5-trifluoromethylphenyl)-5-(phenylacetylamino)-4-(4-pyrimidinyl)isoxazole $^1$H-NMR(CDCl$_3$) δ: 11.38(s, 1H), 8.52(d, J=1.4 Hz, 1H), 8.42(d, J=5.6 Hz, 1H), 7.56(s, 1H), 7.53-7.39(m, 7H), 6.68(dd, J=1.4 Hz, 5.6 Hz, 1H), 3.94(s, 2H).
Mass, m/e: 442(M$^+$), 91(base).

Example 292

5-[(2-Fluorophenyl)acetylamino]-3-(3-fluoro-5-trifluoromethylphenyl)-4-(4-pyrimidinyl)isoxazole $^1$H-NMR(CDCl$_3$) δ: 11.57(s, 1H), 8.65(d, J=1.4 Hz, 1H), 8.44(d, J=5.8 Hz, 1H), 7.57(s, 1H), 7.52(d, J=8.1 Hz, 1H), 7.47-7.41(m, 3H), 7.28(d, J=7.3 Hz, 1H), 7.20(t, J=9.6 Hz, 1H), 6.71(dd, J=1.4 Hz, 5.8 Hz, 1H), 3.97(s, 2H)
Mass, m/e: 460(M$^+$), 109(base).

Example 293

5-[(2-Chlorophenyl)acetylamino]-3-(3-fluoro-5-trifluoromethylphenyl)-4-(4-pyrimidinyl)isoxazole $^1$H-NMR(CDCl$_3$) δ: 11.44(s, 1H), 8.56(d, J=1.2 Hz, 1H), 8.43(d, J=5.4 Hz, 1H), 7.57(s, 1H), 7.55-7.41(m, 6H), 6.70(dd, J=1.2 Hz, 5.4 Hz, 1H), 4.07(s, 2H).
Mass, m/e: 476(M$^+$), 308(base).

Example 294

3-(1-Naphthyl)-5-(phenylacetylamino)-4-(4-pyrimidinyl)isoxazole a: 5-Amino-3-(1-naphthyl)-4-(4-pyrimidinyl)isoxazole $^1$H-NMR(CDCl$_3$) δ: 8.97(d, J=1.5 Hz, 1H), 8.05-8.00(m, 2H), 7.95(d, J=8.1 Hz, 1H), 7.73(d, J=8.1 Hz, 1H), 7.62-7.58(m, 2H), 7.55-7.50(m, 1H), 7.45-7.41(m, 1H), 7.00(bs, 2H), 6.06(dd, J=1.5 Hz, 5.8 Hz, 1H).
Mass, m/e: 288(M$^+$), 143(base).

b: 3-(1-Naphthyl)-5-(phenylacetylamino)-4-(4-pyrimidinyl)isoxazole $^1$H-NMR(CDCl$_3$) δ: 11.58(s, 1H), 8.44(s, 1H), 8.06-8.03(m, 2H), 7.93(d, J=8.5 Hz, 1H), 7.60-7.37(m, 10H), 6.10(dd, J=1.5 Hz, 5.4 Hz, 1H), 3.99(s, 2H).
Mass, m/e: 406(M$^+$), 91(base).

Example 295

5-[(2-Fluorophenyl)acetylamino]-3-(1-naphthyl)-4-(4-pyrimidinyl)isoxazole $^1$H-NMR(CDCl$_3$) δ: 11.76(s, 1H), 8.56(s, 1H), 8.08(d, J=5.4 Hz, 1H), 8.04(dd, J=2.3 Hz, 7.3 Hz, 1H), 7.94(d, J=8.5 Hz, 1H), 7.61-7.20(m, 9H), 6.13(dd, J=1.5 Hz, 5.6 Hz, 1H), 4.02(s, 2H).
Mass, m/e: 424(M$^+$), 109(base).

Example 296

5-[(2-Chlorophenyl)acetylamino]-3-(1-naphthyl)-4-(4-pyrimidinyl)isoxazole $^1$H-NMR(CDCl$_3$) δ: 11.63(s, 1H), 8.49(s, 1H), 8.07-8.03(m, 2H), 7.94(d, J=8.1 Hz, 1H), 7.61-7.38(m, 9H), 6.12(dd, J=1.5 Hz, 5.6 Hz, 1H), 4.12(s, 2H).
Mass, m/e: 440(M$^+$), 127(base).

Example 297

3-(2-Naphthyl)-5-(phenylacetylamino)-4-(4-pyrimidinyl)isoxazole a: 5-Amino-3-(2-naphthyl)-4-(4-pyrimidinyl)isoxazole $^1$H-NMR(CDCl$_3$) δ: 9.03(s, 1H), 8.23(d, J=5.8 Hz, 1H), 8.07(s, 1H), 7.98(d, J=8.5 Hz, 1H), 7.94-7.89(m, 2H), 7.62-7.55(m, 3H), 6.90(bs, 2H), 6.72(dd, J=1.2 Hz, 5.8 Hz, 1H)
Mass, m/e: 288(M$^+$), 127(base).

b: 3-(2-Naphthyl)-5-(phenylacetylamino)-4-(4-pyrimidinyl)isoxazole

¹H-NMR(CDCl₃) δ: 11.45(s, 1H), 8.50(s, 1H), 8.27(d, J=5.4 Hz, 1H), 8.01(s, 1H), 7.96(d, J=8.5 Hz, 1H), 7.93-7.87 (m, 2H), 7.62-7.55(m, 2H), 7.52-7.42(m, 6H), 6.74(dd, J=1.4 Hz, 5.4 Hz, 1H), 3.96(s, 2H).
Mass, m/e: 406(M⁺), 108(base).

Example 298

5-[(2-Fluorophenyl)acetylamino]-3-(2-naphthyl)-4-(4-pyrimidinyl)isoxazole

¹H-NMR(CDCl₃) δ: 11.63(s, 1H), 8.62(s, 1H), 8.30(d, J=5.4 Hz, 1H), 8.03(s, 1H), 7.98-7.88(m, 3H), 7.62-7.55(m, 2H), 7.49(dd, J=1.5 Hz, 8.5 Hz, 1H), 7.47-7.42(m, 2H), 7.29-7.18(m, 2H), 6.78(dd, J=1.5 Hz, 5.4 Hz, 1H), 4.00(s, 2H).
Mass, m/e: 424(M⁺), 109(base).

Example 299

5-[(2-Chlorophenyl)acetylamino]-3-(2-naphthyl)-4-(4-pyrimidinyl)isoxazole

¹H-NMR(CDCl₃) δ: 11.51(s, 1H), 8.55(s, 1H), 8.29(d, J=5.4 Hz, 1H), 8.03(s, 1H), 7.97(d, J=8.5 Hz, 1H), 7.93-7.87 (m, 2H), 7.62-7.39(m, 7H), 6.77(dd, J=1.5 Hz, 5.4 Hz, 1H), 4.09(s, 2H).
Mass, m/e: 440(M⁺), 272(base).

Example 300

3-(4-Fluorophenyl)-5-[(2-methoxymethoxyphenyl)acetylamino]-4-(4-pyrimidinyl)isoxazole a: Synthesis of ethyl-(2-methoxymethoxyphenyl)acetate

To 30 mL of an anhydrous acetone solution containing 0.6 g of ethyl 2'-hydroxyphenylacetate, 2 g of potassium carbonate was added and stirred at room temperature for 15 minutes. Then 1.02 mL of methoxymethylchloride was dropped under cooling with ice and the temperature of the system was raised to room temperature, followed by stirring for the whole night. After addition of water, the reaction solution was extracted with ether. The ether extract was dried over anhydrous magnesium sulfate, and from which the solvent was distilled off under reduced pressure. Thus obtained residue was purified on 60 g silica gel chromatography (eluent, ethyl acetate: hexane=1:3) to provide 0.69 g (yield: 93%) of the title compound as an oily substance.
¹H-NMR(CDCl₃) δ: 7.31-6.86(m, 4H), 5.17(s, 2H), 4.15 (q, J=7.1 Hz, 2H), 3.64(s, 2H), 3.45(s, 3H), 1.24(t, J=7.1 Hz, 3H).
Mass; m/e: 224(M⁺), 134(base).

b: Synthesis of (2-methoxymethoxyphenyl)acetic acid

To 20 mL of a methanol solution containing 0.69 g of ethyl-(2-methoxymethoxyphenyl)acetate, 16 mL of 1M aqueous sodium hydroxide solution was added and stirred at room temperature for 5 hours. From the reaction liquid the solvent was distilled off under reduced pressure and the residue was rendered acidic with 2M aqueous citric acid solution and extracted with ethyl acetate. The ethyl acetate extract was dried over anhydrous magnesium sulfate and thereafter the solvent therein was distilled off under reduced pressure to provide 0.47 g (yield: 77%) of the title compound as an oily substance.
¹H-NMR(CDCl₃) δ: 8.40-8.00(bs, 1H), 7.35-6.86(m, 4H), 5.18(s, 2H), 3.68(s, 2H), 3.44(s, 3H).
Mass; m/e: 196(M⁺), 134(base).

c: Synthesis of 3-(4-fluorophenyl)-5-[(2-methoxymethoxyphenyl)acetylamino]-4-(4-pyrimidinyl)isoxazole In 16 mL of THF, 047 g of (2-methoxymethoxyphenyl) acetic acid and 0.5 g of CDI were dissolved and stirred at room temperature for 2 hours. Then 16 mL of a THF solution containing 0.92 g of DBU and 0.31 g of 5-amino-3-(4-fluorophenyl)-4-pyrimidinyl isoxazole was added, followed by 21 hours' stirring at room temperature. From the reaction solution the solvent was distilled off under reduced pressure. To the residue water was added and extracted with ethyl acetate. The ethyl acetate extract was dried over anhydrous magnesium sulfate and removed of the solvent by distillation under reduced pressure. The residue was purified on 50 g silica gel chromatography (eluent, chloroform:methanol=100:1) and the residue was washed with ether-hexane to provide 0.32 g yield: 60%) of the title compound.
¹H-NMR(CDCl₃) δ: 11.38(bs, 1H), 8.44(d, J=1.5 Hz, 1H), 8.35(d, J=5.6 Hz, 1H), 7.47-7.41(m, 3H), 7.35(dd, J=1.5 Hz, 7.3 Hz, 1H), 7.24-7.12(m, 4H), 6.72(dd, J=1.5 Hz, 5.6 Hz, 1H), 5.18(s, 2H), 3.91(s, 2H), 3.32(s, 3H).
Mass, m/e: 434(M⁺), 240(base).

Example 301

3-(4-Fluorophenyl)-5-[(2-hydroxyphenyl)acetylamino]-4-(4-pyrimidinyl)isoxazole Fifty (50) mg of 3-(4-fluorophenyl)-5-[(2-methoxymethoxy-phenyl)acetylamino]-4-(4-pyrimidinyl)isoxazole was dissolved in 30 mL of dichloromethane and into which 460 mg of sodium hydrogensulfate reagent as fixed on silica gel was added, followed by 4 hours' stirring at room temperature. After addition of saturated aqueous sodium hydrogencarbonate solution, the reaction solution was extracted with chloroform. The chloroform extract was dried over anhydrous magnesium sulfate and from which the solvent was distilled off under reduced pressure. Thus obtained residue was washed with ether-hexane to provide 16 mg (yield: 34%) of the title compound.
¹H-NMR(CDCl₃) δ: 11.60(bs, 1H), 8.73(s, 1H), 8.37(d, J=5.6 Hz, 1H), 7.45(dd, J=5.4 Hz, 8.7 Hz, 2H), 7.31-7.26(m, 2H), 7.19(t, J=8.7 Hz, 2H), 7.00(dt, J=0.8 Hz, 7.3 Hz, 1H), 6.93(d, J=8.1 Hz, 1H), 6.76(dd, J=1.6 Hz, 5.6 Hz, 1H), 3.92(s, 2H).
Mass; m/e: 390(M⁺), 78(base).

Example 302

3-(4-Fluorophenyl)-5-[(3-methoxymethoxyphenyl)acetylamino]-4-(4-pyrimidinyl)isoxazole The title compound was synthesized in the manner similar to Example 300.
¹H-NMR(CDCl₃) δ: 11.42(bs, 1H), 8.61(d, J=1.3 Hz, 1H), 8.37(d, J=5.6 Hz, 1H), 7.48-7.43(m, 2H), 7.39(t, J=7.7 Hz, 1H), 7.22-7.17(m, 2H), 7.12(dd, J=1.9 Hz, 8.5 Hz, 1H), 7.70

(t, J=1.9 Hz, 1H), 7.03(d, J=7.7 Hz, 1H), 6.73(dd, J=1.3 Hz, 5.6 Hz, 1H), 5.19(s, 2H), 3.89(s, 2H), 3.45(s, 3H).
Mass, m/e: 434(M$^+$), 240(base).

Example 303

3-(4-Fluorophenyl)-5-[(3-hydroxyphenyl)acetylamino]-4-(4-pyrimidinyl)isoxazole

The title compound was synthesized in the manner similar to Example 301.
$^1$H-NMR(DMSO-d$_6$) δ: 11.36(bs, 1H), 9.48(s, 1H), 8.93 (d, J=1.5 Hz, 1H), 8.59(d, J=5.4 Hz, 1H), 7.58-7.54(m, 2H), 7.37-7.33(m, 2H), 7.19(t, J=7.7 Hz, 1H), 6.94(dd, J=1.5 Hz, 5.4 Hz, 1H), 6.80-6.78(m, 2H), 6.76-6.73(m, 1H), 3.73(s, 2H).
Mass, m/e: 390(M$^+$), 240(base).

Example 304

3-(4-Fluorophenyl)-5-[(4-methoxymethoxyphenyl) acetylamino]-4-(4-pyrimidinyl)isoxazole The title compound was synthesized in the manner similar to Example 300.
$^1$H-NMR(CDCl$_3$) δ: 11.40(bs, 1H), 8.58(s, 1H), 8.37(d, J=5.6 Hz, 1H), 7.47-7.43(m, 2H), 7.32-7.30(m, 2H), 7.22-7.12(m, 4H), 6.73(dd, J=1.6 Hz, 5.6 Hz, 1H), 5.23(s, 2H), 3.87(s, 2H), 3.52(s, 3H).
Mass, m/e: 434(M$^+$), 178(base).

Example 305

3-(4-Fluorophenyl)-5-[(4-hydroxyphenyl)acetylamino]-4-(4-pyrimidinyl)isoxazole

The title compound was synthesized in the manner similar to Example 301
$^1$H-NMR(DMSO-d$_6$) δ: 11.31(bs, 1H), 9.42(s, 1H), 8.87 (d, J=1.5 Hz, 1H), 8.59(d, J=5.4 Hz, 1H), 7.56(dd, J=5.8 Hz, 8.9 Hz, 2H), 7.35(t, J=8.9 Hz, 2H), 7.17(d, J=8.5 Hz, 2H), 6.93(dd, J=1.5 Hz, 5.4 Hz, 1H), 6.79(d, J=8.5 Hz, 2H), 3.70(s, 2H).
Mass, m/e: 390(M$^+$), 107(base).

Example 306

5-[(4-Aminophenyl)acetylamino]-3-(4-fluorophenyl)-4-(4-pyrimidinyl)isoxazole a: Synthesis of ethyl-4-tert-butoxycarbonylaminophenylacetate To 23 mL of a DMF solution containing 1.94 g of ethyl-4-aminophenyl acetate, 0.15 g of DMAP, 4.6 mL of triethylamine and 3 g of di-t-butyl dicarbonate were added, followed by 15 hours' stirring at room temperature. After addition of water, the reaction liquid was extracted with ether. The ether extract was dried over anhydrous magnesium sulfate and from which the solvent was distilled off under reduced pressure. Thus obtained residue was purified on 200 g silica gel chromatography (eluent, ethyl acetate:hexane=1:5) to provide 0.70 g (yield: 17%) of the title compound as an oily substance.
$^1$H-NMR(CDCl$_3$) δ: 7.29(d, J=8.4 Hz, 2H), 7.19(d, J=8.4 Hz, 2H), 6.44(bs, 1H), 4.12(q, J=7.3 Hz, 2H), 3.53(s, 2H), 1.50(s, 9H), 1.22(t, J=7.3 Hz, 3H).
Mass; m/e: 279(M$^+$), 57(base).

b: Synthesis of 5-[(4-t-butoxycarbonylaminophenyl) acetylamino]-3-(4-fluorophenyl)-4-(4-pyrimidinyl) isoxazole To 20 mL of a methanol solution containing 0.7 g of ethyl-4-tert-butoxycarbonylaminophenylacetate, 13 mL of 1M aqueous sodium hydroxide solution was added and stirred at room temperature for a day and night. The reaction liquid was concentrated under reduced pressure, and rendered acidic with 2M aqueous citric acid solution. The precipitated crystal was recovered by filtration under cooling with ice, to provide 0.40 g of 4-t-butoxycarbonylaminophenylacetic acid as pale yellow crystal. The compound was dissolved in 13 mL of THF, and to which 0.40 g of CDI was added, followed by 2 hours' stirring at room temperature. Then 13 mL of a THF solution containing 0.71 g of DBU and 0.26 g of 5-amino-3-(4-fluorophenyl)-4-pyrimidinylisoxazole were added and stirred for a night at room temperature. The solvent was distilled off of the reaction solution under reduced pressure and water was added to the residue, followed by extraction with ethyl acetate. The ethyl acetate extract was dried over anhydrous magnesium sulfate and removed of the solvent by distillation under reduced pressure. The residue was purified on 30 g silica gel chromatography (eluent, chloroform:methanol=100:1), and the crystalline residue was washed with ether-hexane to provide 0.364 g (yield: 46%) of the title compound.
$^1$H-NMR(CDCl$_3$) δ: 11.41(bs, 1H), 8.61(d, 1H), 8.37(d, J=5.6 Hz, 1H), 7.49-7.44(m, 4H), 7.32-7.30(m, 2H), 7.22-7.17(m, 2H), 6.73(dd, J=1.2 Hz, 5.6 Hz, 1H), 6.59(bs, 1H), 3.86(s, 2H), 1.52(s, 9H).
Mass, m/e: 489(M$^+$), 57(base).

c: Synthesis of 5-[(4-aminophenyl)acetylamino]-3-(4-fluorophenyl)-4-(4-pyrimidinyl)isoxazole To 59 mg of 5-[(4-t-butoxycarbonylaminophenyl)acetylamino]-3-(4-fluorophenyl)-4-(4-pyrimidinyl)isoxazole, 1 mL of TFA was added under cooling with ice, and the temperature was raised to room temperature, followed by 20 minutes' stirring. The reaction solution was neutralized with saturated aqueous sodium hydrogencarbonate solution under cooling with ice, and extracted with chloroform. The chloroform extract was dried over anhydrous magnesium sulfate and removed of the solvent by distillation under reduced pressure. The residue was washed with diethylether-hexane to provide 24 mg (yield: 51%) of the title compound.
$^1$H-NMR(CDCl$_3$) δ: 11.41(bs, 1H), 8.62(s, 1H), 8.36(d, J=5.6 Hz, 1H), 7.47-7.44(m, 2H), 7.20(d, J=8.5 Hz, 2H), 7.15(d, J=8.5 Hz, 2H), 6.75(d, J=8.5 Hz, 2H), 6.72(dd, J=1.5 Hz, 5.6 Hz, 1H), 3.79(s, 2H).
Mass, m/e: 389(M$^+$), 133(base).

Example 307

5-[(3-Aminophenyl)acetylamino]-3-(4-fluorophenyl)-4-(4-pyrimidinyl)isoxazole

The title compound was synthesized in the manner similar to Example 306.

a: 5-[(3-t-Butoxycarbonylaminophenyl)acetylamino]-3-(4-fluorophenyl)-4-(4-pyrimidinyl)isoxazole $^1$H-NMR(CDCl$_3$) δ: 11.43(bs, 1H), 8.62(d, J=1.2 Hz, 1H), 8.36(d, J=5.4 Hz, 1H), 7.63(s, 1H), 7.47-7.43(m, 2H), 7.37(t, J=8.1 Hz, 1H), 7.28-7.26(m, 1H), 7.22-7.16(m, 2H), 7.06(d, J=7.7 Hz, 1H), 6.72(dd, J=1.2 Hz, 5.4 Hz, 1H), 6.58(bs, 1H), 3.89(s, 2H), 1.50(s, 9H).

Mass, m/e: 489(M$^+$), 57(base).

b: 5-[(3-Aminophenyl)acetylamino]-3-(4-fluorophenyl)-4-(4-pyrimidinyl)isoxazole $^1$H-NMR(CDCl$_3$) δ: 11.42(bs, 1H), 8.68(d, J=1.2 Hz, 1H), 8.36(d, J=5.4 Hz, 1H), 7.47-7.44(m, 2H), 7.27-7.17(m, 3H), 6.76-6.69(m, 4H), 3.81(s, 2H).

Mass, m/e: 389(M$^+$), 133(base).

Example 308

3-(4-Fluorophenyl)-5-[2-(2-chlorophenyl)propionylamino]-4-(4-pyrimidinyl)isoxazole a: Synthesis of 2-(2-chlorophenyl)propionic acid To 1 g of 2-chlorophenylacetic acid, 8.8 mL of 2M LDA heptane, THF, ethylbenzene solution was dropped under cooling with ice, and further 1.58 g of HMPA and 5 mL of THF were added followed by an hour's stirring at room temperature. Then 1.25 g of methyl iodide was added under cooling with ice and stirred at room temperature for 30 minutes. The reaction solution was poured into ice water, rendered acidic with 10% aqueous hydrochloric acid and extracted with ethyl acetate. The ethyl acetate extract was dried over anhydrous magnesium sulfate and thereafter removed of the solvent by distillation under reduced pressure. The residue was purified on 30 g silica gel column chromatography (eluent, chloroform:methanol=20:1) to provide 0.928 g (yield: 86%) of the title compound as a pale yellow, oily substance.

$^1$H-NMR(CDCl$_3$) δ: 7.50-7.10(m, 4H), 4.27(q, J=7.2 Hz, 1H), 1.52(d, J=7.2 Hz, 3H).

Mass, m/e: 184(M$^+$), 139(base).

b: Synthesis of 3-(4-fluorophenyl)-5-[2-(2-chlorophenyl)propionylamino]-4-[4-pyrimidinyl]isoxazole In 5 mL of THF, 0.144 g of 2-(2-chlorophenyl)propionic acid and 0.126 g of CDI were dissolved and stirred at room temperature for an hour. Then 5 mL of THF solution containing 0.237 g of DBU and 0.1 g of 5-amino-3 (4-fluorophenyl)-4-4-pyrimidinyl isoxazole was added and stirred at room temperature for 3 hours. The solvent was distilled off from the reaction solution under reduced pressure, and water was added to the residue which was then extracted with ethyl acetate. The ethyl acetate extract was dried over anhydrous magnesium sulfate, removed of the solvent by distillation under reduced pressure, and the residue was purified on 20 g silica gel chromatography (eluent, chloroform:methanol=50:1). Washing the residue with ether, 0.118 g (yield: 72%) of the title compound was obtained.

$^1$H-NMR(CDCl$_3$) δ: 11.53(s, 1H), 8.66(d, J=1.5 Hz, 1H), 8.38(d, J=5.8 Hz, 1H), 7.52-7.43(m, 4H), 7.39-7.30(m, 2H), 7.23-7.17(m, 2H), 6.73(dd, J=1.5 Hz, 5.8 Hz, 1H), 4.45(q, J=7.1 Hz, 1H), 1.67(d, J=7.1 Hz, 3H).

Mass, m/e: 422(M$^+$), 240(base).

Example 309

3-(4-Fluorophenyl)-5-[2-(2,6-dichlorophenyl)propionylamino]-4-(4-pyrimidinyl)isoxazole The title compound was synthesized in the manner similar to Example 308.

a: 2-(2,6-Dichlorophenyl)propionic acid $^1$H-NMR(CDCl$_3$) δ: 7.45-7.00(m, 3H), 4.58(q, J=7.2 Hz, 1H), 1.54(d, J=7.2 Hz, 3H).

Mass, m/e: 218(M$^+$), 183(base).

b: 3-(4-Fluorophenyl)-5-[2-(2,6-dichlorophenyl)propionylamino]-4-(4-pyrimidinyl)isoxazole $^1$H-NMR(CDCl$_3$) δ: 11.65(s, 1H), 8.37-8.34(m, 2H), 7.52-7.38(m, 4H), 7.31(t, J=8.1 Hz, 1H), 7.20(t, J=8.7 Hz, 2H), 6.75(dd, J=1.4 Hz, 5.6 Hz, 1H), 4.77(q, J=6.9 Hz, 1H), 1.70 (d, J=6.9 Hz, 3H).

Mass, m/e: 456(M$^+$), 240(base).

Example 310

3-(4-Fluorophenyl)-4-[4-(2-methylthio)pyrimidinyl]-5-(phenylacetylamino)isoxazole a: Synthesis of 4-methyl-2-methylthiopyrimidine To 400 mL of a toluene solution containing 25.5 g of 2-(4-methylpyrimidine)thiol, 50 mL of DMFDMA and then 42 mL of diisopropylethylamine were added and heated under reflux for 6.5 hours. The reaction solution was cooled, removed of the solvent by distillation under reduced pressure, and the residue was extracted with chloroform after addition of water. The chloroform extract was dried over anhydrous magnesium sulfate and removed of the solvent by distillation under reduced pressure. The residue was purified on 120 g silica gel column chromatography (eluent, chloroform) to provide 24.13 g (yield: 85%) of the title compound as a brown oily substance.

$^1$H-NMR(CDCl$_3$) δ: 8.36(d, J=5.1 Hz, 1H), 6.80(d, J=5.1 Hz, 1H), 2.56(s, 3H), 2.45(s, 3H).

b: Synthesis of 1-fluoro-4-[4-(2-methylthiopyrimidinyl)acetyl]benzene

Into 100 mL of a THF solution containing 12.64 g of 4-methyl-2-thiopyrimidine, 54.1 mL of 2M LDA heptane, THF, ethylbenzene solution was dropped at −78° C., and thereafter stirred for 15 minutes at −78° C. Then 100 mL of a THF solution containing 15.17 g of ethyl-4-fluorobenzoate was dropped thereinto at −78° C. After the end of the dropping, the solution was stirred for an hour while slowly raising the temperature to room temperature. Fifty (50) mL of saturated aqueous ammonium chloride solution and 50 mL of water were added to the reaction solution, followed by extraction with ethyl acetate. The ethyl acetate extract was dried over anhydrous magnesium sulfate and removed of the solvent by distillation under reduced pressure. The residue was dissolved in chloroform and purified on 120 g silica gel column chromatography (eluent, hexane:ethyl acetate=4:1). Washing the purified residue with hexane, 3.39 g (yield: 14%) of the title compound was obtained as a pale yellow crystal.

¹H-NMR(CDCl₃) δ: 14.61(s, 1H), 8.30(d, J=5.4 Hz, 1H), 7.83(dd, J=5.3 Hz, 8.9 Hz, 2H), 7.10(t, J=8.9 Hz, 2H), 6.63(d, J=5.4 Hz, 1H), 5.90(s, 1H), 2.61(s, 3H).

c: Synthesis of 5-(4-fluorophenyl)-4-[4-(2-methylthiopyrimidinyl)]isoxazole

A mixture of 6.12 g of 1-fluoro-4-[4-(2-methylthiopyrimidinyl)-acetyl]benzene and 13.90 g of DMFDMA was heated under reflux for 45 minutes. The reaction solution was cooled and from which DMFDMA was distilled off under reduced pressure. To the residue 100 mL of ethanol and then 8.12 g of hydroxylamine hydrochloride were added and heated under reflux for 30 minutes. From the reaction solution the solvent was distilled off under reduced pressure, and to the residue water was added. Whereupon precipitated solid was recovered by filtration, washed with water, dissolved in chloroform, dried over anhydrous magnesium sulfate, and removed of the solvent by distillation under reduced pressure. The residue was washed with ether-hexane to provide 5.10 g (yield: 76%) of the title compound as a colorless crystal.

¹H-NMR(CDCl₃) δ: 8.73(s, 1H), 8.45(d, J=5.2 Hz, 1H), 7.90-7.65(m, 2H), 7.35-7.05(m, 2H), 6.98(d, J=5.2 Hz, 1H), 2.50(s, 3H).
Mass, m/e: 287(M⁺), 95(base).

d: Synthesis of 3-(4-fluorophenyl)-2-[4-(methylthiopyrimidinyl)]-3-oxopropionitrile To 60 mL of an ethanol solution containing 5.09 g of 5-(4-fluorophenyl)-4-[4-(2-methylthiopyrimidinyl)]isoxazole, 30 mL of 1N aqueous NaOH solution was added and stirred at 60° C. for 2.5 hours. The reaction solution was cooled and then concentrated to about ⅓ under reduced pressure, to which ice water (10 mL) was added. The solution was then neutralized with 10% aqueous HCl solution and the precipitated solid was recovered by filtration. The solid was washed with water and dried under reduced pressure to provide 4.95 g (yield: 97%) of the title compound as a pale yellow crystal.

¹H-NMR(CDCl₃) δ: 8.15(d, J=6.4 Hz, 1H), 7.80(dd, J=5.6 Hz, 9.0 Hz, 2H), 7.80-7.55(m, 1H), 7.29(t, J=9.0 Hz, 2H), 2.64(s, 3H).

e: Synthesis of 4-(2-methylthiopyrimidinyl)acetonitrile

To 200 mL of an ethanol solution containing 4.94 g of 2-(4-fluorophenyl)-[4-(2-methylthiopyrimidinyl)]acetonitrile, 1.29 g of hydrazine monohydrate was added and heated under reflux for 3.5 hours. The reaction solution was removed of the solvent by distillation under reduced pressure, and the residue was purified on 50 g silica gel column chromatography (eluent, chloroform) to provide 2.44 g (yield: 86%) of the title compound as a pale yellow crystal.

¹H-NMR(CDCl₃) δ: 8.55(d, J=5.1 Hz, 1H), 7.11(d, J=5.1 Hz, 1H), 3.83(s, 2H), 2.57(s, 3H).

f: Synthesis of 5-amino-3-(4-fluorophenyl)-4-[4-(2-methylthio)pyrimidinyl]isoxazole To 30 mL of an ethanol solution containing 0.54 g of sodium ethoxide, 20 mL of a THF solution containing 1.20 g of 4-(2-methylthiopyrimidinyl)acetonitrile was added and stirred for an hour at room temperature. Then 20 mL of an ethanol solution containing 1.26 g of 4-fluorobenzhydroximoyl chloride was added under cooling with ice, followed by 1.5 hours' stirring at room temperature. From the reaction solution the solvent was distilled off under reduced pressure, and water was added to the residue which then was extracted with chloroform. The chloroform extract was dried over anhydrous magnesium sulfate, decolorized with active carbon and removed of the solvent by distillation under reduced pressure. The residue was purified on 50 g silica gel column chromatography (eluent, chloroform) and washed with ether-hexane to provide 1.57 g (yield: 71%) of the title compound as a pale yellow crystal.

¹H-NMR(CDCl₃) δ: 8.14(d, J=5.6 Hz, 1H), 7.62-7.08(m, 4H), 6.85-6.70(bs, 2H), 6.36(d, J=5.6 Hz, 1H), 2.57(s, 3H).
Mass, m/e: 302(M⁺, base).

g: Synthesis of 3-(4-fluorophenyl)-4-[4-(2-methylthio)pyrimidinyl]-5-(phenylacetylamino)isoxazole In 30 mL of THF, 0.48 g of imidazole and 4.26 g of DBU were dissolved, to which 0.99 g of phenylacetyl chloride was added under stirring and cooling with ice, followed by an hour's stirring at room temperature. Then 20 mL of a THF solution containing 1.06 g of 5-amino-3-(4-fluorophenyl)-4-[4-(2-methylthio)pyrimidinyl]isoxazole was added and stirred for 24 hours at room temperature. Water was added to the reaction solution, which then was extracted with ethyl acetate. The ethyl acetate extract was dried over anhydrous magnesium sulfate and removed of the solvent by distillation under reduced pressure. The residue was purified on 60 g silica gel column chromatography (eluent, chloroform) and washed with ether-hexane to provide 0.080 g (yield: 29%) of the title compound as a pale yellow crystal.

¹H-NMR(CDCl₃) δ: 11.35-11.31(bs, 1H), 8.25(d, J=5.5 Hz, 1H), 7.60-7.05(m, 9H), 6.45(d, J=5.5 Hz, 1H), 3.92(s, 2H), 2.62(s, 3H).

Example 311

3-(4-Fluorophenyl)-4-[4-(2-methylsulfinyl)pyrimidinyl]-5-(phenylacetylamino)isoxazole To 20 mL of a methanol suspension containing 0.18 g of 3-(4-fluorophenyl)-4-[4-(2-methylthio)pyrimidinyl]-5-(phenylacetylamino)isoxazole, 10 mL of an aqueous solution containing 0.79 g of OXONE was added and stirred at room temperature for 2.5 hours. The reaction solution was concentrated under reduced pressure to about ¼ in the liquid volume, to which 30 mL of saturated aqueous NaHCO₃ solution was added and extracted with chloroform. The chloroform extract was dried over anhydrous magnesium sulfate and removed of the solvent by distillation under reduced pressure. The residue was washed with ether to provide 0.15 g (yield: 78%) of the title compound as a pale yellow crystal.

¹H-NMR(CDCl₃) δ: 12.50-12.35(bs, 1H), 8.48(d, J=5.4 Hz, 1H), 7.65-7.10(m, 9H), 6.82(d, J=5.4 Hz, 1H), 4.01(s, 2H), 2.98(s, 3H).
Mass, m/e: 436(M⁺), 91(base).

Example 312

3-(4-Fluorophenyl)-4-[4-(2-methoxypyrimidinyl)]-5-(phenylacetylamino)isoxazole a: Synthesis of 5-amino-3-(4-fluorophenyl)-4-[4-(2-methylsulfinyl)pyrimidinyl]isoxazole To 100 mL of a methanol solution containing 0.7 g of 5-amino-3-(4-fluorophenyl)-4-[4-(2-methylthio)pyrimidinyl]isoxazole, 50 mL of an aqueous solution containing 1.71 g of OXONE was added, and stirred at room temperature for 20 minutes. The reaction solution was concentrated to about ⅓ in the liquid volume, to which 50 mL of saturated aqueous NaHCO$_3$ solution was added and extracted with chloroform. The chloroform extract was dried over anhydrous magnesium sulfate and removed of the solvent by distillation under reduced pressure to provide 0.74 g (yield: 100%) of the title compound as a pale yellow crystal.

$^1$H-NMR(CDCl$_3$) δ: 8.33(d, J=5.6 Hz, 1H), 7.70-7.05(m, 6H), 6.68(d, J=5.6 Hz, 1H), 2.93(s, 3H).

b: Synthesis of 5-amino-3-(4-fluorophenyl)-4-[4-(2-methoxypyrimidinyl)]isoxazole To 0.055 g of 5-amino-3-(4-fluorophenyl)-4-[4-(2-methylsulfinyl)pyrimidinyl]isoxazole, 5 mL of a methanol solution containing 0.014 g of sodium methoxide was added, followed by 20 minutes' heating under reflux. The reaction solution was cooled and then removed of the solvent by distillation under reduced pressure. After addition of water to the residue, the residue was extracted with chloroform. The chloroform extract was dried over anhydrous magnesium sulfate and removed of the solvent by distillation under reduced pressure. The residue was washed with hexane to provide 0.032 g (yield: 65%) of the title compound as a colorless crystal.

$^1$H-NMR(CDCl$_3$) δ: 8.13(d, J=5.6 Hz, 1H), 7.51(dd, J=5.4 Hz, 8.7 Hz, 2H), 7.20(t, J=8.7 Hz, 2H), 6.85-6.75(bs, 2H), 6.34(d, J=5.6 Hz, 1H), 4.00(s, 3H).

Mass, m/e: 286(M$^+$), 111(base).

c: Synthesis of 3-(4-fluorophenyl)-4-[4-(2-methoxypyrimidinyl)]-5-(phenylacetylamino)isoxazole In 3 mL of THF, 0.014 g of imidazole and 0.124 g of DBU were dissolved, and to the solution 0.028 g of phenylacetyl chloride was added under stirring and cooling with ice, followed by 2 hours' stirring at room temperature. Then 3 mL of a THF solution containing 0.029 g of 5-amino-3-(4-fluorophenyl)-4-[4-(2-methoxypyrimidinyl)]-isoxazole was added and stirred for 26 hours at room temperature. Water was added to the reaction solution which then was extracted with ethyl acetate. The ethyl acetate extract was dried over anhydrous magnesium sulfate and removed of the solvent by distillation under reduced pressure. The residue was purified over preparative chromatography (developer, chloroform) to provide 0.019 g (yield: 46%) of the title compound as a colorless crystal.

$^1$H-NMR(CDCl$_3$) δ: 11.58(s, 1H), 8.22(d, J=5.5 Hz, 1H), 7.52-7.43(m, 5H), 7.38(t, J=7.3 Hz, 2H), 7.31(t, J=7.3 Hz, 1H), 7.20(t, J=8.6 Hz, 2H), 4.04(s, 3H), 3.92(s, 2H).

Mass, m/e: 404(M$^+$), 270(base).

Example 313

4-[4-(2-Amino)pyrimidinyl]-3-(4-fluorophenyl)-5-(phenylacetylamino)isoxazole a: Synthesis of 2-[1-(2,5-dimethylpyrrolyl)]-4-methylpyrimidine A mixture of 10.28 g of 2-amino-4-methylpyrimidine and 12.90 g of acetonyl acetone was stirred at 200° C. for 8 hours. After cooling, ether was added to the residue and the solid was filtered. The residue was further washed with ether. The filtrate and the washing were combined, from which the solvent was distilled off under reduced pressure. To the filtered solid 8.02 g of acetonyl acetone was added and stirred at 200° C. for 3 hours. After cooling the system, ether was added to the residue and the solid was filtered and washed with ether. The filtrate and the washing were combined, from which the solvent was distilled off under reduced pressure. The two residues were combined, dissolved in chloroform and purified on 150 g silica gel column chromatography (eluent, hexane:ethyl acetate=5:1→10:1) to provide 6.97 g (yield: 40%) of the title compound as a pale yellow oily substance.

$^1$H-NMR(CDCl$_3$) δ: 8.59(d, J=4.8 Hz, 1H), 7.03(d, J=4.8 Hz, 1H), 5.88(s, 2H), 2.55(s, 3H), 2.32(s, 6H).

b: Synthesis of 4-{2-[1-(2,5-dimethylpyrrolyl)]pyrimidinyl}acetonitrile

A mixture of 8.18 g of 2-[1-(2,5-dimethylpyrrolyl)]-4-methylpyrimidine and 22.83 g of t-butoxybisdimethylaminomethane was stirred at 110° C. for 45 minutes. The reaction solution was cooled, and from which t-butoxybisdimethylaminomethane was distilled off under reduced pressure. To the residue 150 mL of water and 12.36 g of hydroxylamine-O-sulfonic acid were added and stirred at room temperature for 45 minutes. The reaction solution was rendered basic by the addition of sodium hydrogencarbonate, and extracted with ethyl acetate. The ethyl acetate extract was dried over anhydrous magnesium sulfate and from which the solvent was distilled off under reduced pressure. The residue was dissolved in chloroform and purified on 120 g silica gel column chromatography (eluent, hexane:ethyl acetate=4:1→2:1) to provide 1.923 g (yield: 21%) of the title compound as a pale yellow crystal.

$^1$H-NMR(CDCl$_3$) δ: 8.79(d, J=5.3 Hz, 1H), 7.28(d, J=5.3 Hz, 1H), 5.91(s, 2H), 3.92(s, 2H), 2.38(s, 6H).

c: Synthesis of 5-amino-4-(4-{2-[1-(2,5-dimethylpyrrolyl)]pyrimidinyl})-3-(4-fluorophenyl)isoxazole To 10 mL of a methanol solution containing 0.12 g of sodium methoxide, 10 mL of a THF solution containing 0.38 g of 4-{2-[1-(2,5-dimethylpyrrolyl)]pyrimidinyl}acetonitrile was added and stirred at room temperature for 30 minutes. Then 10 mL of a methanol solution containing 0.31 g of 4-fluorobenzhydroxymoyl chloride was added under cooling with ice, followed by an hour's stirring at room temperature. From the reaction solution the solvent was distilled off under reduced pressure, and to the residue water was added, followed by extraction with chloroform. The chloroform extract was dried over anhydrous magnesium sulfate, decolorized with active carbon, and removed of the solvent by distillation under reduced pressure. The residue was purified on 25 g silica gel column chromatography (eluent, chloroform) and washed with ether-hexane to provide 0.21 g (yield: 35%) of the title compound as a pale yellow crystal.

$^1$H-NMR(CDCl$_3$) δ: 8.38(d, J=5.5 Hz, 1H), 7.70-7.10(m, 4H), 6.85-6.65(bs, 2H), 6.60(d, J=5.5 Hz, 1H), 5.91(s, 2H), 2.30(s, 6H).

Mass, m/e: 349(M$^+$, base).

d: Synthesis of 4-(4-{2-[1-(2,5-dimethylpyrrolyl)]}pyrimidinyl)-3-(4-fluorophenyl)-5-(phenylacetylamino)isoxazole In 5 mL of THF, 0.058 g of imidazole and 0.261 g of DBU were dissolved, and 0.121 g of phenylacetyl chloride was added to the solution under cooling with ice and stirring, followed by 30 minutes' stirring at room temperature. Then 5 mL of a THF solution containing 0.06 g of 5-amino-4-(4-{2-[1-(2,5-dimethylpyrrolyl)]-pyrimidinyl})-3-(4-fluorophenyl)isoxazole was added and stirred for 3 hours at room temperature. Water was added to the reaction solution which then was extracted with ethyl acetate. The ethyl acetate extract was dried over anhydrous magnesium sulfate and removed of the solvent by distillation under reduced pressure. The residue was purified on 10 g silica gel column chromatography (eluent, chloroform) and washed with ether-hexane to provide 0.066 g (yield: 82%) of the title compound as a colorless crystal.

$^1$H-NMR(CDCl$_3$) δ: 11.32(s, 1H), 8.49(d, J=5.3 Hz, 1H), 7.53(dd, J=5.3 Hz, 9.0 Hz, 2H), 7.25-7.15(m, 5H), 7.07-7.02 (m, 2H), 6.67(d, J=5.3 Hz, 1H), 6.05(s, 2H), 3.73(s, 2H), 2.34(s, 6H).

Mass, m/e: 467(M$^+$), 91(base).

e: Synthesis of 4-[4-(2-aminopyrimidinyl)]-3-(4-fluorophenyl)-5-(phenylacetylamino)isoxazole A few drops of water was added to a mixture of 0.05 g of 4-(4-{2-[1-(2,5-dimethylpyrrolyl)]}pyrimidinyl)-3-(4-fluorophenyl)-5-(phenylacetylamino)isoxazole, 1 mL of TFA and 1 mL of benzene, and stirred for a whole night at 40° C. Water was added to the reaction solution under cooling with ice. After rendering the reaction solution basic with saturated aqueous sodium hydrogencarbonate solution, it was extracted with chloroform. The chloroform extract was dried over anhydrous sodium sulfate and removed of the solvent by distillation under reduced pressure. The residue was purified on preparative chromatography (developer, chloroform:methanol=50:1) and washed with ether-hexane to provide 0.020 g (yield: 48%) of the title compound as a colorless crystal.

$^1$H-NMR(CDCl$_3$) δ: 11.16(s, 1H), 7.96(d, J=5.2 Hz, 1H), 7.52-7.38(m, 7H), 7.17(t, J=8.7 Hz, 2H), 6.06(d, J=5.2 Hz, 1H), 4.35-4.20(bs, 2H), 3.97(s, 2H).

Mass, m/e: 389(M$^+$), 255(base).

Example 314

4-[4-(2-Aminopyrimidinyl)]-5-[(2-chlorophenyl)acetylamino]-3-(4-fluorophenyl)isoxazole a: Synthesis of 5-[(2-chlorophenyl)acetylamino]-4-(4-{2-[1-(2,5-dimethylpyrrolyl)]}pyrimidinyl)-3-(4-fluorophenyl)isoxazole To 10 mL of a THF solution containing 0.195 g of 2'-chlorophenylacetic acid, 0.186 g of CDI was added and stirred for 1.5 hours at room temperature. Then 10 mL of a THF solution containing 0.347 g of DBU and 0.2 g of 5-amino-4-(4-{2-[1-(2,5-dimethylpyrrolyl)]pyrimidinyl})-3-(4-fluorophenyl)isoxazole was added and stirred for 2.5 hours at room temperature. From the reaction solution the solvent was removed by distillation under reduced pressure and water was added to the residue, followed by extraction with ethyl acetate. The organic layer was dried over anhydrous magnesium sulfate and removed of the solvent by distillation under reduced pressure. The residue was purified on 20 g silica gel column chromatography (eluent, chloroform) and washed with ether-hexane to provide 0.248 g (yield: 86%) of the title compound as a pale yellow crystal.

$^1$H-NMR(CDCl$_3$) δ: 11.13(s, 1H), 8.49(d, J=5.4 Hz, 1H), 7.53(dd, J=5.2 Hz, 8.7 Hz, 2H), 7.30-7.07(m, 6H), 6.68(d, J=5.4 Hz, 1H), 5.97(s, 2H), 3.92(s, 2H), 2.31(s, 6H)

Mass, m/e: 501(M$^+$), 94(base). .

b: Synthesis of 4-[4-(2-aminopyrimidinyl)]-5-[(2-chlorophenyl)acetylamino]-3-(4-fluorophenyl)isoxazole A few drops of water was added to a mixture of 0.2 g of 5-[(2-chlorophenyl)acetylamino]-4-(4-{2-[1-(2,5-dimethylpyrrolyl)]}-pyrimidinyl)-3-(4-fluorophenyl)isoxazole, 2 mL of TFA and 2 mL of benzene, followed by 4 hours' stirring at 50° C. After adding water to the reaction solution under cooling with ice, the solution was rendered basic with saturated aqueous sodium hydrogencarbonate solution and extracted with chloroform. The chloroform extract was dried over anhydrous sodium sulfate and removed of the solvent by distillation under reduced pressure. The residue was purified on 10 g silica gel column chromatography (eluent, chloroform:methanol=50:1) and washed with ether to provide 0.083 g (yield: 49%) of the title compound as a pale yellow crystal.

$^1$H-NMR(CDCl$_3$) δ: 11.17(s, 1H), 8.00(d, J=5.4 Hz, 1H), 7.54-7.45(m, 4H), 7.40-7.34(m, 2H), 7.23-7.16(m, 2H), 6.11 (d, J=5.4 Hz, 1H), 4.66-4.56(bs, 2H), 4.09(s, 2H).

Mass, m/e: 423(M$^+$), 255(base).

Hereinafter the compounds of Examples 315-317 were prepared in the manner similar to Example 314.

Example 315

4-[4-(2-Aminopyrimidinyl)]-5-[(2,6-dichlorophenyl)acetylamino]-3-(4-fluorophenyl)isoxazole a: 5-[(2,6-Dichlorophenyl)acetylamino]-4-(4-{2-[1-(2,5-dimethylpyrrolyl)]}pyrimidinyl)-3-(4-fluorophenyl)isoxazole $^1$H-NMR(CDCl$_3$) δ: 11.12(s, 1H), 8.51(d, J=5.4 Hz, 1H), 7.54(dd, J=5.4 Hz, 8.8 Hz, 2H), 7.28-7.21(m, 4H), 7.13(dd, J=7.5 Hz, 8.8 Hz, 1H), 6.70(d, J=5.4 Hz, 1H), 5.94(s, 2H), 4.22(s, 2H), 2.32(s, 6H).

Mass, m/e: 535(M$^+$), 94(base).

b: 4-[4-(2-Aminopyrimidinyl)]-5-[(2,6-dichlorophenyl)acetylamino]-3-(4-fluorophenyl)isoxazole $^1$H-NMR(CDCl$_3$) δ: 11.25-11.10(bs, 1H), 8.03(d, J=5.4 Hz, 1H), 7.49(dd, J=5.2 Hz, 8.7 Hz, 2H), 7.42(d, J=7.9 Hz, 2H), 7.28(d, J=7.9 Hz, 1H), 7.19(t, J=8.7 Hz, 2H), 6.13(d, J=5.4 Hz, 1H), 4.90-4.75(bs, 2H), 4.38(s, 2H).

Mass, m/e: 457(M$^+$), 255(base).

Example 316

4-[4-(2-Aminopyrimidinyl)]-3-(4-fluorophenyl)-5-[(2-methoxyphenyl)acetylamino]isoxazole a: 4-(4-{2-[1-(2,5-Dimethylpyrrolyl)]}pyrimidinyl)-3-(4-fluorophenyl)-5-[(2-methoxyphenyl)acetylamino]isoxazole $^1$H-NMR(CDCl$_3$) δ: 10.89(s, 1H), 8.46(d, J=5.4 Hz, 1H), 7.51(dd, J=5.0 Hz, 8.9 Hz, 2H), 7.26-7.15(m, 3H), 7.00(dd, J=1.5 Hz, 7.3 Hz, 1H), 6.79-6.72(m, 2H), 6.65(d, J=5.4 Hz, 1H), 5.97(s, 2H), 3.76(s, 2H), 3.67(s, 3H), 2.31(s, 6H)

Mass, m/e: 497(M$^+$), 91(base). .

b: 4-[4-(2-Aminoipyrimidinyl)]-3-(4-fluorophenyl)-5-[(2-methoxyphenyl)acetylamino]isoxazole $^1$H-NMR(CDCl$_3$) δ: 11.09(s, 1H), 7.95(d, J=5.4 Hz, 1H), 7.48-7.36(m, 4H), 7.16(t, J=8.6 Hz, 2H), 7.05(t, J=7.3 Hz, 1H), 7.00(d, J=8.1 Hz, 1H), 6.05(d, J=5.4 Hz, 1H), 4.37(bs, 2H), 3.88(s, 2H), 3.84(s, 3H).
Mass, m/e: 419(M$^+$), 148(base).

Example 317

3-(4-Fluorophenyl)-5-(2-phenylpropionylamino)-4-{4-(2-aminopyrimidinyl)}isoxazole a: 4-(4-{2-[1-(2,5-Dimethylpyrrolyl)]}pyrimidinyl)-3-(4-fluorophenyl)-5-(2-phenylpropionylamino)isoxazole $^1$H-NMR(CDCl$_3$) δ: 11.30(s, 1H), 8.46(d, J=5.4 Hz, 1H), 7.55-7.48(m, 2H), 7.25-7.12(m, 5H), 7.02-6.97(m, 2H), 6.65 (d, J=5.4 Hz, 1H), 6.07(s, 2H), 3.66(q, J=7.0 Hz, 1H), 2.30(s, 6H), 1.54(d, J=7.0 Hz, 3H).
Mass, m/e: 481(M$^+$), 105(base).

b: 3-(4-Fluorophenyl)-5-(2-phenylpropionylamino)-4-{4-(2-aminopyrimidinyl)}isoxazole $^1$H-NMR(CDCl$_3$) δ: 11.21(s, 1H), 7.96(d, J=5.4 Hz, 1H), 7.50-7.37(m, 7H), 7.17(t, J=8.7 Hz, 2H), 6.06(d, J=5.4 Hz, 1H), 4.33(s, 2H), 3.95(q, J=6.9 Hz, 1H), 1.63(d, J=6.9 Hz, 3H).
Mass, m/e: 403(M$^+$), 255(base).

Example 318

4-[4-(2-Aminopyrimidinyl)]-3-(4-chlorophenyl)-5-(phenylacetylamino)isoxazole a: Synthesis of 2-(di-t-butoxycarbonylamino)-4-methylpyrimidine To 200 mL of an acetonitrile solution containing 9.15 g of 2-amino-4-methylpyrimidine, 40.26 g of di-t-butyl-dicarbonate, 18.65 g of triethylamine and 1.02 g of DMAP were added and stirred for 2 hours at room temperature. The solvent was distilled off from the reaction solution under reduced pressure. The residue was dissolved in ethyl acetate and washed with 10% aqueous potassium hydrogensulfate solution and then with saturated brine, dried over anhydrous magnesium sulfate and removed of the solvent by distillation under reduced pressure. The residue was washed with ether to provide 15.35 g (yield: 59%) of the title compound as a pale yellow crystal.
$^1$H-NMR(CDCl$_3$) δ: 8.59(d, J=5.1 Hz, 1H), 7.06(d, J=5.1 Hz, 1H), 2.54(s, 3H), 1.45(s, 18H).

b: Synthesis of 4-(2-di-butoxycarbonylaminopyrimidinyl)acetonitrile

A mixture of 15.34 g of 2-(di-t-butoxycarbonylamino)-4-methylpyrimidine and 25.91 g of t-butoxybisdimethylaminomethane was stirred for 40 minutes at 110° C. The reaction solution was cooled and from which t-butoxybisdimethylaminomethane was distilled off under reduced pressure. To the residue 150 mL of water and 16.83 g of hydroxylamine-O-sulfonic acid were added, and stirred for an hour at room temperature. The reaction solution was rendered basic with addition of sodium hydrogencarbonate and extracted with ethyl acetate. The ethyl acetate extract was dried over anhydrous magnesium sulfate and removed of the solvent by distillation under reduced pressure. The residue was purified on 120 g silica gel column chromatography (eluent, chloroform:methanol=50:1) to provide 5.27 g (yield: 32%) of the title compound as an yellow crystal.
$^1$H-NMR(CDCl$_3$) δ: 8.80(d, J=5.1 Hz, 1H), 7.37(d, J=5.1 Hz, 1H), 3.92(s, 2H), 1.48(s, 18H).

c: Synthesis of 5-amino-3-(4-chlorophenyl)-4-{4-[2-(di-t-butoxycarbonylamino)pyrimidinyl]}isoxazole To 10 mL of a methanol solution containing 0.136 g of sodium methoxide, 10 mL of a THF solution containing 0.7 g of 4-[2-(di-t-butoxycarbonylamino)pyrimidinyl]acetonitrile was added and stirred for 45 minutes at room temperature. Then 10 mL of a methanol solution containing 0.439 g of 4-chlorobenzhydroxymoyl chloride was added under cooling with ice, followed by 2 hours' stirring at room temperature. From the reaction solution the solvent was distilled off under reduced pressure, and water was added to the residue. Whereupon precipitated solid was recovered by filtration, washed with water, dissolved in chloroform-methanol, dried over anhydrous magnesium sulfate, decolorized with NORIT and removed of the solvent by distillation under reduced pressure. The residue was washed with ether-hexane to provide 0.444 g (yield: 43%) of the title compound as a pale yellow crystal.
$^1$H-NMR(CDCl$_3$) δ: 8.21(d, J=5.6 Hz, 1H), 7.48(s, 4H), 7.07(bs, 2H), 6.44(d, J=5.6 Hz, 1H), 1.53(s, 18H).
Mass, m/e: 487(M$^+$), 57(base).

d: Synthesis of 3-(4-chlorophenyl)-4-{4-[2-(di-t-butoxycarbonylamino)pyrimidinyl]}-5-(phenylacetylamino)isoxazole In 5 mL of THF, 0.042 g of imidazole and 0.187 g of DBU were dissolved, and to the solution 0.095 g of phenylacetyl chloride was added under cooling with ice, followed by 40 minutes' stirring at room temperature. Then 5 mL of a THF solution containing 0.1 g of 5-amino-3-(4-chlorophenyl)-4-{4-[2-(di-t-butoxycarbonylamino)-pyrimidinyl]}isoxazole was added and stirred for 1.5 hours at room temperature. After addition of water, the reaction solution was extracted with ethyl acetate. The ethyl acetate extract was dried over anhydrous magnesium sulfate and removed of the solvent by distillation under reduced pressure. The residue was purified on preparative chromatography (developer, chloroform) and washed with ether-hexane to provide 0.095 g (yield: 77%) of the title compound as a colorless solid.
$^1$H-NMR(CDCl$_3$) δ: 11.61(s, 1H), 8.29(d, J=5.4 Hz, 1H), 7.50-7.24(m, 9H), 6.52(d, J=5.4 Hz, 1H), 4.05(s, 2H), 1.57(s, 18H).
Mass, m/e: 605(M$^+$−91), 57(base).

e: Synthesis of 4-[4-(2-aminopyrimidinyl)]-3-(4-chlorophenyl)-5-(phenylacetylamino)isoxazole To 0.093 g of 3-(4-chlorophenyl)-4-{4-[2-(di-t-butoxycarbonylamino)pyrimidinyl]}-5-(phenylacetylamino)-isoxazole, 0.5 mL of TFA was added and stirred for an hour at room temperature. Saturated aqueous sodium hydrogencarbonate solution was added to the reaction solution under cooling with ice, and the precipitated solid was recovered by filtration. The solid was washed with water and dried under reduced pressure. The residue was washed with ether to provide 0.080 g (yield: 90%) of the title compound as a colorless crystal.

$^1$H-NMR(CDCl$_3$) δ: 11.51(s, 1H), 7.97(d, J=5.4 Hz, 1H), 7.51-7.38(m, 9H), 6.07(d, J=5.4 Hz, 1H), 4.30(bs, 2H), 3.97 (s, 2H).

Mass, m/e: 405(M$^+$), 270(base).

Example 319

4-[4-(2-Aminopyrimidinyl)]-3-(4-chlorophenyl)-5-[(2-chlorophenyl)acetylamino]isoxazole a: Synthesis of 3-(4-chlorophenyl)-5-[(2-chlorophenyl)acetylamino]-4-{4-[2-(di-t-butoxycarbonylamino) pyrimidinyl]}isoxazole To 5 mL of a THF solution containing 0.094 g of 2'-chlorophenylacetic acid, 0.09 g of CDI was added and stirred for 1.5 hours at room temperature. Then 5 mL of a THF solution containing 0.168 g of DBU and 0.09 g of 5-amino-3-(4-chlorophenyl)-4-{4-[2-(di-t-butoxycarbonylamino)pyrimidinyl]}isoxazole was added and stirred at 60° C. for 3.5 hours. From the reaction solution the solvent was distilled off under reduced pressure, and water was added to the residue which then was extracted with ethyl acetate. The organic layer was dried over anhydrous magnesium sulfate and then the solvent was distilled off under reduced pressure. The residue was purified on preparative chromatography (developer, chloroform) to provide 0.088 g (yield: 75%) of the title compound as a colorless solid.

$^1$H-NMR(CDCl$_3$) δ: 11.76(s, 1H), 8.30(d, J=5.4 Hz, 1H), 7.48(dd, J=8.8 Hz, 12.3 Hz, 4H), 7.41-7.35(m, 2H), 7.27-7.23 (m, 2H), 6.54(d, J=5.4 Hz, 1H), 4.22(s, 2H), 1.55(s, 18H).

Mass, m/e: 514(M$^+$−125), 57(base).

b: Synthesis of 4-[4-(2-aminopyrimidinyl)]-3-(4-chlorophenyl)-5-[(2-chlorophenyl)acetylamino]isoxazole To 0.086 g of 3-(4-chlorophenyl)-5-[(2-chlorophenyl)-acetylamino]-4-{4-[2-(di-t-butoxycarbonylamino)pyrimidinyl]}-isoxazole, 0.5 mL of TFA was added and stirred for an hour at room temperature. Saturated aqueous sodium hydrogencarbonate solution was added to the reaction solution under cooling with ice, and the precipitated solid was recovered by filtration. The solid was washed with water and dried under reduced pressure. Thus obtained residue was washed with ether to provide 0.043 g (yield: 73%) of the title compound as a colorless crystal.

$^1$H-NMR(CDCl$_3$) δ: 11.05(s, 1H), 7.92(d, J=5.4 Hz, 1H), 7.55-7.35(m, 8H), 6.13(d, J=5.4 Hz, 1H), 4.08(s, 2H), 2.55 (bs, 2H).

Mass, m/e: 439(M$^+$), 271(base)

The compounds of Examples 320-326 were synthesized in the manner similar to Examples 318 and 319.

Example 320

4-[4-(2-Aminopyrimidinyl)]-3-(4-chlorophenyl)-5-[3-methoxyphenyl)acetylamino]isoxazole a: 3-(4-Chlorophenyl)-4-{4-[2-(di-t-butoxycarbonylamino)pyrimidinyl]}-5-[(3-methoxyphenyl)acetylamino]isoxazole $^1$H-NMR(CDCl$_3$) δ: 11.61(s, 1H), 8.28(d, J=5.4 Hz, 1H), 7.47(dd, J=8.7 Hz, 14.8 Hz, 4H), 7.25-7.21(m, 1H), 7.00-6.94 (m, 2H), 6.81(dd, J=2.3 Hz, 8.1 Hz, 1H), 6.52(d, J=5.4 Hz, 1H), 4.03(s, 2H), 3.79(s, 3H), 1.57(s, 18H).

Mass, m/e: 514(M$^+$−121), 56(base).

b: 4-[4-(2-Aminopyrimidinyl)]-3-(4-chlorophenyl)-5-[(3-methoxyphenyl)acetylamino]isoxazole $^1$H-NMR(CDCl$_3$) δ: 10.77(s, 1H), 7.71(d, J=6.4 Hz, 1H), 7.50(d, J=8.5 Hz, 2H), 7.46-7.37(m, 3H), 7.02-6.94(m, 3H), 6.16(d, J=6.5 Hz, 1H), 3.94(s, 2H), 3.84(s, 3H), 3.60(bs, 2H).

Mass, m/e: 435(M$^+$), 271(base).

Example 321

4-[4-(2-Aminopyrimidinyl)]-5-(phenylacetylamino)-3-(4-fluoro-3-methylphenyl)isoxazole a: 5-Amino-4-{4-[2-(di-t-butoxycarbonylamino) pyrimidinyl])-3-(4-fluoro-3-methylphenyl)isoxazole $^1$H-NMR(CDCl$_3$) δ: 8.20(d, J=5.4 Hz, 1H), 7.39-7.34(m, 1H), 7.33-7.27(m, 1H), 7.12(t, J=8.9 Hz, 1H), 7.03(bs, 2H), 6.47(d, J=5.4 Hz, 1H), 2.33(s, 3H), 1.53(s, 18H).

Mass, m/e: 485(M$^+$), 57(base).

b: 4-{4-[2-(Di-t-butoxycarbonylamino)pyrimidinyl]}-3-(4-fluoro-3-methylphenyl)-5-(phenylacetylamino) isoxazole $^1$H-NMR(CDCl$_3$) δ: 11.60(s, 1H), 8.28(d, J=5.4 Hz, 1H), 7.42-7.24(m, 7H), 7.12(t, J=8.9 Hz, 1H), 6.54(d, J=5.4 Hz, 1H), 4.05(s, 2H), 2.32(d, J=1.9 Hz, 3H), 1.57(s, 18H).

Mass, m/e: 512(M$^+$−91), 57(base).

c: 4-[4-(2-Aminopyrimidinyl)]-5-(phenylacetylamino)-3-(4-fluoro-3-methylphenyl)isoxazole $^1$H-NMR(CDCl$_3$) δ: 11.16(s, 1H), 7.95(d, J=5.4 Hz, 1H), 7.51-7.38(m, 5H), 7.34-7.29(m, 1H), 7.27-7.20(m, 1H), 7.09 (t, J=8.9 Hz, 1H), 6.09(d, J=5.4 Hz, 1H), 4.36(bs, 2H), 3.98(s, 2H), 2.31(d, J=1.9 Hz, 3H).

Mass, m/e: 403(M$^+$), 269(base).

Example 322

4-[4-(2-Aminopyrimidinyl)]-5-[(2-chlorophenyl) acetylamino]-3-(4-fluoro-3-methylphenyl)isoxazole a: 4-{4-[2-(Di-t-butoxycarbonylamino)pyrimidinyl]}-3-(4-fluoro-3-methylphenyl)-5-[(2-methoxyphenyl) acetylamino]isoxazole $^1$H-NMR(CDCl$_3$) δ: 11.74(s, 1H), 8.29(d, J=5.4 Hz, 1H), 7.41-7.35(m, 3H), 7.31-7.21(m, 3H), 7.12(t, J=8.9 Hz, 1H), 6.56(d, J=5.4 Hz, 1H), 4.22(s, 2H), 2.32(s, 3H), 1.55(s, 18H).

Mass, m/e: 512(M$^+$−125), 57(base).

b: 4-[4-(2-Aminopyrimidinyl)]-5-[(2-chlorophenyl) acetylamino]-3-(4-fluoro-3-methylphenyl)isoxazole $^1$H-NMR(CDCl$_3$) δ: 11.03(s, 1H), 7.88(d, J=5.8 Hz, 1H), 7.55-7.46(m, 2H), 7.42-7.36(m, 2H), 7.34-7.30(m, 1H), 7.27-7.21(m, 1H), 7.12(t, J=8.9 Hz, 1H), 6.16(d, J=5.8 Hz, 1H), 4.09(s, 2H), 2.48(bs, 2H), 2.32(d, J=1.5 Hz, 3H).

Mass, m/e: 437(M$^+$), 125(base).

Example 323

4-[4-(2-Aminopyrimidinyl)]-3-(4-fluoro-3-methylphenyl)-5-[(3-methoxyphenyl)acetylamino]isoxazole a: 4-{4-[2-(Di-t-butoxycarbonylamino)pyrimidinyl]}-3-(4-fluoro-3-methylphenyl)-5-[(3-methoxyphenyl)acetylamino]isoxazole $^1$H-NMR(CDCl$_3$) δ: 11.60(s, 1H), 8.27(d, J=5.4 Hz, 1H), 7.40-7.20(m, 3H), 7.12(t, J=8.9 Hz, 1H), 7.02-6.94(m, 2H), 6.81(dd, J=1.7 Hz, 8.3 Hz, 1H), 6.54(d, J=5.4 Hz, 1H), 4.03(s, 2H), 3.79(s, 3H), 2.32(s, 3H), 1.57(s, 18H).
Mass, m/e: 512(M$^+$−121), 57(base).

b: 4-[4-(2-Aminopyrimidinyl)]-3-(4-fluoro-3-methylphenyl)-5-[(3-methoxyphenyl)acetylamino]isoxazole $^1$H-NMR(CDCl$_3$) δ: 10.75(s, 1H), 7.68(d, J=6.6 Hz, 1H), 7.43(t, J=7.9 Hz, 1H), 7.31-7.18(m, 2H), 7.14(t, J=8.7 Hz, 1H), 7.02-6.93(m, 3H), 6.19(d, J=6.6 Hz, 1H), 3.95(s, 2H), 3.85(s, 3H), 2.32(s, 3H).
Mass, m/e: 433(M$^+$), 269(base).

Example 324

4-[4-(2-Aminopyrimidinyl)]-3-(3-benzyloxyphenyl)-5-(phenylacetylamino)isoxazole a: 5-Amino-3-(3-benzyloxyphenyl)-4-{4-[2-(di-t-butoxycarbonylamino)pyrimidinyl]}isoxazole $^1$H-NMR(CDCl$_3$) δ: 8.17(d, J=5.6 Hz, 1H), 7.45-7.27(m, 7H), 7.11-7.05(m, 4H), 6.19(d, J=5.6 Hz, 1H), 5.07(s, 2H), 1.51(s, 18H).
Mass, m/e: 459(M$^+$−1), 91(base).

b: 3-(3-benzyloxyphenyl)-4-{4-[2-(di-t-butoxycarbonylamino)pyrimidinyl]}-5-(phenylacetylamino)isoxazole $^1$H-NMR(CDCl$_3$) δ: 11.73(s, 1H), 8.24(d, J=5.4 Hz, 1H), 7.44-7.30(m, 12H), 7.11-7.07(m, 2H), 6.30(d, J=5.4 Hz, 1H), 5.07(s, 2H), 4.07(s, 2H), 1.56(s, 18H).
Mass, m/e: 677(M$^+$−175), 59(base).

c: 4-[4-(2-Aminopyrimidinyl)]-3-(3-benzyloxyphenyl)-5-(phenylacetylamino)isoxazole $^1$H-NMR(CDCl$_3$) δ: 11.23(s, 1H), 7.90(d, J=5.4 Hz, 1H), 7.54-7.28(m, 12H), 7.10-7.02(m, 2H), 5.87(d, J=5.4 Hz, 1H), 5.05(s, 2H), 4.43(bs, 2H), 3.99(s, 2H).
Mass, m/e: 476(M$^+$−1), 91(base).

Example 325

4-[4-(2-Aminopyrimidinyl)]-3-(3-benzyloxyphenyl)-5-[(2-chlorophenyl)acetylamino]isoxazole a: 3-(3-Benzyloxyphenyl)-5-[(2-chlorophenyl)acetylamino]-4-{4-[2-(di-t-butoxycarbonylamino)pyrimidinyl]}isoxazole $^1$H-NMR(CDCl$_3$) δ: 11.87(s, 1H), 8.24(d, J=5.4 Hz, 1H), 7.43-7.20(m, 11H), 7.12-7.07(m, 2H), 6.31(d, J=5.4 Hz, 1H), 5.08(s, 2H), 4.24(s, 2H), 1.54(s, 18H)
Mass, m/e: 536(M$^+$−175), 91(base). .

b: 4-[4-(2-Aminopyrimidinyl)]-3-(3-benzyloxyphenyl)-5-[(2-chlorophenyl)acetylamino]isoxazole $^1$H-NMR(CDCl$_3$) δ: 11.26(bs, 1H), 7.95(d, J=5.4 Hz, 1H), 7.54-7.48(m, 2H), 7.43-7.29(m, 9H), 7.10-7.03(m, 2H), 5.91(d, J=5.4 Hz, 1H), 5.06(s, 2H), 4.69(bs, 2H), 4.10(s, 2H).
Mass, m/e: 393(M$^+$−102), 91(base).

Example 326

4-[4-(2-Aminopyrimidinyl)]-3-(3-benzyloxyphenyl)-5-[(3-methoxyphenyl)acetylamino]isoxazole a: 3-(3-Benzyloxyphenyl)-4-{4-[2-(di-t-butoxycarbonylamino)pyrimidinyl]}-5-[(3-methoxyphenyl)acetylamino]isoxazole $^1$H-NMR(CDCl$_3$) δ: 11.73(s, 1H), 8.23(d, J=5.4 Hz, 1H), 7.44-7.20(m, 8H), 7.12-7.04(m, 2H), 7.04-6.95(m, 2H), 6.84-6.79(m, 1H), 6.30(d, J=5.4 Hz, 1H), 5.07(s, 2H), 4.05(s, 2H), 3.79(s, 3H), 1.56(s, 18H).
Mass, m/e: 541(M$^+$−166), 91(base).

b: 4-[4-(2-Aminopyrimidinyl)]-3-(3-benzyloxyphenyl)-5-[(3-methoxyphenyl)acetylamino]isoxazole $^1$H-NMR(CDCl$_3$) δ: 11.22(s, 1H), 7.93(d, J=5.4 Hz, 1H), 7.43-7.29(m, 8H), 7.10-6.90(m, 5H), 5.87(d, J=5.4 Hz, 1H), 5.05(s, 2H), 4.49(bs, 2H), 3.94(s, 2H), 3.83(s, 3H).
Mass, m/e: 420(M$^+$−87), 91(base).

Preparation Example 1

| Tablet: | |
| --- | --- |
| | mg/tablet |
| Active ingredient | 5.0 |
| Starch | 10.0 |
| Lactose | 73.0 |
| Carboxymethyl cellulose calcium | 10.0 |
| Talc | 1.0 |
| Magnesium stearate | 1.0 |
| | 100.0 |

The active ingredient was pulverized to a grain size not greater than 70 μm, and to which starch, lactose and carboxymethyl cellulose calcium were added and thoroughly mixed. Ten (10) % starch paste was added to the mixture, mixed by stirring and granulated. After drying, the granules were dressed to around 1000 μm. Mixing talc and magnesium stearate therewith, the blend was tabulated.

The invention claimed is:

1. An isoxazole compound represented by formula (I)

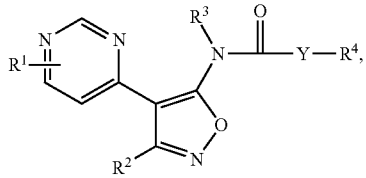

wherein:
$R^1$ stands for hydrogen, lower alkyl, amino, lower alkylamino, di-lower alkylamino, phenyl lower alkylamino, acylamino, halogen, lower alkoxy, lower alkylthio or lower alkylsulfinyl,
$R^2$ stands for unsubstituted aryl or heteroaryl, or aryl or heteroaryl which is substituted with 1-3 substituents selected from the group consisting of halogen, lower alkyl, lower alkoxy, lower haloalkyl, lower alkylenedioxy and benzyloxy,
$R^3$ stands for hydrogen or lower alkyl,
$R^4$ stands for substituted or unsubstituted phenyl, or substituted or unsubstituted heterocyclic group, and
Y stands for —(CH$_2$)$_n$—, —CO—, —CH(CH$_3$)—, —O—, —NH—,

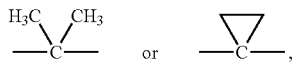

n being an integer of 0-3,
or a pharmaceutically acceptable salt thereof.

2. The isoxazole compound or pharmaceutically acceptable salt thereof according to claim 1, wherein $R^1$ stands for hydrogen, amino, lower alkylamino or di-lower alkylamino.

3. The isoxazole compound or pharmaceutically acceptable salt thereof according to claim 1, wherein $R^2$ stands for phenyl which is substituted with 1-3 substituents selected from the group consisting of halogen, lower alkyl, lower alkoxy and lower alkylenedioxy.

4. The isoxazole compound or pharmaceutically acceptable salt thereof according to claim 3, wherein $R^2$ is 4-fluorophenyl, 2,4-difluorophenyl, 4-chlorophenyl, 3-methylphenyl, 2-fluoro-5-methylphenyl, 4-fluoro-3-methylphenyl, 2-fluoro-4-methoxyphenyl or 2,3-methylenedioxyphenyl.

5. The isoxazole compound or pharmaceutically acceptable salt thereof according to claim 1, wherein $R^3$ stands for hydrogen.

6. The isoxazole compound or pharmaceutically acceptable salt thereof according to claim 1, wherein $R^4$ stands for substituted or unsubstituted phenyl.

7. The isoxazole compound or pharmaceutically acceptable salt thereof according to claim 6, wherein $R^4$ stands for unsubstituted phenyl or phenyl substituted with 1 or 2 substituents selected from the group consisting of halogen and lower alkyl.

8. The isoxazole compound or pharmaceutically acceptable salt thereof according to claim 7, wherein $R^4$ is unsubstituted phenyl, 2-halophenyl, 2,6-dihalophenyl, 2-lower alkylphenyl, 3-lower alkylphenyl, 3-lower alkoxyphenyl or 2,5-di-lower alkylphenyl.

9. The isoxazole compound or pharmaceutically acceptable salt thereof according to claim 1, wherein Y stands for —CH$_2$—.

10. An isoxazole compound selected from the group consisting of:
5-[(2-chlorophenyl)acetylamino]-3-(4-fluorophenyl)-4-(4-pyrimidinyl)isoxazole,
5-[(2-chloro-6-fluorophenyl)acetylamino]-3-(4-fluorophenyl)-4-(4-pyrimidinyl)isoxazole,
3-(4-chlorophenyl)-5-[(2-chlorophenyl)acetylamino]-4-(4-pyrimidinyl)isoxazole,
5-[(2-chlorophenyl)acetylamino]-3-(2,4-difluorophenyl)-4-(4-pyrimidinyl)isoxazole,
3-(2,4-difluorophenyl)-5-[(3-methylphenyl)acetylamino]-4-(4-pyrimidinyl)isoxazole,
5-[(2-chlorophenyl)acetylamino]-3-(2-fluoro-4-methoxyphenyl)-4-(4-pyrimidinyl)isoxazole,
5-[(2-chlorophenyl)acetylamino]-3-(2,3-methylenedioxyphenyl)-4(4-pyrimidinyl)isoxazole,
5-[(2-chlorophenyl)acetylamino]-3-(3-methylphenyl)-4-(4-pyrimidinyl)isoxazole,
5-[(2-bromophenyl)acetylamino]-3-(3-methylphenyl)-4-(4-pyrimidinyl)isoxazole,
3-(3-methylphenyl)-5-[(2-methylphenyl)acetylamino]-4-(4-pyrimidinyl)isoxazole,
3-(3-methylphenyl)-5-[(3-methylphenyl)acetylamino]-4-(4-pyrimidinyl)isoxazole,
3-(2-fluoro-5-methylphenyl)-5-(phenylacetylamino)-4-(4-pyrimidinyl)isoxazole,
5-[(3-methoxyphenyl)acetylamino]-3-(3-methyl-4-fluorophenyl)-4-(4-pyrimidinyl)isoxazole and
3-(3-methyl-4-fluorophenyl)-5-[(2-methylphenyl)acetylamino]-4-(4-pyrimidinyl)isoxazole,
or a pharmaceutically acceptable salt thereof.

* * * * *